(12) United States Patent
Kelly

(10) Patent No.: US 12,053,530 B2
(45) Date of Patent: *Aug. 6, 2024

(54) PLECTIN-1 BINDING ANTIBODIES AND USES THEREOF

(71) Applicant: ZIELBIO, INC., Charlottesville, VA (US)

(72) Inventor: Kimberly A. Kelly, Goochland, VA (US)

(73) Assignee: ZielBio, Inc., Charlottesville, VA (US)

( * ) Notice: Subject to any disclaimer, the term of this patent is extended or adjusted under 35 U.S.C. 154(b) by 641 days.

This patent is subject to a terminal disclaimer.

(21) Appl. No.: 16/846,031

(22) Filed: Apr. 10, 2020

(65) Prior Publication Data

US 2020/0268900 A1   Aug. 27, 2020

Related U.S. Application Data

(63) Continuation-in-part of application No. PCT/US2018/055438, filed on Oct. 11, 2018.

(60) Provisional application No. 62/571,246, filed on Oct. 11, 2017.

(51) Int. Cl.

| *A61K 39/00* | (2006.01) |
|---|---|
| *A61K 31/282* | (2006.01) |
| *A61K 31/519* | (2006.01) |
| *A61K 31/7068* | (2006.01) |
| *A61K 47/65* | (2017.01) |
| *A61K 47/68* | (2017.01) |
| *A61P 35/00* | (2006.01) |
| *C07K 16/18* | (2006.01) |
| *C07K 16/30* | (2006.01) |

(52) U.S. Cl.
CPC ........ *A61K 47/6803* (2017.08); *A61K 31/282* (2013.01); *A61K 31/519* (2013.01); *A61K 31/7068* (2013.01); *A61K 47/65* (2017.08); *A61P 35/00* (2018.01); *C07K 16/18* (2013.01); *C07K 16/30* (2013.01); *C07K 16/303* (2013.01); *C07K 2317/73* (2013.01); *C07K 2317/92* (2013.01)

(58) Field of Classification Search
CPC ....... A61P 35/00; C07K 16/30; C07K 16/303; A61K 47/6851; A61K 2039/505
See application file for complete search history.

(56) References Cited

U.S. PATENT DOCUMENTS

| 4,946,778 | A | 8/1990 | Ladner et al. | |
|---|---|---|---|---|
| 5,260,203 | A | 11/1993 | Ladner et al. | |
| 9,387,265 | B2 * | 7/2016 | Kelly | A61K 49/0056 |
| 11,168,145 | B2 | 11/2021 | Kelly et al. | |
| 2003/0118592 | A1 | 6/2003 | Ledbetter et al. | |
| 2004/0101874 | A1 | 5/2004 | Ghosh et al. | |
| 2005/0164324 | A1 | 7/2005 | Gygi | |
| 2009/0110680 | A1 * | 4/2009 | Sieger | A61K 51/1018 424/134.1 |
| 2009/0186031 | A1 | 7/2009 | Wood et al. | |
| 2010/0279932 | A1 | 11/2010 | Ledbetter et al. | |
| 2011/0182814 | A1 | 7/2011 | Kelly et al. | |
| 2011/0271357 | A1 | 11/2011 | Kim et al. | |
| 2012/0213773 | A1 | 8/2012 | Ledbetter et al. | |
| 2015/0151010 | A1 | 6/2015 | Kelly et al. | |
| 2015/0299334 | A1 | 10/2015 | Bamdad | |
| 2016/0137725 | A1 | 5/2016 | Gu et al. | |
| 2017/0087257 | A1 | 3/2017 | Kelly et al. | |
| 2017/0267719 | A1 | 9/2017 | Madamsetty et al. | |
| 2019/0119397 | A1 | 4/2019 | Kelly et al. | |
| 2022/0119546 | A1 | 4/2022 | Kelly et al. | |

FOREIGN PATENT DOCUMENTS

| CN | 102762984 A | 10/2012 |
|---|---|---|
| JP | 2011521897 A | 7/2011 |
| WO | WO-8801649 A1 | 3/1988 |
| WO | WO 2009/036092 A2 | 3/2009 |
| WO | WO-2009129220 A2 | 10/2009 |
| WO | WO 2017/177199 A2 | 10/2017 |
| WO | WO 2019/075216 A1 | 4/2019 |

OTHER PUBLICATIONS

Strome et al., The Oncologist, 2007; 12:1084-95 (Year: 2007).*
Brand et al., Anticancer Res. 2006; 26:463-70 (Year: 2006).*
Paul, Fundamental Immunology, 3rd Edition, 1993, pp. 292-295 (Year: 1993).*
Almagro & Fransson, Frontiers in Bioscience 2008; 13:1619-33 (Year: 2008).*
Rudikoff et al Proc. Natl. Acad. Sci. USA 1982 vol. 79: p. 1979 (Year: 1982).*
Pascalis et al (The Journal of Immunology (2002) 169, 3076-3084) (Year: 2002).*
Casset et al. (2003) BBRC 307, 198-205 (Year: 2003).*
D'Angelo et al, Frontiers in Immunology vol. 9 p. 1 (2018) (Year: 2018).*
Lesterhuis et al PLOS One vol. 8 p. e61895 (2013) (Year: 2013).*
Katada, at al., "Plectin promotes migration and invasion of cancer cells and is a novel prognostic marker for head and neck squamous cell carcinoma," J Proteomics, Dec. 30, 2011, Vo. 75(6), pp. 1803-1815.
NCBI Genbank Accession No. XP_006716652, Feb. 3, 2014, 2 pages.
Oddveig, R. G. et al., "Plectin as a prognostic marker in nonmetastatic oral squamous cell carcinoma," BMC Oral Health, 15:98 (2015), 9 pages; doi:10.1186/s12903-015-0084-9.

(Continued)

*Primary Examiner* — Sheela J. Huff
(74) *Attorney, Agent, or Firm* — COOLEY LLP; Heidi A. Erlacher; Jessica D. Cande

(57) ABSTRACT

Aspects of the disclosure provide compositions and methods for treating cancer characterized by surface expression of plectin-1. The disclosure relates, in part, to combinations of therapeutic agents (e.g., anti-plectin-1 antibodies and certain small molecules) that function together (e.g., synergistically) to inhibit cancer cell growth. In some embodiments, the disclosure relates to anti-plectin-1 antibody-drug-conjugates (ADCs).

18 Claims, 7 Drawing Sheets

Specification includes a Sequence Listing.

(56) References Cited

OTHER PUBLICATIONS

International Search Report and Written Opinion mailed Sep. 22, 2017 for International Application No. PCT/US2017/026711, 13 pages.
International Search Report and Written Opinion mailed Jan. 24, 2019 for International Application No. PCT/US2018/055438, 15 pages.
Abcam Product Datasheet, "Immunogen: A recombinant fragment comprising the C-terminal 220 amino acids of plectin," Jan. 19, 2015; retrieved from http://www.abcam.com/plectin-antibody-e398p-ab32528.html; 6 pages.
Aho, S. et al., "Plectin Serves as an Autoantigen in Paraneoplastic Pemphigus," The Journal of Investigative Dermatology, 113(3):422-423 (1999).
Antonow, D. & Thurston, D. E., "Synthesis of DNA-Interactive Pyrrolo[2,1-c][1,4]benzodiazepines (PBDs)," Chem. Rev., 111:2815-2864 (2011).
Brentnall, T. A. et al., "Early Diagnosis and Treatment of Pancreatic Dysplasia in Patients with a Family History of Pancreatic Cancer," Ann Intern. Med., 131:247-255 (1999).
Canto, M. I. et al., "Screening for Pancreatic Neoplasia in High-Risk Individuals: An EUS-Based Approach," Clinical Gastroenterolgoy and Hepatology, 2:606-621 (2004).
Cheng, C.-C. et al., "Plectin deficiency in liver cancer cells promotes cell migration and sensitivity to sorafenib treatment," Cell Ahesion & Migration, 12(1):19-27 (2018).
Cipolla, L. et al., "Pyrrolo[2,1-c][1,4]benzodiazepine as a Scaffold for the Design and Synthesis of Anti-Tumour Drugs," Anti-Cancer Agents in Medicinal Chemistry, 9:1-31 (2009).
Gerratana, B., "Biosynthesis, Synthesis, and Biological Activities of Pyrrolobenzodiazepines," Med Res Rev, 32(2):254-293 (2012).
Goggins, M. "Molecular Markers of Early Pancreatic Cancer," J Clin Oncol, 23:4524-4531 (2005).
Köhler, G. & Milstein, C., "Continuous cultures of fused cells secreting antibody of predefined specificity," Nature, 256:495-497 (1975).
Li, D. et al., "Pancreatic Cancer," Lancet, 363:1049-1057 (2004).
Pelaez-Luna, M. et al., "Resectability of Presymptomatic Pancreatic Cancer and Its Relationship to Onset of Diabetes: A Retrospective Review of CT Scans and Fasting Glucose Values Prior to Diagnosis," Am J Gastroenterol, 102:2157-2163 (2007).
Proby, C. et al., "Human Autoantibodies against HD1/Plectin in Paraneoplastic Pemphigus," J Invest Dermatol, 112:153-156 (1999).
Rikardsen, O. G. et al., "Plectin as a prognostic marker in non-metastatic oral squamous cell carcinoma," BMC Oral Heatlh, 15:98 (2015), 9 pages; doi:10.1186/s12903-015-0084-9.
Shin, S. J. et al., "Unexpected gain of function for the scaffolding protein plectin due to mislocalization in pancreatic cancer," PNAS, 110(48):19414-19419 (2013).
Sonnenberg, A. & Liem, R. K. H., "Plakins in development and disease," Experimental Cell Research, 313:2189-2203 (2007).
UniProtKB—Q15149, Oct. 14, 2008, http://www.uniprot.org/uniprot/Q15149, 19 pages.
Wayback Machine, https://web.archive.org/web/*/http://www.abcam.com/plectin-antibody-e398p-ab32528.html, Aug. 25, 2017, used to establish Abcam Product Databshet, 3 pages.
Yeo, C. J. et al., "A prospective randomized trial of pancreaticogastrostomy versus pancreaticojejunostomy after pancreaticoduodenectomy," Annals of Surgery, 222(4):580-592 (1995).
Abou-Alfa, G. K. et al., "Pemigatinib for previously treated, locally advanced or metastatic cholangiocarcinoma: a multicentre, open-label, phase 2 study," Lancet Oncol., 21:671-684 (2020).
Abudaker, K. et al., "Inhibition of the JAK2/STAT3 Pathway in Ovarian Cancer Results in the Loss of Cancer Stem Cell-like Characteristics and a Reduced Tumor Burden," BMC Cancer, 14:317 (2014); doi:10.1186/1471-2407-14-317, 22 pages.
Ahmed, N. et al., "Unique Proteome Signature of Post-Chemotherapy Ovarian Cancer Ascites-Derived Tumor Cells," Sci. Rep., 6:30061 (2016); doi:10.1038/srep30061, 13 pages.

Banales, J. M. et al., "Cholangiocarcinoma 2020: the next horizon in mechanisms and management," Nat Rev Gastroenterol Hepatol., Nature Reviews Gastroenterology & Hepatology, 17:557-588 (2020).
Bankhead, P. et al., QuPath: Open source software for digital pathology image analysis. Sci Rep 7, 16878 (2017), 7 pages.
Bausch, D. et al., "Plectin-1 is a Biomarker of Malignant Pancreatic Intraductal Papillary Mucinous Neoplasms," J Gastrointest Surg., 13:1948-1954 (2009).
Bausch, D. et al., "Plectin-1 as a Novel Biomarker for Pancreatic Cancer," Clin Cancer Res, 17(2):302-309 (2010).
Berenbaum, M. C., "What is synergy?" Pharmacol Rev., 41:93-141 (1989).
Bray, F. et al., "Global cancer statistics 2018: GLOBOCAN estimates of incidence and mortality worldwide for 36 cancers in 185 countries," CA Cancer J Clin., 68:394-424 (2018).
Brinton, L. T. et al., "Cotargeting of XPO1 Enhances the Antileukemic Activity of Midostaurin and Gilteritinib in Acute Myeloid Leukemia," Cancers, 12:1574 (2020), doi:10.3390/cancers12061574, 16 pages.
Buckup, M. et al., "Plectin is a Regulator of Prostate Cancer Growth and Metastasis," Oncogene, 40:663-676 (2021); doi:10.1038/s41388-020-01557-9.
Burch, T. C. et al., "Variable Metastatic Potentials Correlate with Differential Plectin and Vimentin Expression in Syngeneic Androgen Independent Prostate Cancer Cells," PLoS ONE, 8:e65005 (2013); doi:10.1371/journal.pone.0065005, 13 pages.
Carter, P. J. & Lazar, G. A., "Next generation antibody drugs: pursuit of the 'high-hanging fruit,'" Nat Rev Drug Discov., 17:197-223 (2018).
Chandrashekar, D. S. et al., "UALCAN: A Portal for Facilitating Tumor Subgroup Gene Expression and Survival Analyses," Neoplasia, 19(8):649-658 (2017).
Chen, W. et al., "Delivery of MiR-212 by Chimeric Peptide-Condensed Supramolecular Nanoparticles Enhances the Sensitivity of Pancreatic Ductal Adenocarcinoma to Doxorubicin," Biomaterials, 192:590-600 (2019); doi:10.1016/j.biomaterials.2018.11.035.
Chen, X. et al., "Plectin-1 Targeted Dual-modality Nanoparticles for Pancreatic Cancer Imaging," EBioMedicine, 30:129-137 (2018).
Chothia et al., "Canonical structures for the hypervariable regions of immunoglobulins," J. Mol. Biol. 1964(4):901-917 (1987).
Chothia et al., "Conformations of immunoglobulin hypervariable regions," Nature 342:877-883 (1989).
Colomiere, M. et al., "Cross Talk of Signals between EGFR and IL-6R through JAK2/STAT3 Mediate Epithelial-Mesenchymal Transition in Ovarian Carcinomas," Br. J. Cancer, 100:134-144 (2009), doi:10.1038/sj.bjc.6604794.
Cortez, A.J. et al., "Advances in Ovarian Cancer Therapy," Cancer Chemother. Pharmacol., 81:17-38 (2018); doi:10.1007/s00280-017-3501-8.
Dasa, S. S. K. et al., "Plectin-targeted liposomes enhance the therapeutic efficacy of a PARP inhibitor in the treatment of ovarian cancer," Theranostics, 8(10):2782-2798 (2018).
Datta-Mannan, A., et al., "Humanized IgG1 variants with differential binding properties to the neonatal Fc receptor: relationship to pharmacokinetics in mice and primates", Drug Metabolism and Disposition; 35(1): 86-94 (2007).
De Carvalho, V. P. et al., "The Contribution and Perspectives of Proteomics to Uncover Ovarian Cancer Tumor Markers," Transl. Res., 206:71-90 (2019); doi:10.1016/j.trsl.2018.11.001.
Di Veroli, G. Y. et al., "Combenefit: an interactive platform for the analysis and visualization of drug combinations," Bioinformatics, 32:2866-2868 (2016).
Dimastromatteo, J. et al., "Abstract 1558: Therapeutic targeting of cell surface plectin induces anti-cancer immune response and pancreatic cancer regression," Cancer Res, Jul. 1, 2019; 79 (13_Supplement):1558. doi.org/10.1158/1538-7445.AM2019-1558, 2 pages.
Eisenhauer, E. A. et al., "New response evaluation criteria in solid tumours: Revised RECIST guideline (version 1.1)," European Journal of Cancer, 45:228-247 (2009).
Farshidfar, F. et al., "Integrative Genomic Analysis of Cholangiocarcinoma Identifies Distinct IDH-Mutant Molecular Profiles," Cell Rep., 18:2780-2794 (2017), 28 pages.

(56) References Cited

OTHER PUBLICATIONS

Galliverti, G. et al., "Myeloid cells orchestrate systemic immunosuppression, impairing the efficacy of immunotherapy against HPV+ cancers," Cancer Immunol Res., 8:131-145 (2020).
Graham, R. P. et al., "Fibroblast growth factor receptor 2 translocations in intrahepatic cholangiocarcinoma," Hum Pathol., 45:1630-1638 (2014).
Gunderson, A. J. et al., "Bruton Tyrosine Kinase-Dependent Immune Cell Cross-talk Drives Pancreas Cancer," Cancer Discov., 6(3):270-285 (2016).
Guo, Q. et al., "CXCL7 promotes proliferation and invasion of cholangiocarcinoma cells," Oncol Rep., 37(2):1114-1122 (2017).
Györffy, B., "Discovery and ranking of the most robust prognostic biomarkers in serous ovarian cancer," Geroscience, 45:1889-1898 (2023); doi: 10.1007/s11357-023-00742-4.
Györffy, B. et al., "Online Survival Analysis Software to Assess the Prognostic Value of Biomarkers Using Transcriptomic Data in Non-Small-Cell Lung Cancer," PLOS ONE, 8:e82241 (2013), doi:10.1371/journal.pone.0082241, 9 pages.
Hallas-Potts, A. et al., "Ovarian Cancer Cell Lines Derived from Non-Serous Carcinomas Migrate and Invade More Aggressively than Those Derived from High-Grade Serous Carcinomas," Sci. Rep., 9:5515 (2019); doi:10.1038/s41598-019-41941-4, 10 pages.
Högemann, D. et al., "Improvement of MRI Probes to Allow Efficient Detection of Gene Expression," Bioconjugate Chem., 11:941-946 (2000).
Hingorani, S. R. et al., "Trp53R172H and KrasG12D cooperate to promote chromosomal instability and widely metastatic pancreatic ductal adenocarcinoma in mice" Cancer Cell, 7:469-483 (2005).
Horoszewicz, J.S. et al., "LNCaP Model of Human Prostatic Carcinoma", Cancer Research, 43:1809-1818 (1983).
Idusogie, E. E. et al., "Mapping of the C1q binding site on rituxan, a chimeric antibody with a human IgG1 Fc," J Immunol., 164(8):4178-4184 (2000).
Johnson, G., & Wu, T.T., "Kabat Database and its applications: 30 years after the first variability plot," Nucl. Acids Res. 28(1):214-218 (2000).
Josephson, L. et al., "High-Efficiency Intracellular Magnetic Labeling with Novel Superparamagnetic-Tat Peptide Conjugates," Bioconjugate Chem., 10(2):186-191 (1999).
Kannarkat, G. J. et al., "Evaluation of Plectin-1 Immunohistochemical Expression in Human Colon Cancer Tumor Progression," J. Clin. Oncol., 27:e22132-e22132 (2009); doi:10.1200/jco.2009.27.15_suppl.e22132, 2 pages.
Kelly, K. A. et al., "Targeted Nanoparticles for Imaging Incipient Pancreatic Ductal Adenocarcinoma," PLoS Med, 5(4):e85, doi.org/10.1371/journal.pmed.0050085 (2008), 12 pages.
Klose, M. H. M. et al., "Bioimaging of Isosteric Osmium and Ruthenium Anticancer Agents by LA-ICP-MS," Metallomics, 10:388-396 (2018); doi:10.1039/C8MT00012C.
Knuth, A. et al., "Biliary adenocarcinoma: Characterisation of three new human tumor cell lines," J Hepatol., 1:579-596 (1985).
Koga, T. et al., "Individual Reference Intervals of Hematological and Serum Biochemical Parameters in Cynomolgus Monkeys," Int J Toxicol., 24:377-385 (2005).
Konkalmatt, P. R. et al., "Plectin-1 targeted AAV vector for the molecular imaging of pancreatic cancer," Frontiers in Oncology, vol. 3(84) (2018), www.frontiersin.org/journals/oncology/articles/10.3389/fonc.2013.00084/full, 6 pages.
Kostelny. S. A. et al., "Formation of a Bispecific Antibody by the Use of Leucine Zippers," The Journal of Immunology, 148(5):1547-1553 (1992).
Kurai, J., et al., "Antibody-Dependent Cellular Cytotoxicity Mediated by Cetuximab against Lung Cancer Cell Lines." Clinical Cancer Research 13(5):1552-1561 (2007).
Lamarca, A. et al., "Molecular targeted therapies: Ready for "prime time" in biliary tract cancer," J Hepatol., 73:170-185 (2020).
Leone, F. et al., "Panitumumab in combination with gemcitabine and oxaliplatin does not prolong survival in wild-type KRAS advanced biliary tract cancer: A randomized phase 2 trial (Vecti-BIL study)," Cancer, 122:574-581 (2016).
Leung, K. K. et al., "Broad and Thematic Remodeling of the Surfaceome and Glycoproteome on Isogenic Cells Transformed with Driving Proliferative Oncogenes," Proc. Natl. Acad. Sci., 117:7764-7775 (2020); doi:10.1073/pnas.1917947117.
Li, Q. et al., "DRAP: A Toolbox for Drug Response Analysis and Visualization Tailored for Preclinical Drug Testing on Patient-Derived Xenograft Models," J. Transl. Med., 17:39 (2019); doi:10.1186/s12967-019-1785-7, 9 pages.
Li, Y. et al., Development of a Tumor-Responsive Nanopolyplex Targeting Pancreatic Cancer Cells and Stroma, ACS Appl Mater Interfaces, 11:45390-45403 (2019).
Liang, R. et al., "STAT3 Signaling in Ovarian Cancer: A Potential Therapeutic Target," J. Cancer, 11:837-848 (2020); doi:10.7150/jca.35011.
Loisel, S. et al., "Relevance, advantages and limitations of animal models used in the development of monoclonal antibodies for cancer treatment," Crit Rev Oncol Hematol., 62:34-42 (2007).
MacCallum, R.M., et al., "Antibody-Antigen Interactions: Contact Analysis and Binding Site Topography," Journal of Molecular Biology, 262(5):732-745 (1996).
Malka, D. et al., "Gemcitabine and oxaliplatin with or without cetuximab in advanced biliary-tract cancer (BINGO): a randomised, open-label, non-comparative phase 2 trial," Lancet Oncol., 15:819-828 (2014).
Martin, A.C.R. et al., "Modeling antibody hypervariable loops: A combined algorithm," Proc. Natl. Acad. Sci. USA 86:9268-9272 (1989).
Martinko, A. J. et al., Targeting RAS-Driven Human Cancer Cells with Antibodies to Upregulated and Essential Cell-Surface Proteins, eLife, 7:e31098 (2018); doi:10.7554/eLife.31098, 25 pages.
McCarthy, J. R. et al., "Targeted delivery of multifunctional magnetic nanoparticles," Nanomedicine, 2(2):153-167 (2007).
McInroy, L. & Määttä, A., "Plectin Regulates Invasiveness of SW480 Colon Carcinoma Cells and is Targeted to Podosome-like Adhesions in an Isoform-Specific Manner," Exp. Cell Res., 317:2468-2478 (2011); doi:10.1016/j.yexcr.2011.07.013, 11 pages.
Medler, T. R. et al., "Complement C5a Fosters Squamous Carcinogenesis and Limits T Cell Response to Chemotherapy," Cancer Cell, 34(4):561-578 e566 (2018).
Medzihradszky, K. F., "Characterization of site-specific N-glycosylation." Methods Mol Biol. (2008); 446: 293-316.
Meier, S. M. et al., "An Organoruthenium Anticancer Agent Shows Unexpected Target Selectivity for Plectin," Angew Chem Int Ed., 56:8267-8271 (2017).
Meier-Menches, S. M. et al., "Time-Dependent Shotgun Proteomics Revealed Distinct Effects of an Organoruthenium Prodrug and Its Activation Product on Colon Carcinoma Cells," Metallomics., 11:118-127 (2019); doi:10.1039/c8mt00152a.
Miyagiwa, M. et al., "A new human cholangiocellular carcinoma cell line (HuCC-T1) producing carbohydrate antigen 19/9 in serum-free medium," In Vitro Cell Dev Biol., 25:503-510 (1989).
Moore, G. L., et al., "Engineered Fc variant antibodies with enhanced ability to recruit complement and mediate effector functions", mABs, 2(2):181-189 (2010).
Moris, M. et al., "Plectin-1 as a Biomarker of Malignant Progression in Intraductal Papillary Mucinous Neoplasms: A Multicenter Study," Pancreas, 45:1353-1358 (2016); doi:10.1097/MPA.0000000000000652.
Musrap, N. et al., "Proteomic Analysis of Cancer and Mesothelial Cells Reveals an Increase in Mucin 5AC during Ovarian Cancer and Peritoneal Interaction," J. Proteomics, 103:204-215 (2014); doi:10.1016/j.jprot.2014.03.042.
Overdijk, M. B. et al., "Crosstalk between Human IgG Isotypes and Murine Effector Cells," J Immunol., 189:3430-8343 (2012).
Pal, K. et al., "Multifaceted Peptide Assisted One-Pot Synthesis of Gold Nanoparticles for Plectin-1 Targeted Gemcitabine Delivery in Pancreatic Cancer," Nanoscale, 9:15622-15634 (2017), doi:10.1039/C7NR03172F.
Park, H.-K. et al., "Reference values of clinical pathology parameters in cynomolgus monkeys (*Macaca fascicularis*) used in preclinical studies," Lab Anim Res., 32:79-86 (2016).

(56) References Cited

OTHER PUBLICATIONS

Pawar, H. et al., "Quantitative Tissue Proteomics of Esophageal Squamous Cell Carcinoma for Novel Biomarker Discovery," Cancer Biol. Ther., 12:510-522 (2011); doi:10.4161/cbt.12.6.16833.
Perez, S. M. et al., "Abstract 3591: First in class drug ZB131 shows efficacy in cholangiocarcinoma models," Cancer Res, Jun. 15, 2022; 82 (12_Supplement):3591; doi.org/10.1158/1538-7445.AM2022-3591, 2 pages.
Perez, S. M. et al., "Abstract 6299: ZB131 antibody-drug conjugates induce potent antitumor activity," Cancer Res, Apr. 1, 2023; 83 (7_Supplement):6299; doi.org/10.1158/1538-7445.AM2023-6299, 2 pages.
Poli, V. & Camporeale, A., "STAT3-Mediated Metabolic Reprogramming in Cellular Transformation and Implications for Drug Resistance," Front. Oncol., 5:121 (2015); doi:10.3389/fonc.2015.00121, 9 pages.
Qi, Z. et al., "Tetramethoxychalcone, a Chalcone Derivative, Suppresses Proliferation, Blocks Cell Cycle Progression, and Induces Apoptosis of Human Ovarian Cancer Cells," PLOS ONE, 9:e106206 (2014); doi:10.1371/journal.pone.0106206, 11 pages.
Rashid, A. et al., "K-ras mutation, p53 overexpression, and microsatellite instability in biliary tract cancers: a population-based study in China," Clin Cancer Res, 8:3156-3163 (2002).
Raymond, A. C. et al., "Unbiased peptoid combinatorial cell screen identifies plectin protein as a potential biomarker for lung cancer stem cells," Sci Rep., 9:14954 (2019); doi:10.1038/s41598-019-51004-3, 15 pages.
Reynolds, F. et al., "A Functional Proteomic Method for Biomarker Discovery," PLoS ONE, 6(7):e22471 (2011), 9 pages.
Romero, I. & Bast, Jr., R. C., "Minireview: Human Ovarian Cancer: Biology, Current Management, and Paths to Personalizing Therapy," Endocrinology, 153:1593-1602 (2012); doi:10.1210/en.2011-2123.
Ross, J. S. et al., "New Routes to Targeted Therapy of Intrahepatic Cholangiocarcinomas Revealed by Next-Generation Sequencing," The Oncologist, 19:235-242 (2014).
Ryman, J. T. & Meibohm, B., "Pharmacokinetics of Monoclonal Antibodies," CPT Pharmacomet Syst Pharmacol., 6:576-588 (2017).
Samudrala et al., "Ab Initio Protein Structure Prediction Using a Combined Hierarchical Approach," Proteins, Structure, Function and Genetics Suppl., 3:194-198 (1999).
Sanna, V. et al., "Targeted Nanoparticles for the Delivery of Novel Bioactive Molecules to Pancreatic Cancer Cells," J Med Chem., 59:5209-5220 (2016).
Seo, J.-M. et al., "Leukotriene B4 Receptor-2 Promotes Invasiveness and Metastasis of Ovarian Cancer Cells through Signal Transducer and Activator of Transcription 3 (STAT3)-Dependent Up-Regulation of Matrix Metalloproteinase 2," J. Biol. Chem., 287:13840-13849 (2012); doi:10.1074/jbc.M111.317131.
Seymour, L. et al., "iRECIST: guidelines for response criteria for use in trials testing immunotherapeutics," Lancet Oncol., 18(3):e143-e152 (2017); doi: 10.1016/S1470-2045(17)30074-8. Epub Mar. 2, 2017.
Shields, R. L., et al., "High resolution mapping of the binding site on human IgG1 for FcγRI, FcγRII, FcγRIII, and FcRn and design of IgG1 variants with improved binding to the FcγR", Journal of Biological Chemistry (2001); 276(9): 6591-6604.
Sievers, F. et al., "Fast, scalable generation of high-quality protein multiple sequence alignments using Clustal Omega," Molecular Systems Biology 7:539 (2011); doi:10.1038/msb.2011.75, 6 pages.
Songsvilai, S., et al., "Bispecific antibody: a tool for diagnosis and treatment of disease.," Clin. Exp. Immunol. 79:315-321 (1990).
Spiekermann, G. M. et al., "Receptor-mediated Immunoglobulin G Transport Across Mucosal Barriers in Adult Life: Functional Expression of FcRn in the Mammalian Lung," J. Exp. Med., 196(3):303-310 (2002).
Studnicka, G. M. et al., "Human-engineered monoclonal antibodies retain full specific binding activity by preserving non-CDR complementarity-modulating residues," Protein Engineering, 7(6):805-814 (1994).
Tai, Y.-T. et al., "Potent in vitro and in vivo activity of an Fc-engineered humanized anti-HM1.24 antibody against multiple myeloma via augmented effector function," Blood, 119(9):2074-2082 (2012).
Torre, L. A. et al., "Global Cancer Statistics," CA. Cancer J. Clin., 65:87-108 (2015); doi:10.3322/caac.21262.
Tsujikawa, T. et al., "Quantitative Multiplex Immunohistochemistry Reveals Myeloid-Inflamed Tumor-Immune Complexity Associated with Poor Prognosis," Cell Rep., 19(1):203-217 (2017).
Valle, J. et al., "Cisplatin plus Gemcitabine versus Gemcitabine for Biliary Tract Cancer," The New England Journal of Medicine, 362:1273-1281 (2010); dx.doi.org/101056/NEJMoa0908721.
Vichai, V. & Kirtikara, K., "Sulforhodamine B Colorimetric Assay for Cytotoxicity Screening," Nat. Protoc., 1(3):1112-1116 (2006), doi:10.1038/nprot.2006.179.
Wang, X. et al., "Surface engineered antifouling optomagnetic SPIONs for bimodal targeted imaging of pancreatic cancer cells," Int J Nanomedicine, 9:1601-1615 (2014).
Weissleder, R., "A clearer vision for in vitro imaging," Nature Biotechnology, 19:316-317 (2001).
Wernitznig, D. et al., "Plecstatin-1 induces an immunogenic cell death signature in colorectal tumour spheroids," Metallomics, 12:2121-2133 (2020).
Wesley, T. et al., "The Attributes of Plakins in Cancer and Disease: Perspectives on Ovarian Cancer Progression, Chemoresistance and Recurrence," Cell Commun. Signal., 19:55 (2021); doi:10.1186/s12964-021-00726-x, 21 pages.
Wu, C.-J. et al., "Activation of STAT3 and STAT5 Signaling in Epithelial Ovarian Cancer Progression: Mechanism and Therapeutic Opportunity," Cancers, 12:24 (2020); doi:10.3390/cancers12010024, 26 pages.
Wu, Y. et al., "Chimeric peptide supramolecular nanoparticles for plectin-1 targeted miRNA-9 delivery in pancreatic cancer," Theranostics, 10(3):1151-1165 (2020).
Yamada, T. et al., "Growth dependency of a new human pancreatic cancer cell line, YAPC, on autocrine interleukin-1alpha stimulation," Int J Cancer, 76(1):141-147 (1998).
Yamamoto, M. et al., "Recurrence after surgical resection of intrahepatic cholangiocarcinoma," J Hepatobiliary Pancreat Surg., 8:154-157 (2001).
Ye, X. et al., "Comparative Proteomics of a Model MCF10A-KRasG12V Cell Line Reveals a Distinct Molecular Signature of the KRasG12V Cell Surface," Oncotarget, 7(52):86948-86971 (2016); doi:10.18632/oncotarget.13566.
Yoneyama, M. S. et al., "Vimentin intermediate filament and plectin provide a scaffold for invadopodia, facilitating cancer cell invasion and extravasation for metastasis," European Journal of Cell Biology, 93:157-169 (2014).
Yuan, Y. et al., "Chaperonin-GroEL as a Smart Hydrophobic Drug Delivery and Tumor Targeting Molecular Machine for Tumor Therapy," Nano Lett., 18:921-928 (2018).
Yue, P. et al., "Hyperactive EGF Receptor, Jaks and Stat3 Signaling Promote Enhanced Colony-Forming Ability, Motility and Migration of Cisplatin-Resistant Ovarian Cancer Cells," Oncogene, 31:2309-2322 (2012); doi:10.1038/onc.2011.409.
Zhong, Y. et al., "Triptolide Inhibits JAK2/STAT3 Signaling and Induces Lethal Autophagy through ROS Generation in Cisplatin-resistant SKOV3/DDP Ovarian Cancer Cells," Oncol. Rep., 45: 69 (2021); doi:10.3892/or.2021.8020, 10 pages.

* cited by examiner

FIG. 4B

PLECTIN-1 BINDING ANTIBODIES AND USES THEREOF

RELATED APPLICATIONS

This application is a continuation-in-part of, and claims priority under 35 U.S.C. § 120 to, international PCT Application No. PCT/US2018/055438, filed Oct. 11, 2018, entitled "PLECTIN-1 BINDING ANTIBODIES AND USES THEREOF," which claims priority under 35 U.S.C. § 119(e) of the filing date of U.S. provisional Application Ser. No. 62/571,246, filed Oct. 11, 2017, entitled "PLECTIN-1 BINDING ANTIBODIES AND USES THEREOF," the entire contents of each of which are incorporated herein by reference.

SEQUENCE LISTING

The instant application contains a Sequence Listing which has been submitted in ASCII format via EFS Web and is hereby incorporated by reference in its entirety. Said ASCII copy, created on Apr. 10, 2020 is named "ZielBio_70003_CIP_ST25" and is 95,353 bytes in size.

BACKGROUND

Pancreatic ductal adenocarcinoma (PDAC) is the 4th leading cause of cancer death in the United States showing a rapid clinical course leading to death. Once diagnosed, PDAC has a median survival of 6 months and a 5-year survival rate of only 3 percent (Li et al., Lancet 363:1049-1057 (2004)).

As chemotherapy and radiotherapy have only modest benefits, and surgery is only possible in 20% of patients, early detection that allows surgical resection offers the best hope for longer survival (Yeo et al., Ann Surg 222:580-588 (1995); discussion 588-592). Indeed, the detection and treatment of PDAC or high-grade precursors in high-risk patient groups (e.g., hereditary cancer syndromes, chronic pancreatitis, and new-onset diabetes) represents a critical unmet need in the cancer diagnostic portfolio (Brentnall et al., Ann. Intern. Med. 131:247-255 (1999); Canto et al., Clin. Gastroenterol. Hepatol. 2:606-621 (2004)).

SUMMARY

In some aspects, the disclosure relates to compositions and methods useful for treating certain cancers (e.g., pancreatic cancer, ovarian cancer, etc.). The disclosure is based, in part, on combinations of anti-plectin-1 antibodies and anti-cancer agents (e.g., small molecules, such as gemcitabine, pyrrolobenzodiazepines (PBDs), etc.), administered as a single composition or separately, that act together (e.g., synergistically) to inhibit cancer cell growth. In some embodiments, the combinations are formulated to produce an antibody-drug-conjugate (ADC).

Aspects of the disclosure are based on plectin-1 antibodies that specifically bind to plectin-1 exposed on the surface of a cell (e.g., a cancer cell). Thus in some aspects, the disclosure provides a composition comprising: an antibody that specifically binds to plectin-1 exposed on the surface of a cancer cell; and one or more anti-cancer agents, wherein the antibody and the anticancer agents are not linked.

In some aspects, the disclosure provides a composition comprising an antibody or antigen binding fragment that specifically binds an amino acid sequence having at least 85% identity to SEQ ID NO: 2 (e.g., an amino acid sequence having at least 90%, at least 95%, at least 96%, at least 97% at least 98% or at least 99% identity to SEQ ID NO: 2); and an anti-cancer agent, wherein the antibody and the anti-cancer agent are not linked. In some embodiments, an anti-plectin-1 antibody and the anti-cancer agent act synergistically (e.g., as measured by the Chou-Talalay method).

In some embodiments, an antibody or antigen binding fragment comprises a heavy chain variable region having a sequence set forth as: SEQ ID NO: 23 or SEQ ID NO: 67. In some embodiments, an antibody or antigen binding fragment comprises a light chain variable region having a sequence set forth as: SEQ ID NO: 45 or SEQ ID NO: 89.

In some embodiments, an antibody comprises a heavy chain variable region having a sequence set forth as: SEQ ID NO 23 and a light chain variable region having a sequence set forth as: SEQ ID NO: 45.

In some embodiments, an antibody comprises a heavy chain variable region having a sequence set forth as: SEQ ID NO 67 and a light chain variable region having a sequence set forth as: SEQ ID NO: 89.

In some embodiments, an antibody or antigen binding fragment binds to cell-surface exposed plectin-1 (e.g., plectin-1 expressed on the surface of a cell, for example a cancer cell).

In some embodiments, an anti-cancer agent is selected from the group consisting of Abraxane® (Paclitaxel Albumin-stabilized Nanoparticle Formulation), Adrucil® (Fluorouracil), Afinitor® (Everolimus), Efudex® (Fluorouracil), Erlotinib Hydrochloride, Everolimus, Fluoroplex® (Fluorouracil), Fluorouracil, Gemcitabine Hydrochloride, Gemzar® (Gemcitabine Hydrochloride), Mitomycin C, Mitozytrex™ (Mitomycin C), Mutamycin® (Mitomycin C), Paclitaxel Albumin-stabilized Nanoparticle Formulation, Sunitinib Malate, Sutent® (Sunitinib Malate), and Tarceva® (Erlotinib Hydrochloride), Altretamine®, Alkeran® (Melphalan), Avastin® (Bevacizumab), Bevacizumab, Carboplatin, Cisplatin, Cyclophosphamide, Cytoxan® (Cyclophosphamide), Doxorubicin Hydrochloride, Dox-SL™ (Doxorubicin Hydrochloride Liposome), DOXIL® (Doxorubicin Hydrochloride Liposome), Doxorubicin Hydrochloride Liposome, Evacet™ (Doxorubicin Hydrochloride Liposome), Hycamtin® (Topotecan Hydrochloride), LipoDox® (Doxorubicin Hydrochloride Liposome), Lynparza® (Olaparib), Melphalan, Neosar® (Cyclophosphamide), Niraparib Tosylate Monohydrate, Olaparib, Paclitaxel, Paraplat (Carboplatin), Paraplatin® (Carboplatin), Platinol® (Cisplatin), Platinol-AQ® (Cisplatin), Rubraca® (Rucaparib Camsylate), Rucaparib Camsylate, Taxol® (Paclitaxel), Thiotepa, Topotecan Hydrochloride, and Zejula™ (Niraparib Tosylate Monohydrate). In some embodiments, the anti-cancer agent is gemcitabine (gem) or cisplatin.

In some aspects, the disclosure provides an antibody-drug-conjugate (ADC) comprising an antibody or antigen binding fragment that specifically binds to plectin-1 exposed on the surface of a cell (e.g., a cancer cell) linked to one or more anti-cancer agent molecules (e.g., between 2 and 100 anti-cancer agent molecules).

In some aspects, the disclosure provides an antibody-drug-conjugate (ADC) comprising an antibody or antigen binding fragment that specifically binds an amino acid sequence having at least 85% identity to SEQ ID NO: 2 (e.g., an amino acid sequence having at least 90%, at least 95%, at least 96%, at least 97% at least 98% or at least 99% identity to SEQ ID NO: 2) linked to one or more anti-cancer agent molecules (e.g., between 2 and 100 anti-cancer agent molecules).

In some embodiments, one or more anti-cancer agent molecules are directly linked to an antibody or antigen binding fragment.

In some embodiments, one or more anti-cancer agent molecules are indirectly linked to the antibody or antigen binding fragment via a linker, for example a photolinker or a flexible amino acid sequence linker.

In some embodiments, 2, 3, 4, or 5 anti-cancer agent molecules are linked to an antibody or antigen binding fragment.

In some embodiments, an anti-cancer agent molecule is auristatin or pyrrolobenzodiazepine (PBD). In some embodiments, a PBD molecule is a PBD dimer.

In some aspects, the disclosure provides a method for treating cancer, the method comprising administering to a subject having cancer an effective amount of an antibody or antigen binding fragment that specifically binds an amino acid sequence having at least 85% identity to SEQ ID NO: 2, and an anti-cancer agent. In some embodiments, the subject is a mammal, for example a human.

In some embodiments of methods described by the disclosure, an antibody or antigen binding fragment and an anti-cancer agent are administered together (e.g., as a composition or ADC as described herein). In some embodiments, an antibody or antigen binding fragment and an anti-cancer agent are administered separately to a subject.

In some embodiments, a cancer is characterized by expression of plectin-1 on the surface of the cancer cell. In some embodiments, a cancer is ovarian cancer, esophageal cancer, head and neck squamous cell carcinoma, or pancreatic cancer. In some embodiments, the pancreatic cancer is pancreatic ductal adenocarcinoma (PDAC).

In some embodiments of methods described by the disclosure, an antibody, anti-cancer agent, ADC, or composition is administered at a dose in a range of 1 ng/kg and 100 mg/kg.

BRIEF DESCRIPTION OF DRAWINGS

FIG. 2A shows treatment of cells with anti-plec1 results in G0 and G2 growth arrest. FIG. 2B shows representative data for EC50 of anti-plec1 for YapC cells. FIG. 2C shows the phenotypic effect of anti-plec1 treatment on YapC microtubule (top, left to right) and actin microfilaments (bottom, left to right).

FIG. 4B shows images of tumors from mice bearing OVCAR8 tumors treated with ZB131 alone or in combination with cisplatin.

DETAILED DESCRIPTION

Figure 1A:
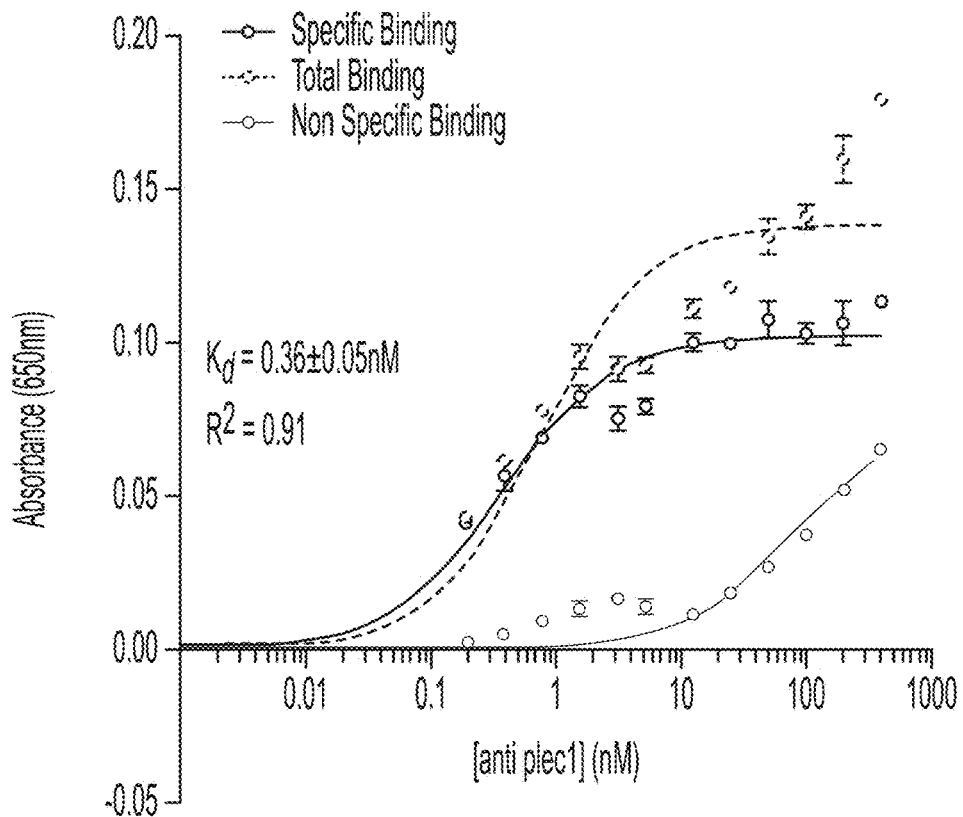
FIGS. 1A-1B show representative data for affinity and specificity of an anti-plec1 antibody on human recombinant protein (FIG. 1A) and human (YapC and L3.6pl) and mouse (Han14.3) pancreatic cell lines (FIG. 1B).

The disclosure relates, in some aspects, to compositions and methods for treatment of certain cancers (e.g., cancers characterized by surface expression of plectin-1). Plectin-1 is a useful biomarker for a variety of cancers, including ovarian, esophageal, and head and neck squamous cells carcinomas, as well as pancreatic ductal adenocarcinoma. In contrast with antibody targets, such as CD30, which is targeted by Brentuximab vedotin, and Her2, which is targeted by Ado-trastuzumab Emtansine, plectin-1 is a particularly useful target because it is present on the cell surface exclusively in certain cancer cells (e.g., pancreatic ductal adenocarcinoma cells, ovarian cancer cells, etc.), thus giving exquisite specificity and selectivity. Accordingly, in some embodiments, the disclosure relates to antibodies and antigen binding fragments that bind specifically to plectin-1 on the surface of cancer cells, and methods of use thereof. In some embodiments, binding of an anti-plectin-1 antibody as described by the disclosure to a plectin-1 expressing cell induces death (e.g., triggers apoptosis) of the cell.

The disclosure is based, in part, on the recognition that certain combinations of anti-plectin-1 antibodies and anti-cancer agents are capable of mediating enhanced inhibition of cancer cell growth when delivered together, either as separate compositions or as a single composition (e.g., a composition comprising an anti-plectin-1 antibody and an anti-cancer agent, or an ADC as described herein).

Antibodies that Bind Plectin-1

The present disclosure provides compositions (e.g., ADCs) comprising antibodies and antigen binding fragments that bind to plectin-1 on the surface of cancer cells. The monoclonal antibodies of the disclosure may be murine, humanized or chimeric or in other forms. A detailed description of the antibodies of the disclosure is provided herein.

Plectin-1 is a high molecular weight protein (500 kDa) that links intermediate filaments to microtubules and microfilaments, in addition to anchoring the cytoskeleton the plasma and nuclear membranes (reviewed in Sonnenberg, et al., *Exp Cell Res* 313:2189-2203 (2007)).

Generally, plectin-1 levels are low in normal pancreatic ductal cells but its expression is upregulated in cells having certain cancers (e.g., precursor pancreatic intraepithelial neoplasia (PanINs), pancreatic ductal adenocarcinoma cells (PDACs), ovarian cancer cells, etc.). Plectin-1 exhibits distinct cytoplasm and nuclear localization in normal fibroblasts, whereas an aberrant expression on the cell membrane is observed in cells having certain cancers (e.g., PDACs). Altered subcellular localization of plectin-1 has also been observed in an autoimmune condition, paraneoplastic pemphigus, and in the associated lymphoproliferative neoplasm, Castleman's disease (Aho et al., *J Invest Dermatol* 113:422-423 (1999)). Plectin-1 also has important roles in signal transduction. Thus, plectin-1 in cells having certain cancers (e.g., precursor pancreatic intraepithelial neoplasia (PanINs), pancreatic ductal adenocarcinoma cells (PDACs), ovarian cancer cells, etc.) may have an impact on signaling pathways that regulate cell migration, polarity and energy metabolism related to carcinogenesis. Accordingly, in some embodiments, the disclosure provides antibodies and antigen binding fragments that bind to plectin-1 on the surface of cancer cells.

In some embodiments, antibodies, also known as immunoglobulins, are tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., IgG$_1$, IgG$_2$, IgG$_3$, IgG$_4$, IgA$_1$, and IgA$_2$. Each light chain typically includes an N-terminal variable (V) domain (V$_L$) and a constant (C) domain (C$_L$). Each heavy chain typically includes an N-terminal V domain (V$_H$), three or four C domains (C$_H$1-3), and a hinge region. The C$_H$ domain most proximal to V$_H$ is designated as C$_H$1. The V$_H$ and V$_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) *J. Mol. Biol.* 227:799-817; and Tomlinson et al. (1995) *EMBO J.* 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

Examples of anti-plectin-1 antibodies of the present disclosure include, but are not limited to, Pab1 and Pab2 (which are also referred to as anti-plec1). In some embodiments, anti-plectin-1 antibodies of the present disclosure and the nucleic acid molecules of the present disclosure that encode the antibodies include the CDR amino acid and nucleic acid sequences shown in Table 1 below.

TABLE 1

| Antibody | CDRH1 | CDRH2 | CDRH3 | CDRL1 | CDRL2 | CDRL3 |
|---|---|---|---|---|---|---|
| Pab2 | | | | | | |
| Amino acid: | (SEQ ID NO: 17) | (SEQ ID NO: 19) | (SEQ ID NO: 21) | (SEQ ID NO: 39) | (SEQ ID NO: 41) | (SEQ ID NO: 43) |
| Nuc. Acid: | (SEQ ID NO: 6) | (SEQ ID NO: 8) | (SEQ ID NO: 10) | (SEQ ID NO: 28) | (SEQ ID NO: 30) | (SEQ ID NO: 32) |
| Pab1 | | | | | | |
| Amino acid: | (SEQ ID NO: 61) | (SEQ ID NO: 63) | (SEQ ID NO: 65) | (SEQ ID NO: 83) | (SEQ ID NO: 85) | (SEQ ID NO: 87) |
| Nuc. Acid: | (SEQ ID NO: 50) | (SEQ ID NO: 52) | (SEQ ID NO: 54) | (SEQ ID NO: 72) | (SEQ ID NO: 74) | (SEQ ID NO: 76) |

In some embodiments, anti-plectin-1 binding agents (e.g., anti-plectin-1 antibodies) of the disclosure include any antibody or antigen binding fragment that includes a CDRH1, CDRH2, CDRH3, CDRL1, CDRL2, or CDRL3, or combinations thereof, as provided for any one of the antibodies shown in Table 1. In some embodiments, anti-plectin-1 binding agents include the CDRH1, CDRH2, CDRH3, CDRL1, CDRL2, and CDRL3 of any one of the antibodies shown in Table 1. The disclosure also includes any nucleic acid sequence that encodes a CDRH1, CDRH2, CDRH3, CDRL1, CDRL2, or CDRL3 as provided for any one of the antibodies shown in Table 1. Antibody heavy and light chain CDR3 domains may play a particularly important role in the binding specificity/affinity of an antibody for an antigen. Accordingly, the anti-plectin-1 antibodies of the disclosure, or the nucleic acid molecules thereof, may include at least the heavy and/or light chain CDR3s of antibodies as shown in Table 1 or as set forth by SEQ ID NOs: 14, 21, 23, 36, 43, 45, 58, 65, 67, 80, 87 or 89.

The complete amino acid and nucleic acid sequences for the heavy chain variable region and light chain variable region of the antibodies listed in Table 2.

TABLE 2

| Antibody | Heavy Chain Variable Region | Light Chain Variable Region |
|---|---|---|
| PAb2 | | |
| Amino acid: | SEQ ID NO: 23 | SEQ ID NO: 45 |
| Nuc. Acid: | SEQ ID NO: 12 | SEQ ID NO: 34 |
| PAb1 | | |
| Amino acid: | SEQ ID NO: 67 | SEQ ID NO: 89 |
| Nuc. Acid: | SEQ ID NO: 56 | SEQ ID NO: 78 |

In some embodiments, anti-plectin antibodies of the disclosure include any antibody that includes a heavy chain variable domain or a light chain variable domain or both as shown in Table 1, or as described in the sequence listing of this disclosure (e.g., SEQ ID NOs: 14, 23, 36, 45, 58, 67, 80, or 89). The disclosure also includes any nucleic acid molecule encoding an antibody that includes a heavy chain variable domain or a light chain variable domain nucleic acid sequence, or both, as shown in Table 1 or as described in the sequence listing of this disclosure (e.g., SEQ ID NOs: 3, 12, 25, 34, 47, 56, 69, or 78).

Anti-plectin-1 antibodies of this disclosure may optionally comprise antibody constant regions or parts thereof. For example, a V$_L$ domain may be attached at its C-terminal end to a light chain constant domain like Cκ or Cλ. Similarly, a V$_H$ domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include V$_H$ and V$_L$ domains, or an antigen binding portion thereof, combined with constant regions known in the art. In some embodiments, anti-plectin-1 antibodies of the disclosure comprise a heavy chain constant region comprising a sequence represented by SEQ ID NOs: 3, 13, 25, 35, 47, 57, 69, or 79.

In certain embodiments, the V$_H$ and/or V$_L$ domains may be reverted to germline sequence, e.g., the FR of these domains are mutated using conventional molecular biology techniques to match those produced by the germline cells. In other embodiments, the FR sequences remain diverged from the consensus germline sequences.

In some embodiments, anti-plectin-1 antibodies or antigen binding fragments may or may not include the framework region of the antibodies, for example as set forth in SEQ ID NOs: 5, 7, 9, 11, 16, 18, 20, 22, 27, 29, 31, 33, 38, 40, 42, 44, 49, 51, 53, 55, 60, 62, 64, 66, 71, 73, 75, 77, 82, or 84. In some embodiments, anti-plectin-1 antibodies are murine antibodies. In some embodiments, anti-plectin-1 antibodies are chimeric or humanized antibodies.

It should be appreciated that, in some embodiments, the disclosure contemplates variants (e.g., homologs) of amino acid and nucleic acid sequences for the heavy chain variable region and light chain variable region of the antibodies. "Homology" refers to the percent identity between two polynucleotides or two polypeptide moieties. The term "substantial homology", when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences. For example, in some embodiments, nucleic acid sequences sharing substantial homology are at least 90%, at least 91%, at least 92% at least 93%, at least 94%, at least 95%, at least 96% at least 97%, at least 98% at least 99% sequence identity. When referring to a polypeptide, or fragment thereof, the term "substantial homology" indicates that, when optimally aligned with appropriate gaps, insertions or deletions with another polypeptide, there is nucleotide sequence identity in about 90 to 100% of the aligned sequences. The term "highly conserved" means at least 80% identity, preferably at least 90% identity, and more preferably, over 97% identity. For example, in some embodiments, highly conserved proteins share at least 85%, at least 90%, at least 91%, at least 92% at least 93%, at least 94%, at least 95%, at least 96% at least 97%, at least 98% at least 99% identity. In some cases, highly conserved may refer to 100% identity. Identity is readily determined by one of skill in the art by, for example, the use of algorithms and computer programs known by those of skill in the art.

In some embodiments, an anti-plectin-1 antibodies of the disclosure can bind to plectin-1 with high affinity, e.g., with a Kd less than $10^{-7}$ M, $10^{-8}$ M, $10^{-9}$ M, $10^{-10}$ M, $10^{-11}$ or lower. For example, anti-plectin-1 antibodies or antigen binding fragments thereof can bind to plectin-1 with an affinity between 5 pM and 500 nM, e.g., between 50 pM and 100 nM, e.g., between 500 pM and 50 nM. The disclosure also includes antibodies or antigen binding fragments that compete with any of the antibodies described herein for binding to plectin-1 and that have an affinity of 50 nM or lower (e.g., 20 nM or lower, 10 nM or lower, 500 pM or lower, 50 pM or lower, or 5 pM or lower). The affinity and binding kinetics of the anti-plectin-1 antibody can be tested using any method known in the art including but not limited to biosensor technology (e.g., OCTET or BIACORE).

As used herein, the term "antibody" generally refers to an immunoglobulin. All derivatives thereof which maintain or possess specific binding ability are also provided herein. An antibody preparation may be monoclonal or polyclonal.

As used herein, the term "antibody fragment" or "antigen binding fragment" refers to any derivative of an antibody which is less than full-length. Generally, an antigen binding fragment retains at least a significant portion of the full-length antibody's specific binding ability. Examples of antigen binding fragments include, but are not limited to, Fab, Fab', F(ab')2, scFv, Fv, dsFv diabody, affibodies, and Fd fragments. Antigen binding fragments may be produced by any appropriate means. For instance, an antigen binding fragment may be enzymatically or chemically produced by fragmentation of an intact antibody or it may be recombinantly produced from a gene encoding the partial antibody sequence. Alternatively, an antigen binding fragment may be wholly or partially synthetically produced. An antigen binding fragment may optionally be a single chain antibody fragment. Alternatively, a fragment may comprise multiple chains which are linked together, for instance, by disulfide linkages. An antigen binding fragment may also optionally be a multimolecular complex. A functional antigen binding fragment will typically comprise at least about 50 amino acids and more typically will comprise at least about 200 amino acids.

Single-chain Fvs (scFvs) are recombinant antigen binding fragments consisting of only the variable light chain (VL) and variable heavy chain (VH) covalently connected to one another by a polypeptide linker. Either VL or VH may be the NH2-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

Diabodies are dimeric scFvs. The components of diabodies typically have shorter peptide linkers than most scFvs, and they show a preference for associating as dimers.

A Fv fragment is an antigen binding fragment which consists of one VH and one VL domain held together by noncovalent interactions. The term dsFv is used herein to refer to an Fv with an engineered intermolecular disulfide bond to stabilize the VH-VL pair.

A F(ab')2 fragment is an antigen binding fragment essentially equivalent to that obtained from immunoglobulins (typically IgG) by digestion with an enzyme pepsin at pH 4.0-4.5. The fragment may be recombinantly produced.

A Fab fragment is an antigen binding fragment essentially equivalent to that obtained by reduction of the disulfide bridge or bridges joining the two heavy chain pieces in the F(ab')2 fragment. The Fab' fragment may be recombinantly produced.

A Fab fragment is an antigen binding fragment essentially equivalent to that obtained by digestion of immunoglobulins (typically IgG) with the enzyme papain. The Fab fragment may be recombinantly produced. The heavy chain segment of the Fab fragment is the Fd piece. An affibody is a small protein comprising a three-helix bundle that functions as an antigen binding molecule (e.g., an antibody mimetic). Generally, affibodies are approximately 58 amino acids in length and have a molar mass of approximately 6 kDa. Affibody molecules with unique binding properties are acquired by randomization of 13 amino acids located in two alpha-helices involved in the binding activity of the parent protein domain. Specific affibody molecules binding a desired target protein can be isolated from pools (libraries) containing billions of different variants, using methods such as phage display.

Antibody-Drug Conjugates (ADCs)

Some aspects of the disclosure relate to antibody-drug conjugates targeted against plectin-1. As used herein, "antibody drug conjugate" or "ADC" refers to molecules comprising an antibody, or antigen binding fragment thereof, linked to one or more targeted molecules (e.g., a biologically active molecule, such as a therapeutic molecule, and/or a detectable label). Accordingly, in some embodiments, antibodies or antigen binding fragments of the disclosure may be modified with a therapeutic agent. As used herein, the term "therapeutic agent" refers to chemicals or drugs or proteins that are able to inhibit cell function, inhibit cell replication or kill mammalian cells, preferably human cells, more preferably human cancer cells. Examples of therapeutic agents include but are not limited to cytotoxic moieties, radioisotopes, molecules of plant, fungal, or bacterial origin (e.g., plant-derived toxins (e.g., secondary metabolites), glycosides, antimicrobial compounds (e.g., streptomycin, penicillin, etc.), biological proteins (e.g., protein toxins), particles (e.g., recombinant viral particles, e.g., via a viral coat protein)), or mixtures thereof. The therapeutic agent can be an intracellularly active drug or other agent, such as short-range radiation emitters, including, for example, short-range, high-energy alpha-emitters (e. g., $^{131}$I).

In some embodiments, a therapeutic agent is an anti-cancer agent. The term "anti-cancer agent" refers to chemicals or drugs or proteins that are able to inhibit cancer cell function, inhibit cancer cell growth or replication, or kill cancer cells. In some embodiments, an anti-cancer agent is a chemical or drug or protein that is approved by the U.S. Food and Drug Administration (FDA) for treatment of cancer. Examples of anti-cancer agents include but are not limited to Abraxane® (Paclitaxel Albumin-stabilized Nanoparticle Formulation), Adrucil® (Fluorouracil), Afinitor® (Everolimus), Efudex® (Fluorouracil), Erlotinib Hydrochloride, Everolimus, Fluoroplex® (Fluorouracil), Fluorouracil, Gemcitabine Hydrochloride, Gemzar® (Gemcitabine Hydrochloride), Mitomycin C, Mitozytrex™ (Mitomycin C), Mutamycin® (Mitomycin C), Paclitaxel Albumin-stabilized Nanoparticle Formulation, Sunitinib Malate, Sutent® (Sunitinib Malate), and Tarceva® (Erlotinib Hydrochloride), Altretamine®, Alkeran® (Melphalan), Avastin® (Bevacizumab), Bevacizumab, Carboplatin, Cisplatin, Cyclophosphamide, Cytoxan® (Cyclophosphamide), Doxorubicin Hydrochloride, Dox-SL™ (Doxorubicin Hydrochloride Liposome), DOXIL® (Doxorubicin Hydrochloride Liposome), Doxorubicin Hydrochloride Liposome, Evacet™ (Doxorubicin Hydrochloride Liposome), Hycamtin® (Topotecan Hydrochloride), LipoDox® (Doxorubicin Hydrochloride Liposome), Lynparza® (Olaparib), Melphalan, Neosar® (Cyclophosphamide), Niraparib Tosylate Monohydrate, Olaparib, Paclitaxel, Paraplat (Carboplatin), Paraplatin® (Carboplatin), Platinol® (Cisplatin), Platinol-AQ® (Cisplatin), Rubraca® (Rucaparib Camsylate), Rucaparib Camsylate, Taxol® (Paclitaxel), Thiotepa, Topotecan Hydrochloride, and Zejula™ (Niraparib Tosylate Monohydrate). In some embodiments, the anti-cancer agent is gemcitabine (gem) or cisplatin.

In some embodiments, an anti-cancer agent is a pyrrolobenzodiazepine (PBD). Generally, PDBs are a class of dimerized crosslinking agents that bind to the DNA minor-groove in a sequence-specific manner, for example as described by Antonow D et al. (2011) *Chem Rev* 111: 2815-2864; Cipolla et al. (2009) *Anticancer Agents Med Chem* 9: 1-31; and Gerratana (2012) *Med Res Rev* 32: 254-293.

In some embodiments, the therapeutic agent (e.g., anti-cancer agent) is an immunomodulatory moiety (e.g., immunomodulatory agent). As used herein, "immunomodulatory agent" refers to a compound or molecule that increases or decreases the immune response of a subject in response to the agent. For example, an immunomodulatory agent may enhance the immune response of a subject to a tumor, e.g., increase the level of inflammatory cytokines such as interleukin-1 (IL-1), and tumor necrosis factor-alpha (TNF-α). Examples of immunomodulatory agents that increase the immune response of a subject include granulocyte colony-stimulating factor (G-CSF), interferons, imiquimod, cellular membrane fractions from bacteria, certain interleukins and cytokines (e.g., IL-1β, IL-6, and TNF-α), and immune checkpoint inhibitors (e.g., PD-1 inhibitors, PD1-L inhibitors, etc.). In some embodiments, an immunomodulatory agent may decrease the immune response of a subject (e.g., mediate or achieve immunosuppression). Examples of immunosuppressive immunomodulators include but are not limited to immunosuppressive drugs (e.g., glucococorticoids, cytostatics, anti-inflammatory monoclonal antibodies (e.g., anti-IL-2 receptor antibodies)), and drugs targeting immunophilins (e.g., ciclosporin, sirolimus, etc.).

One or more therapeutic agents (e.g., anti-cancer agent) may be coupled or conjugated either directly to the anti-plectin-1 antibodies of the disclosure or indirectly, through an intermediate (such as, for example, a linker known in the art) using techniques known in the art. In some embodiments, multiple (e.g., 2, 3, 4, 5, 6, 7, 8, 9, 10, or more) therapeutic agents (e.g., anti-cancer agent molecules) are coupled or conjugated to an anti-plectin-1 antibody. For example, in some embodiments, an ADC comprises 1, 2, 3, 4, or 5 PDB molecules (e.g., PDB dimers, trimers, etc.) conjugated to an anti-plectin-1 antibody.

In some embodiments, the antibody is coupled to the targeted agent via a linker. As used herein, the term "linker" refers to a molecule or sequence, such as an amino acid sequence, that attaches, as in a bridge, one molecule or sequence to another molecule or sequence. "Linked," "conjugated," or "coupled" means attached or bound by covalent bonds, or non-covalent bonds, or other bonds, such as van der Waals forces. Antibodies described by the disclosure can be linked to the targeted agent (e.g., therapeutic moiety or detectable moiety) directly, e.g., as a fusion protein with protein or peptide detectable moieties (with or without an optional linking sequence, e.g., a flexible linker sequence) or via a chemical coupling moiety. A number of such coupling moieties are known in the art, e.g., a peptide linker or a chemical linker, e.g., as described in International Patent Application Publication No. WO 2009/036092. In some embodiments, the linker is a flexible amino acid sequence. Examples of flexible amino acid sequences include glycine and serine rich linkers, which comprise a stretch of two or more glycine residues, (e.g., GGGS; SEQ ID NO: 91). In some embodiments, the linker is a photolinker. Examples of photolinkers include ketyl-reactive benzophenone (BP), anthraquinone (AQ), nitrene-reactive nitrophenyl azide (NPA), and carbene-reactive phenyl-(trifluoromethyl)diazirine (PTD).

Pharmaceutical Compositions

In some aspects, the disclosure relates to pharmaceutical compositions comprising anti-plectin-1 antibodies (e.g., ADCs comprising anti-plectin-1 antibodies). In some embodiments, the composition comprises an anti-plectin-1 antibody, an anti-cancer agent, and a pharmaceutically acceptable carrier. The ratio (e.g., concentration ratio) of anti-plectin-1 antibody to anti-cancer agent in a composition of the disclosure can vary. In some embodiments, the ratio of anti-plectin-1 antibody to anti-cancer agent ranges from about 1:100 to about 100:1, for example any ratio therebetween. In some embodiments, the ratio (e.g., concentration ratio) of anti-plectin-1 antibody to anti-cancer agent is about 1:1.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

Typically, pharmaceutical compositions are formulated for delivering an effective amount of an agent (e.g., a composition comprising an anti-plectin-1 antibody, or antibody drug conjugate comprising an anti-plectin-1 antibody and an anti-cancer agent). In general, an "effective amount" of an active agent refers to an amount sufficient to elicit the desired biological response (e.g., killing of a cancerous cell or suppression of tumor growth). An effective amount of an agent may vary depending on such factors as the desired biological endpoint, the pharmacokinetics of the compound, the disease being treated (e.g., certain cancers characterized by surface expression of plectin-1), the mode of administration, and the patient.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed and which is inert with respect to the active agent may be utilized for preparing and administering the pharmaceutical compositions of the present disclosure. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the disclosure, will experience no difficulty in determining suitable and appropriate vehicles, excipients and carriers or in compounding the active ingredients therewith to form the pharmaceutical compositions of the disclosure.

An effective amount, also referred to as a therapeutically effective amount, of a compound (for example, an anti-plectin-1 antibody or antibody drug conjugate comprising an anti-plectin-1 antibody and a targeted agent) is an amount sufficient to ameliorate at least one adverse effect associated with cancer (e.g., tumor growth, metastasis). The therapeutically effective amount to be included in pharmaceutical compositions depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg. One of ordinary skill in the art would be able to determine empirically an appropriate therapeutically effective amount.

Combined with the teachings provided herein, by choosing among the various active compounds and weighing factors such as potency, relative bioavailability, patient body weight, severity of adverse side-effects and selected mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

In some cases, compounds of the disclosure are prepared in a colloidal dispersion system. Colloidal dispersion systems include lipid-based systems including oil-in-water emulsions, micelles, mixed micelles, and liposomes. In some embodiments, a colloidal system of the disclosure is a liposome. Liposomes are artificial membrane vessels which are useful as a delivery vector in vivo or in vitro. It has been shown that large unilamellar vesicles (LUVs), which range in size from 0.2-4.0 μm can encapsulate large macromolecules.

Liposomes may be targeted to a particular tissue by coupling the liposome to a specific ligand such as a monoclonal antibody, sugar, glycolipid, or protein. Ligands which may be useful for targeting a liposome to, for example, an smooth muscle cell include, but are not limited to: intact or fragments of molecules which interact with smooth muscle cell specific receptors and molecules, such as antibodies, which interact with the cell surface markers of cancer cells. Such ligands may easily be identified by binding assays well known to those of skill in the art. In still other embodiments, the liposome may be targeted to a tissue by coupling it to an antibody known in the art.

Compounds described by the disclosure may be administered alone (e.g., in saline or buffer) or using any delivery vehicle known in the art. For instance the following delivery vehicles have been described: cochleates; Emulsomes; ISCOMs; liposomes; live bacterial vectors (e.g., *Salmonella, Escherichia coli, Bacillus Calmette-Guérin, Shigella, Lactobacillus*); live viral vectors (e.g., Vaccinia, adenovirus, Herpes simplex); microspheres; nucleic acid vaccines; polymers (e.g., carboxymethylcellulose, chitosan); polymer rings; proteosomes; sodium fluoride; transgenic plants; virosomes; and, virus-like particles.

The formulations of the disclosure are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In addition to the formulations described herein, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) *Science* 249:1527-1533, which is incorporated herein by reference.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Treatment Methods

Aspects of the disclosure relate to combinations of anti-plectin-1 antibodies and anti-cancer agents, administered as a single composition or separately, that act together (e.g., synergistically) to inhibit growth of certain cancer cells. Methods of measuring synergism are known and are described, for example by Chou (2010) *Cancer Res.* 70(2): 440-6. In some embodiments, a combination of anti-plectin-1 antibody and one or more anti-cancer agents inhibits growth of a cell (e.g., a cancer cell) by between 2-fold and 100-fold (e.g., 2-fold, 4-fold, 5-fold, 10-fold, 20-fold, 25-fold, 50-fold, 75-fold, etc.) more than either the antibody or anti-cancer agent alone. In some embodiments, a combination of anti-plectin-1 antibody and one or more anti-cancer agents inhibits growth of a cell (e.g., a cancer cell) more than 100-fold relative to either the antibody or anti-cancer agent alone.

Without wishing to be bound by any particular theory, compositions and ADCs described by the disclosure are useful, in some embodiments, for treating cancer characterized by surface expression of plectin-1. As used herein, "treating cancer" refers to decreasing the number of cancer cells in a patient, slowing the growth of cancer cells in a patient, reducing the metastasis of cancer cells in a patient and includes any type of response for either relieving cancer symptoms or increasing the life-span of a patient.

Examples of cancers characterized by surface expression of plectin-1 include but are not limited to ovarian cancer cell, esophageal cancer cell, head and neck squamous cell carcinoma cancer cell, or pancreatic cancer cell (e.g., pancreatic ductal adenocarcinoma (PDAC)). However, it should be appreciated that other cancers (such as lung cancer, bladder cancer, breast cancer, esophageal cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, stomach cancer, prostate cancer, testicular cancer, cervical cancer, endometrial cancer, uterine cancer, colon cancer, colorectal, gastric cancer, kidney cancer, bladder cancer, lymphoma cancer, spleen cancer, thymus cancer, thyroid cancer, brain cancer, neuronal cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, white blood cell cancer (e.g., lymphoma, leukemia, etc.), hereditary non-polyposis cancer (HNPC), colitis-associated cancer, etc.) may be characterized by surface expression of plectin-1 and/or treated using compositions and ADCs described by the disclosure. Cancers further exemplified by sarcomas (such as osteosarcoma and Kaposi's sarcoma) may, in some embodiments, be treated using compositions and ADCs described by the disclosure.

In some aspects, the disclosure provides a method for treating cancer, the method comprising administering to a subject having cancer an effective amount of a composition or ADC as described by the disclosure (e.g., a composition or ADC comprising an anti-plectin-1 antibody and an anti-cancer agent). In some embodiments, the subject is a mammal. In some embodiments, the subject is a human.

Generally, antibodies and pharmaceutical compositions of the disclosure preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally.

The pharmaceutical compositions and/or ADCs can be administered by any suitable route for administering medications. A variety of administration routes are available. The particular mode selected will depend, of course, upon the particular agent or agents selected, the particular condition being treated, and the dosage required for therapeutic efficacy. The methods of this disclosure, generally speaking, may be practiced using any mode of administration that is medically acceptable, meaning any mode that produces therapeutic effect without causing clinically unacceptable adverse effects. Various modes of administration are discussed herein. For use in therapy, an effective amount of the anti-plectin-1 antibody and/or other therapeutic agent can be administered to a subject by any mode that delivers the agent to the desired surface, e.g., mucosal, systemic.

Administering the pharmaceutical composition of the present disclosure may be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The compositions and ADCs described by the disclosure can be administered to a subject (e.g., a subject having cancer) on multiple occasions. In some embodiments, the number of occasions in which an antibody or composition of the disclosure is delivered to a subject is in a range of 2 to 10 times (e.g., 2, 3, 4, 5, 6, 7, 8, 9, or 10 times). In some embodiments, an antibody or composition of the disclosure is delivered to a subject more than 10 times.

In some embodiments, a dose of a composition or ADC of the disclosure is administered to a subject no more than once per calendar day (e.g., a 24-hour period). In some embodiments, a dose of a composition or ADC of the disclosure is administered to a subject no more than once per 2, 3, 4, 5, 6, or 7 calendar days. In some embodiments, a dose of a composition or ADC of the disclosure is administered to a subject no more than once per calendar week (e.g., 7 calendar days). In some embodiments, a dose of composition or ADC of the disclosure is administered to a subject no more than bi-weekly (e.g., once in a two calendar week period). In some embodiments, a dose of a composition or ADC of the disclosure is administered to a subject no more than once per calendar month (e.g., once in 30 calendar days). In some embodiments, a dose of a composition or ADC of the disclosure is administered to a subject no more than once per six calendar months. In some embodiments, a dose of a composition or ADC of the disclosure is administered to a subject no more than once per calendar year (e.g., 365 days or 366 days in a leap year).

The present disclosure is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

Cell Assays

PDAC cell survival is assessed using a sulforhodamine B (SRB) protocol. Briefly, cells are seeded in 96-well plate and incubated overnight in the appropriate media. The next day, cells are treated with increasing concentrations of IgG control, anti-plec1, or Gemcitabine (gem). At day 3 post-treatment, the cells are stained with SRB and quantitated using a plate reader set at absorbance 562 nm wavelength ($Abs_{562}$). An additional plate is dedicated to determine the cell number pre-treatment day 0. Percent control growth at each concentration is determined as % of control cell growth=[$meanOD_{sample}$–$meanOD_{day0}$]/[$meanOD_{neg\ control}$–$meanOD_{day0}$]×100. Percent growth inhibition is calculated as follows: % growth inhibition=100–[% of control cell growth].

After the IC50 of anti-plec1, IgG, and gem are determined, an identical cell assay is performed to determine synergy by incubating cells with increasing drug concentrations with an equipotent anti plec1-to-gem ratio (e.g., IC50) that is specific to each cell line.

Determination of Synergy

Synergy is calculated using the Chou-Talalay method (e.g., as described in *Cancer Res.* 2010 Jan. 15; 70(2):440-6) to determine synergetic effect. Combination Index (CI) is then calculated for each treatment concentration tested. CI<1, CI=1, and CI>1 indicate synergism, additive effect, and antagonism, respectively. An example output is provided below, where CI: combination index; D: Dose; Fa=fraction affected; x=Fa.

$$CI = \frac{(D)_1}{(D_x)_1} + \frac{(D)_2}{(D_x)_2}$$

| Fa | CI Value | Total Dose |
|---|---|---|
| 0.9 | 0.10887 | 599.616 |
| 0.95 | 0.07791 | 1243.30 |
| 0.97 | 0.06153 | 2088.90 |

Effects of Anti-Plec1 and Gemcitabine Treatment

Figure 1B:
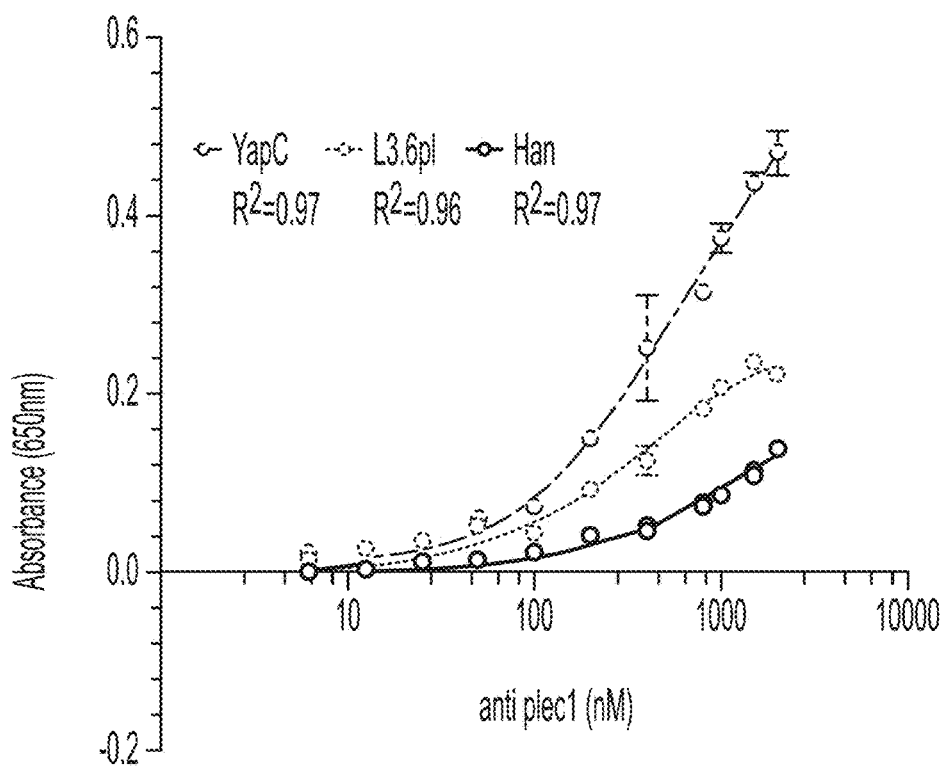
Figure 2A:
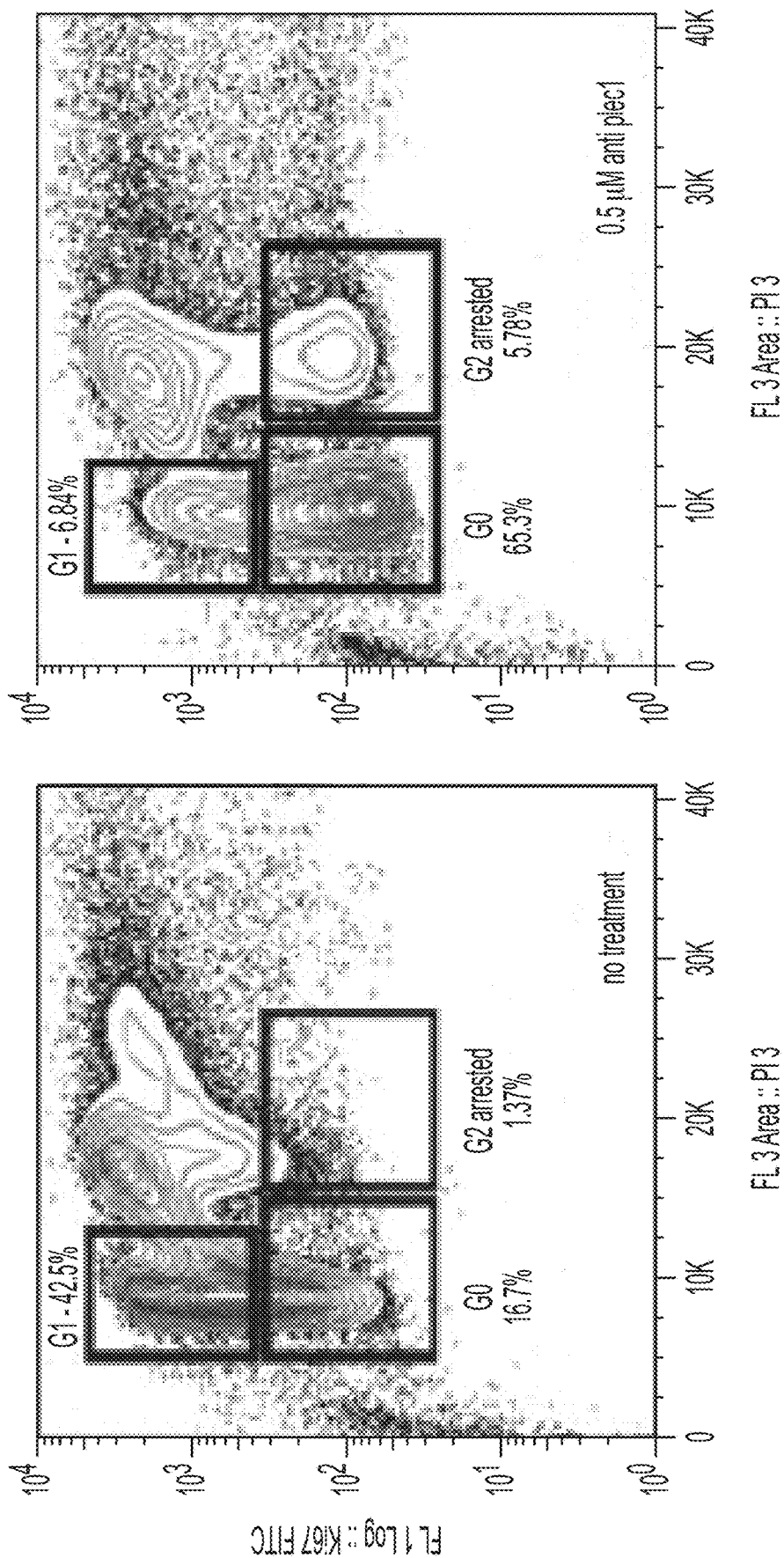
FIGS. 2A-2C show treatment of YapC cells with anti-plec1 antibody.
Figure 2B:
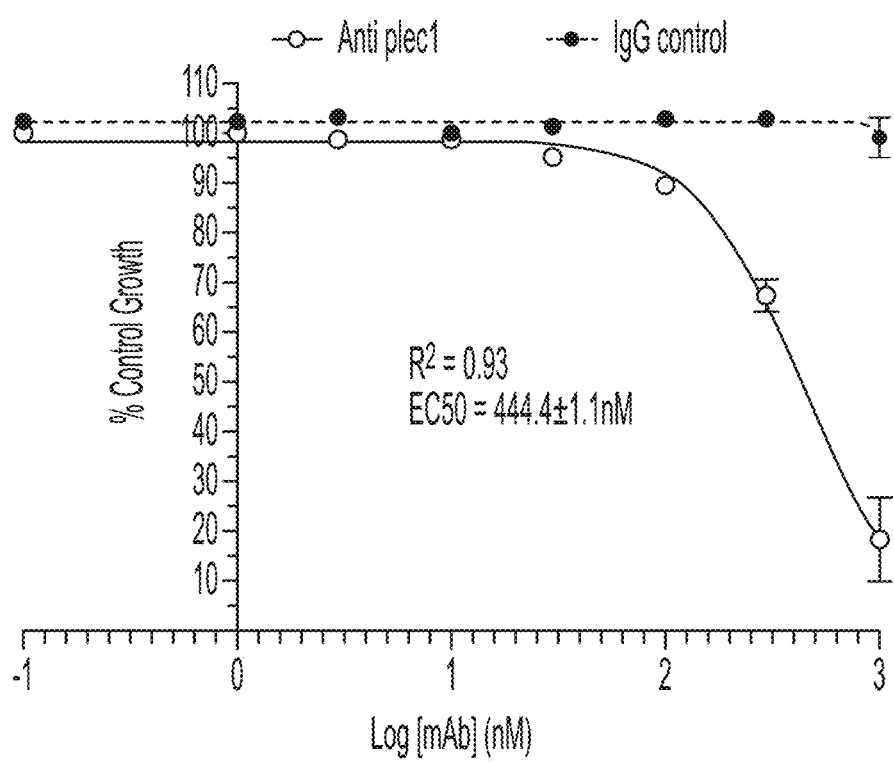
Figure 2C:
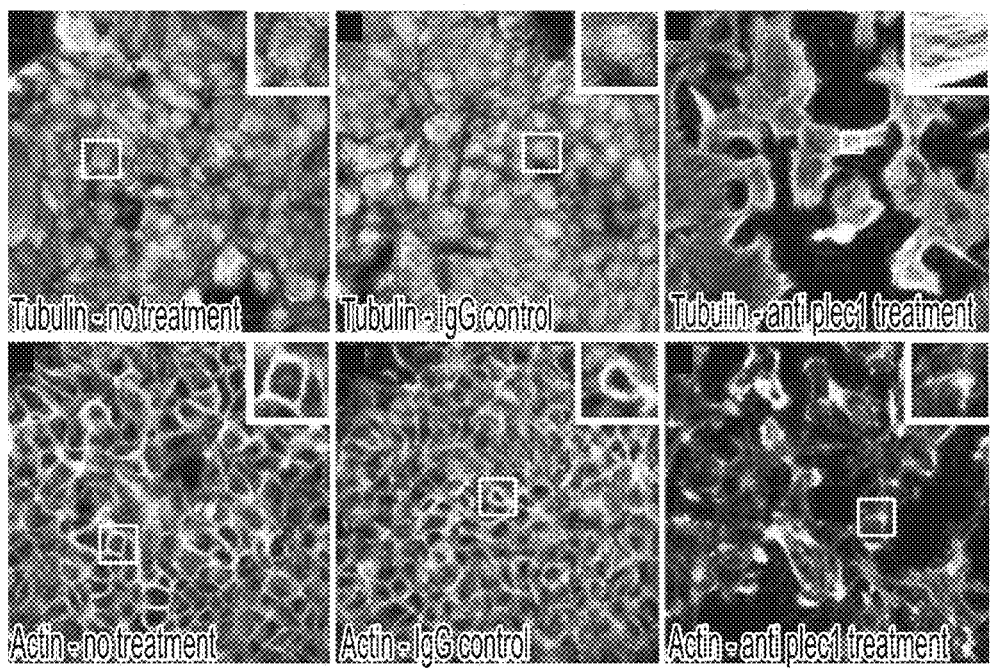

The effect of anti-plec1 treatment on cancer cell survival was examined Anti-plectin-1 antibodies Pab1 and Pab2 (also referred to as anti plec1) were observed to demonstrate the highest affinity and therapeutic effect (FIGS. 1A-1B) of anti-plectin-1 antibodies tested. Treatment of cancer cells with anti-plec1 resulted in G0 as well as G2 growth arrest (FIG. 2A). The EC50 of anti-plec1 cells was calculated as 444.4 nM (FIG. 2B). Anti-plec1 treatment was also observed to alter cell morphology from homogenous epithelial-like shaped cells to stellar-like shaped cells by acting on microtubules and actin filaments (FIG. 2C).

Cell lines were incubated with increasing concentrations of anti-plec1 for 72 hours. Cells were analyzed via sulforhodamine B (SRB)-based cell survival assay. EC50s were calculated by logistic regression (GraphPad Prism) and reported as the concentration of monoclonal antibody (mAb) (expressed in nanomolar, nM) that reduced cell viability by 50%. Growth inhibition was limited to plectin-1-expressing cancer cells. Normal cells that have cytoplasmic plectin-1 expression such as heart, kidney, skin, and pancreas all were unaffected by anti-plec1 treatment (Table 3; ND: not demonstrated; "/": no data).

TABLE 3

Effect of anti-plec1 on cell survival after 72 hours.

| | | | | | EC50 (nM) | |
| Cell Line | Origin | Phenotype | Tissue Type | Plec Positivity | anti-plec1 | IgG |
|---|---|---|---|---|---|---|
| YapC | Human | Cancer | Pancreas | +++ | 570 | ND |
| L3.6p1 | Human | Cancer | Pancreas | ++ | 801 | ND |
| Panc-1 | Human | Cancer | Pancreas | ++ | 467 | / |
| BxPC-3 | Human | Cancer | Pancreas | ++ | 363 | / |
| MiaPACA2 | Human | Cancer | Pancreas | ++ | 140 | ND |
| LNcaPs | Human | Cancer | Prostate | + | ND | / |
| HEK293T | Human | Normal | Kidney | – | ND | ND |
| RL14 | Human | Normal | Heart | – | ND | ND |
| HPDE | Human | Normal | Pancreas | – | ND | ND |
| Keratinocyte | Human | Normal | Skin | – | ND | ND |

Both cancer and normal cells were unaffected by treatment with control IgG. In vivo experiments with animals bearing a subcutaneous YAPC (PDAC cell line) xenograft demonstrated a dose dependent reduction in tumor volume. Animals undergoing treatment maintained body weight and were otherwise unaffected.

Figure 3:
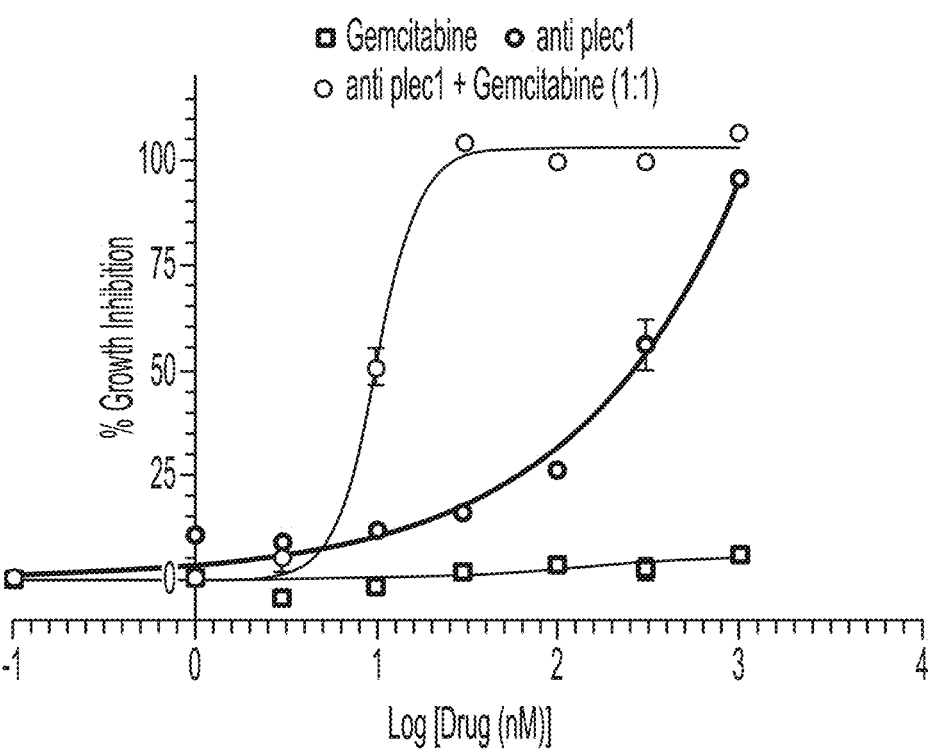
FIG. 3 shows a combination of anti-plec1 with gemcitabine (gem) has synergistic effects on cancer cells. Equal molar concentrations of anti-plec1 and gem were incubated with cells for 72 hrs. After incubation, cells were processed. Combination therapy resulted in a 20-fold decrease in IC50.

Anti-plec1 therapy has been shown to be effective on cancer cell lines and in vivo against a treatment-resistant xenograft. As monotherapies are rarely effective in the long-term (e.g., rituximab and trastuzumab), it was investigated whether anti-plec1 therapy synergizes with standard of care cancer therapies. At a 1:1 concentration ratio, anti-plec1 is synergistic in combination with Gemcitabine (gem), a standard of care therapy for pancreatic ductal adenocarcinoma (PDAC) (FIG. 3).

Effects of Anti-Plec1 and Cisplatin In Vivo

Figure 4A:
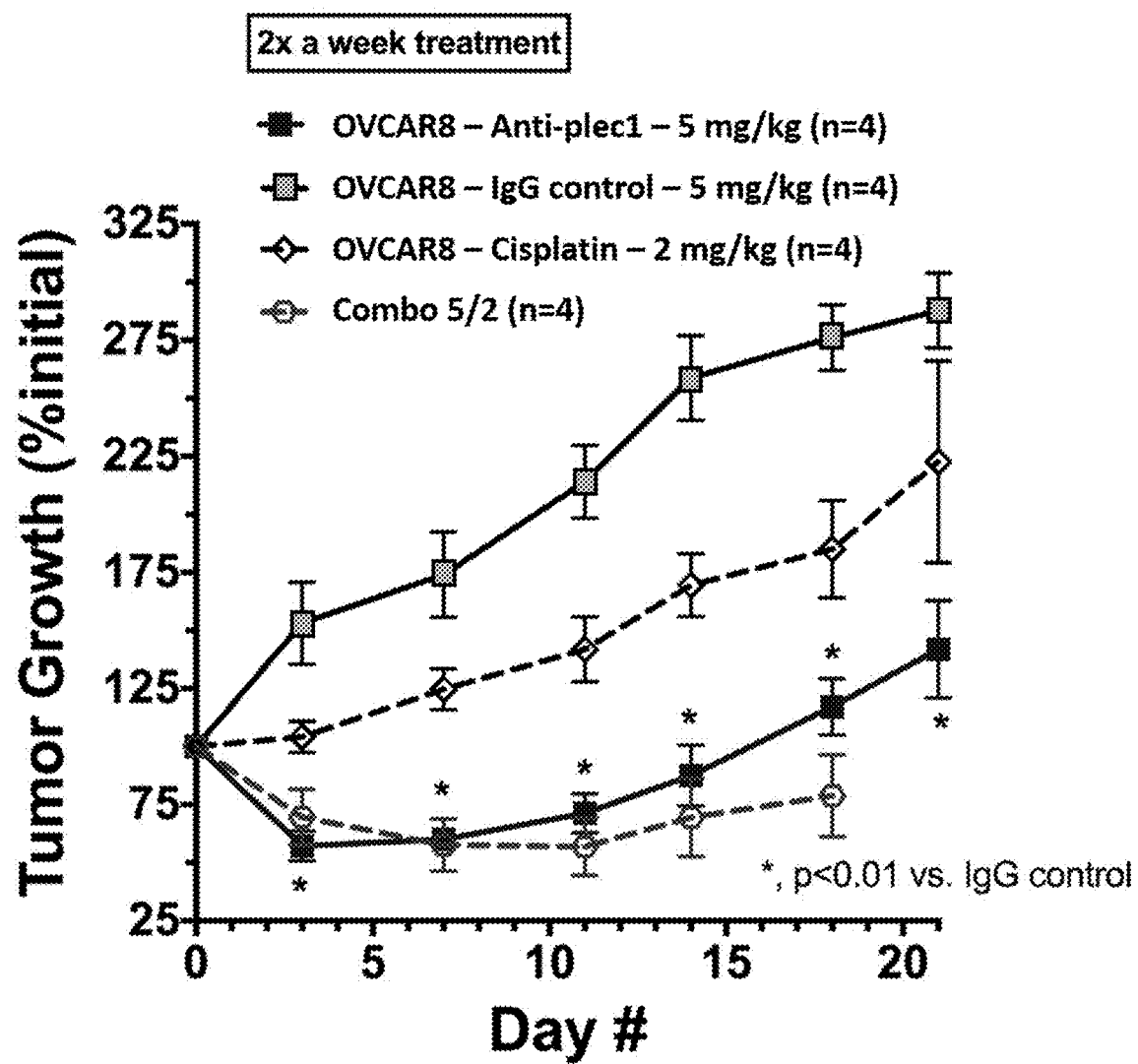
FIG. 4A shows a graph of tumor growth in mice bearing OVCAR8 tumors treated with ZB131 (5 mg/kg), cisplatin (2 mg/kg), the combination of ZB131 (5 mg/kg) and cisplatin (2 mg/kg), or IgG (5 mg/kg).
Figure 4B:
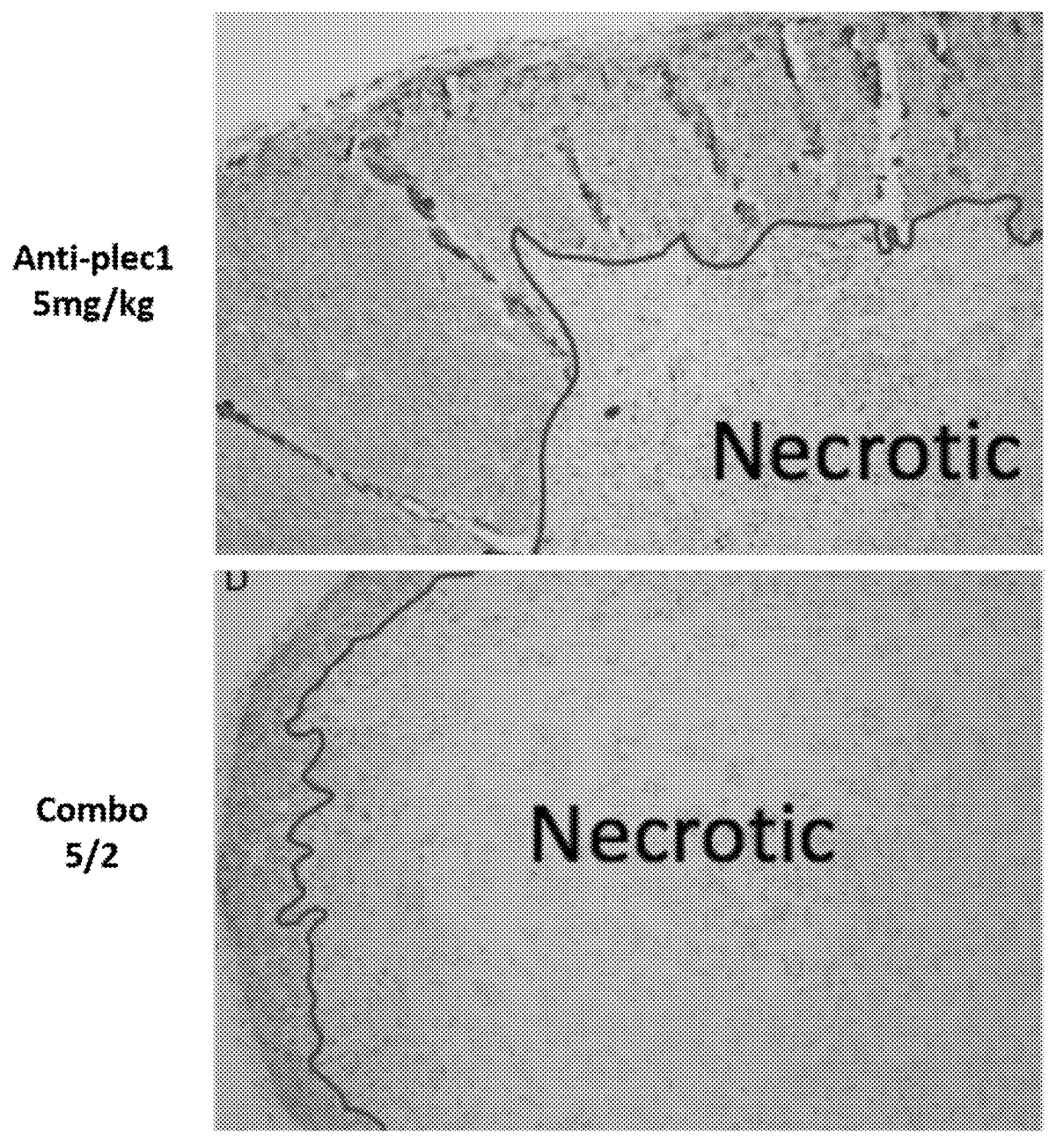
Figure 4C:
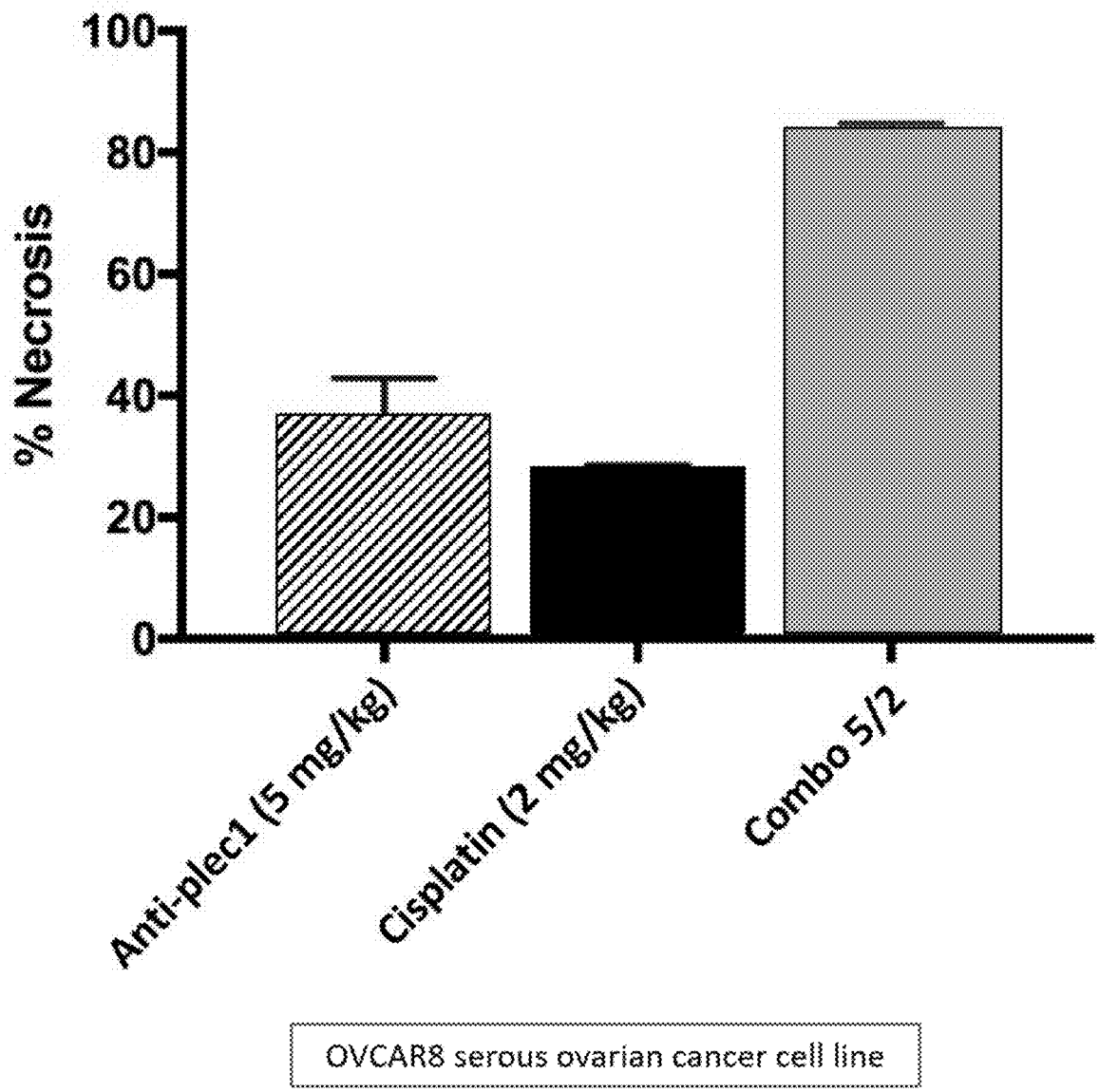
FIG. 4C shows a graph of percent necrosis of OVCAR8 serous ovarian cancer cells treated with ZB131, cisplatin, or the combination of ZB131 and cisplatin.

The effect of anti-plec1 treatment in an immunocompromised mouse model bearing OVCAR8 tumors was examined Anti plec1 (5 mg/kg), cisplatin (2 mg/kg), or the combination of anti plec1 (5 mg/kg) and cisplatin (2 mg/kg) were intravenously injected twice a week into mice bearing OVCAR8 tumors. Mice in the control group were injected with IgG (5 mg/kg). As shown by reduced tumor growth rates, mice injected with the combination of anti plec1 and cisplatin displayed extended durations of tumor regression compared to control mice injected with IgG or with mice injected with either anti plec1 or cisplatin alone (FIG. 4A). In addition, treatment with the combination of anti plec1 and cisplatin caused 85% of the tumor to necrose in vivo (FIG. 4B) and in vitro (FIG. 4C).

The observed tumor necrosis described herein occurred without the toxic side effects commonly observed with higher doses of cisplatin in mice. Typically, tumor regression is observed in mice treated with 4 mg/kg of cisplatin, which is accompanied by toxicity. As shown herein, combining a lower dose of cisplatin (2 mg/kg) with antiplec1 maintained efficacy while reducing toxicity.

SEQUENCES

Plectin (hemidesmosomal protein 1), *Homo sapiens*; target protein underlined

SEQ ID NO: 1

MVAGMLMPRDQLRAIYEVLFREGVMVAKKDRRPRSLHPHVPGVTNLQVMRAMASLRARGLV

RETFAWCHFYWYLTNEGIAHLRQYLHLPPEIVPASLQRVRRPVAMVMPARRTPHVQAVQGPLG

SPPKRGPLPTEEQRVYRRKELEEVSPETPVVPATTQRTLARPGPEPAPATDERDRVQKKTFTKWV

NKHLIKAQRHISDLYEDLRDGHNLISLLEVLSGDSLPREKGRMRFHKLQNVQIALDYLRHRQVK

LVNIRNDDIADGNPKLTLGLIWTHLHFQISDIQVSGQSEDMTAKEKLLLWSQRMVEGYQGLRCD

NFTSSWRDGRLFNAIIHRHKPLLIDMNKVYRQTNLENLDQAFSVAERDLGVTRLLDPEDVDVPQ

PDEKSIITYVSSLYDAMPRVPDVQDGVRANELQLRWQEYRELVLLLLQWMRHHTAAFEERRFP

SSFEEIEILWSQFLKFKEMELPAKEADKNRSKGIYQSLEGAVQAGQLKVPPGYHPLDVEKEWGK

LHVAILEREKQLRSEFERLECLQRIVTKLQMEAGLCEEQLNQADALLQSDVRLLAAGKVPQRAG

EVERDLDKADSMIRLLFNDVQTLKDGRHPQGEQMYRRVYRLHERLVAIRTEYNLRLKAGVAAP

ATQVAQVTLQSVQRRPELEDSTLRYLQDLLAWVEENQHRVDGAEWGVDLPSVEAQLGSHRGL

HQSIEEFRAKIERARSDEGQLSPATRGAYRDCLGRLDLQYAKLLNSSKARLRSLESLHSFVAAAT

KELMWLNEKEEEVGFDWSDRNTNMTAKKESYSALMRELELKEKKIKELQNAGDRLLREDHP

ARPTVESFQAALQTQWSWMLQLCCCIEAHLKENAAYFQFFSDVREAEGQLQKLQEALRRKYSC

DRSATVTRLEDLLQDAQDEKEQLNEYKGHLSGLAKRAKAVVQLKPRHPAHPMRGRLPLLAVC

DYKQVEVTVHKGDECQLVGPAQPSHWKVLSSSGSEAAVPSVCFLVPPPNQEAQEAVTRLEAQH

QALVTLWHQLHVDMKSLLAWQSLRRDVQLIRSWSLATFRTLKPEEQRQALHSLELHYQAFLRD

SQDAGGFGPEDRLMAEREYGSCSHHYQQLLQSLEQGAQEESRCQRCISELKDIRLQLEACETRT

VHRLRLPLDKEPARECAQRIAEQQKAQAEVEGLGKGVARLSAEAEKVLALPEPSPAAPTLRSEL

ELTLGKLEQVRSLSAIYLEKLKTISLVIRGTQGAEEVLRAHEEQLKEAQAVPATLPELEATKASLK

KLRAQAEAQQPTFDALRDELRGAQEVGERLQQRHGERDVEVERWRERVAQLLERWQAVLAQT

DVRQRELEQLGRQLRYYRESADPLGAWLQDARRRQEQIQAMPLADSQAVREQLRQEQALLEEI

ERHGEKVEECQRFAKQYINAIKDYELQLVTYKAQLEPVASPAKKPKVQSGSESVIQEYVDLRTH

YSELTTLTSQYIKFISETLRRMEEEERLAEQQRAEERERLAEVEAALEKQRQLAEAHAQAKAQA

EREAKELQQRMQEEVVRREEAAVDAQQQKRSIQEELQQLRQSSEAEIQAKARQAEAAERSRLRI

EEEIRVVRLQLEATERQRGGAEGELQALRARAEEAEAQKRQAQEEAERLRRQVQDESQRKRQA

EVELASRVKAEAEAAREKQRALQALEELRLQAEEAERRLRQAEVERARQVQVALETAQRSAEA

ELQSKRASFAEKTAQLERSLQEEHVAVAQLREEAERRAQQQAEAERAREEAERELERWQLKAN

EALRLRLQAEEVAQQKSLAQAEAEKQKEEAEREARRRGKAEEQAVRQRELAEQELEKQRQLAE

GTAQQRLAAEQELIRLRAETEQGEQQRQLLEEELARLQREAAAATQKRQELEAELAKVRAEME

VLLASKARAEEESRSTSEKSKQRLEAEAGRFRELAEEAARLRALAEEAKRQRQLAEEDAARQRA

EAERVLAEKLAAIGEATRLKTEAEIALKEKEAENERLRRLAEDEAFQRRRLEEQAAQHKADIEER

LAQLRKASDSELERQKGLVEDTLRQRRQVEEEILALKASFEKAAAGKAELELELGRIRSNAEDTL

RSKEQAELEAARQRQLAAEEERRREAEERVQKSLAAEEEAARQRKAALEEVERLKAKVEEAR

RLRERAEQESARQLQLAQEAAQKRLQAEEKAHAFAVQQKEQELQQTLQQEQSVLDQLRGEAE

AARRAAEEAEEEARVQAEREAAQSRRQVEEAERLKQSAEEQAQARAQAQAAAEKLRKEAEQEA

ARRAQAEQAALRQKQAADAEMEKHKKFAEQTLRQKAQVEQELTTLRLQLEETDHQKNLLDEE

LQRLKAEATEAARQRSQVEEELFSVRVQMEELSKLKARIEAENRALILRDKDNTQRFLQEEAEK

-continued

```
MKQVAEEAARLSVAAQEAARLRQLAEEDLAQQRALAEKMLKEKMQAVQEATRLKAEAELLQ

QQKELAQEQARRLQEDKEQMAQQLAEETQGFQRTLEAERQRQLEMSAEAERLKLRVAEMSRA

QARAEEDAQRFRKQAEEIGEKLHRTELATQEKVTLVQTLEIQRQQSDHDAERLREAIAELEREKE

KLQQEAKLLQLKSEEMQTVQQEQLLQETQALQQSFLSEKDSLLQRERFIEQEKAKLEQLFQDEV

AKAQQLREEQQRQQQQMEQERQRLVASMEEARRRQHEAEEGVRRKQEELQQLEQQRRQQEEL

LAEENQRLREQLQLLEEQHRAALAHSEEVTASQVAATKTLPNGRDALDGPAAEAEPEHSFDGLR

RKVSAQRLQEAGILSAEELQRLAQGHTTVDELARREDVRHYLQGRSSIAGLLLKATNEKLSVYA

ALQRQLLSPGTALILLEAQAASGFLLDPVRNRRLTVNEAVKEGVVGPELHHKLLSAERAVTGYK

DPYTGQQISLFQAMQKGLIVREHGIRLLEAQIATGGVIDPVHSHRVPVDVAYRRGYFDEEMNRV

LADPSDDTKGFFDPNTHENLTYLQLLERCVEDPETGLCLLPLTDKAAKGGELVYTDSEARDVFE

KATVSAPFGKFQGKTVTIWEIINSEYFTAEQRRDLLRQFRTGRITVEKIIKIIITVVEEQEQKGRL

CFEGLRSLVPAAELLESRVIDRELYQQLQRGERSVRDVAEVDTVRRALRGANVIAGVWLEEAGQK

LSIYNALKKDLLPSDMAVALLEAQAGTGHIIDPATSARLTVDEAVRAGLVGPEFHEKLLSAEKA

VTGYRDPYTGQSVSLFQALKKGLIPREQGLRLLDAQLSTGGIVDPSKSHRVPLDVACARGCLDE

ETSRALSAPRADAKAYSDPSTGEPATYGELQQRCRPDQLTGLSLLPLSEKAARARQEELYSELQA

RETFEKTPVEVPVGGFKGRTVTVWELISSEYFTAEQRQELLRQFRTGKVTVEKVIKILITIVEEVE

TLRQERLSFSGLRAPVPASELLASGVLSRAQFEQLKDGKTTVKDLSELGSVRTLLQGSGCLAGIY

LEDTKEKVSIYEAMRRGLLRATTAALLLEAQAATGFLVDPVRNQRLYVHEAVKAGVVGPELHE

QLLSAEKAVTGYRDPYSGSTISLFQAMQKGLVLRQHGIRLLEAQIATGGIIDPVHSHRVPVDVAY

QRGYFSEEMNRVLADPSDDTKGFFDPNTHENLTYRQLLERCVEDPETGLRLLPLKGAEKAEVVE

TTQVYTEEETRRAFEETQIDIPGGGSHGGSTMSLWEVMQSDLIPEEQRAQLMADFQAGRVTKER

MIIIIEIIEKTEIIRQQGLASYDYVRRRLTAEDLFEARIISLETYNLLREGTRSLREALEAESAW

CYLYGTGSVAGVYLPGSRQTLSIYQALKKGLLSAEVARLLLEAQAATGFLLDPVKGERLTVDEAVR

KGLVGPELHDRLLSAERAVTGYRDPYTEQTISLFQAMKKELIPTEEALRLLDAQLATGGIVDPRLG

FHLPLEVAYQRGYLNKDTHDQLSEPSEVRSYVDPSTDERLSYTQLLRRCRRDDGTGQLLLPLSD

ARKLTFRGLRKQITMEELVRSQVMDEATALQLREGLTSIEEVTKNLQKFLEGTSCIAGVFVDATK

ERLSVYQAMKKGIIRPGTAFELLEAQAATGYVIDPIKGLKLTVEEAVRMGIVGPEFKDKLLSAER

AVTGYKDPYSGKLISLFQAMKKGLILKDHGIRLLEAQIATGGIIDPEESHRLPVEVAYKRGLFDEE

MNEILTDPSDDTKGFFDPNTEENLTYLQLMERCITDPQTGLCLLPLKEKKRERKTSSKSSVRKRR

VVIVDPETGKEMSVYEAYRKGLIDHQTYLELSEQECEWEEITI<u>SSSDGVVKSMIIDRRSGRQYDID

DAIAKNLIDRSALDQYRAGTLSITEFADMLSGNAGGFRSRSSSVGSSSSYPISPAVSRTQLASWSD

PTEETGPVAGILDTETLEKVSITEAMHRNLVDNITGQRLLEAQACTGGIIDPSTGERFPVTDAVNK

GLVDKIMVDRINLAQKAFCGFEDPRTKTKMSAAQALKKGWLYYEAGQRFLEVQYLTGGLIEPD

TPGRVPLDEALQRGTVDARTAQKLRDVGAYSKYLTCPKTKLKISYKDALDRSMVEEGTGLRLL

EAAAQSTKGYYSPYSVSGSGSTAGSRTGSRTGSRAGSRRGSFDATGSGFSMTFSSSSYSSSGYGR

RYASGSSASLGGPESAVA</u>
```

Plectin (hemidesmosomal protein 1), *Homo sapiens*; target protein underlined

SEQ ID NO: 2

```
SSSDGVVKSMIIDRRSGRQYDIDDAIAKNLIDRSALDQYRAGTLSITEFADMLSGNAGGFRSRSSS

VGSSSSYPISPAVSRTQLASWSDPTEETGPVAGILDTETLEKVSITEAMHRNLVDNITGQRLLEAQ

ACTGGIIDPSTGERFPVTDAVNKGLVDKIMVDRINLAQKAFCGFEDPRTKTKMSAAQALKKGW
```

-continued

LYYEAGQRFLEVQYLTGGLIEPDTPGRVPLDEALQRGTVDARTAQKLRDVGAYSKYLTCPKTK

LKISYKDALDRSMVEEGTGLRLLEAAAQSTKGYYSPYSVSGSGSTAGSRTGSRTGSRAGSRRGS

FDATGSGFSMTFSSSSYSSSGYGRRYASGSSASLGGPESAVA

Pab2 Sequences

| Name | Sequence | SEQ ID NO: |
|---|---|---|
| Pab2 Heavy Chain | ATGAACTTCGGGCTCAGCTTGATTTTCCTTGCCCTCATTTTA AAAGGTGTCCAGTGTGAGGTGCAGCTGGTGGAGTCTGGGG GAGACTTGGTGAAGCCTGGAGGGTCCCTGAAACTCTCCTGT GCAGCCTCTGGATTCACTTTCAGTAGGTATGGCATGTCTTG GGTTCGCCAGACTCCAGACAAGAGGCTGGAGTGGGTCGCA ACCATTAGTATTGGTGGTACTTACACCTACTATCCAGACAG TATGAAGGGGCGATTCACCATCTCCAGAGACAATGCCAAG AACACCCTGTACCTGCAAATGAGCAGTCTGAAGTCTGAGG ACACAGCCATGTATTACTGTGCAAGACGGGGGTATGGTAA CTACTCTTACTATGGTATGGACTACTGGGGTCAAGGAACCT CAGTCACCGTCTCCTCAGCCAAAACGACACCCCCATCTGTC TATCCACTGGCCCCTGGATCTGCTGCCCAAACTAACTCCAT GGTGACCCTGGGATGCCTGGTCAAGGGCTATTTCCCTGAGC CAGTGACAGTGACCTGGAACTCTGGATCCCTGTCCAGCGGT GTGCACACCTTCCCAGCTGTCCTGCAGTCTGACCTCTACAC TCTGAGCAGCTCAGTGACTGTCCCCTCCAGCACCTGGCCCA GCGAGACCGTCACCTGCAACGTTGCCCACCCGGCCAGCAG CACCAAGGTGGACAAGAAAATTGTGCCCAGGGATTGTGGT TGTAAGCCTTGCATATGTACAGTCCCAGAAGTATCATCTGT CTTCATCTTCCCCCCAAAGCCCAAGGATGTGCTCACCATTA CTCTGACTCCTAAGGTCACGTGTGTTGTGGTAGACATCAGC AAGGATGATCCCGAGGTCCAGTTCAGCTGGTTTGTAGATGA TGTGGAGGTGCACACAGCTCAGACGCAACCCCGGGAGGAG CAGTTCAACAGCACTTTCCGCTCAGTCAGTGAACTTCCCAT CATGCACCAGGACTGGCTCAATGGCAAGGAGTTCAAATGC AGGGTCAACAGTGCAGCTTTCCCTGCCCCCATCGAGAAAA CCATCTCCAAAACCAAAGGCAGACCGAAGGCTCCACAGGT GTACACCATTCCACCTCCCAAGGAGCAGATGGCCAAGGAT AAAGTCAGTCTGACCTGCATGATAACAGACTTCTTCCCTGA AGACATTACTGTGGAGTGGCAGTGGAATGGGCAGCCAGCG GAGAACTACAAGAACACTCAGCCCATCATGGACACAGATG GCTCTTACTTCGTCTACAGCAAGCTCAATGTGCAGAAGAGC AACTGGGAGGCAGGAAATACTTTCACCTGCTCTGTGTTACA TGAGGGCCTGCACAACCACCATACTGAGAAGAGCCTCTCC CACTCTCCTGGTAAATGA | 3 |
| Pab2 Heavy Chain Leader | ATGAACTTCGGGCTCAGCTTGATTTTCCTTGCCCTCATTTTA AAAGGTGTCCAGTGT | 4 |
| Pab2 Heavy Chain FR1 | GAGGTGCAGCTGGTGGAGTCTGGGGGAGACTTGGTGAAGC CTGGAGGGTCCCTGAAACTCTCCTGTGCAGCCTCTGGATTC ACTTTCAGT | 5 |
| Pab2 Heavy Chain CDR1 | AGGTATGGCATGTCT | 6 |
| Pab2 Heavy Chain FR2 | TGGGTTCGCCAGACTCCAGACAAGAGGCTGGAGTGGGTCGCA | 7 |
| Pab2 Heavy Chain CDR2 | ACCATTAGTATTGGTGGTACTTACACCTACTATCCAGACAG TATGAAGGGG | 8 |
| Pab2 Heavy Chain FR 3 | CGATTCACCATCTCCAGAGACAATGCCAAGAACACCCTGT ACCTGCAAATGAGCAGTCTGAAGTCTGAGGACACAGCCAT GTATTACTGTGCAAGA | 9 |
| Pab2 Heavy Chain CDR3 | CGGGGGTATGGTAACTACTCTTACTATGGTATGGACTAC | 10 |
| Pab2 Heavy Chain FR 4 | TGGGGTCAAGGAACCTCAGTCACCGTCTCCTCA | 11 |
| Pab2 Heavy Chain Variable Region | GAGGTGCAGCTGGTGGAGTCTGGGGGAGACTTGGTGAAGC CTGGAGGGTCCCTGAAACTCTCCTGTGCAGCCTCTGGATTC ACTTTCAGTAGGTATGGCATGTCTTGGGTTCGCCAGACTCC AGACAAGAGGCTGGAGTGGGTCGCAACCATTAGTATTGGT GGTACTTACACCTACTATCCAGACAGTATGAAGGGGCGATT | 12 |

-continued

| Name | Sequence | SEQ ID NO: |
|---|---|---|
|  | CACCATCTCCAGAGACAATGCCAAGAACACCCTGTACCTG<br>CAAATGAGCAGTCTGAAGTCTGAGGACACAGCCATGTATT<br>ACTGTGCAAGACGGGGGTATGGTAACTACTCTTACTATGGT<br>ATGGACTACTGGGGTCAAGGAACCCTCAGTCACCGTCTCCTCA |  |
| Pab2 Heavy Chain Constant Region | GCCAAAACGACACCCCCATCTGTCTATCCACTGGCCCCTGG<br>ATCTGCTGCCCAAACTAACTCCATGGTGACCCTGGGATGCC<br>TGGTCAAGGGCTATTTCCCTGAGCCAGTGACAGTGACCTGG<br>AACTCTGGATCCCTGTCCAGCGGTGTGCACACCTTCCCAGC<br>TGTCCTGCAGTCTGACCTCTACACTCTGAGCAGCTCAGTGA<br>CTGTCCCCTCCAGCACCTGGCCCAGCGAGACCGTCACCTGC<br>AACGTTGCCCACCCGGCCAGCAGCACCAAGGTGGACAAGA<br>AAATTGTGCCCAGGGATTGTGGTTGTAAGCCTTGCATATGT<br>ACAGTCCCAGAAGTATCATCTGTCTTCATCTTCCCCCCAAA<br>GCCCAAGGATGTGCTCACCATTACTCTGACTCCTAAGGTCA<br>CGTGTGTTGTGGTAGACATCAGCAAGGATGATCCCGAGGT<br>CCAGTTCAGCTGGTTTGTAGATGATGTGGAGGTGCACACAG<br>CTCAGACGCAACCCCGGGAGGAGCAGTTCAACAGCACTTT<br>CCGCTCAGTCAGTGAACTTCCCATCATGCACCAGGACTGGC<br>TCAATGGCAAGGAGTTCAAATGCAGGGTCAACAGTGCAGC<br>TTTCCCTGCCCCCATCGAGAAAACCATCTCCAAAACCAAAG<br>GCAGACCGAAGGCTCCACAGGTGTACACCATTCCACCTCCC<br>AAGGAGCAGATGGCCAAGGATAAAGTCAGTCTGACCTGCA<br>TGATAACAGACTTCTTCCCTGAAGACATTACTGTGGAGTGG<br>CAGTGGAATGGGCAGCCAGCGGAGAACTACAAGAACACTC<br>AGCCCATCATGGACACAGATGGCTCTTACTTCGTCTACAGC<br>AAGCTCAATGTGCAGAAGAGCAACTGGGAGGCAGGAATA<br>CTTTCACCTGCTCTGTGTTACATGAGGGCCTGCACAACCAC<br>CATACTGAGAAGAGCCTCTCCCACTCTCCTGGTAAA | 13 |
| Pab2 Heavy Chain | MNFGLSLIFLALILKGVQCEVQLVESGGDLVKPGGSLKLSCAA<br>SGFTFSRYGMSWVRQTPDKRLEWVATISIGGTYTYYPDSMKG<br>RFTISRDNAKNTLYLQMSSLKSEDTAMYYCARRGYGNYSYY<br>GMDYWGQGTSVTVSSAKTTPPSVYPLAPGSAAQTNSMVTLG<br>CLVKGYFPEPVTVTWNSGSLSSGVHTFPAVLQSD | 14 |
| Pab2 Heavy Chain Leader | MNFGLSLIFLALILKGVQC | 15 |
| Pab2 Heavy Chain FR1 | EVQLVESGGDLVKPGGSLKLSCAASGFTFS | 16 |
| Pab2 Heavy Chain CDR1 | RYGMS | 17 |
| Pab2 Heavy Chain FR2 | WVRQTPDKRLEWVA | 18 |
| Pab2 Heavy Chain CDR2 | TISIGGTYTYYPDSMKG | 19 |
| Pab2 Heavy Chain FR 3 | RFTISRDNAKNTLYLQMSSLKSEDTAMYYCAR | 20 |
| Pab2 Heavy Chain CDR3 | RGYGNYSYYGMDY | 21 |
| Pab2 Heavy Chain FR 4 | WGQGTSVTVSS | 22 |
| Pab2 Heavy Chain Variable Region | EVQLVESGGDLVKPGGSLKLSCAASGFTFSRYGMSWVRQTPD<br>KRLEWVATISIGGTYTYYPDSMKGRFTISRDNAKNTLYLQMS<br>SLKSEDTAMYYCARRGYGNYSYYGMDYWGQGTSVTVSS | 23 |
| Pab2 Heavy Chain Constant Region | AKTTPPSVYPLAPGSAAQTNSMVTLGCLVKGYFPEPVTVTWN<br>SGSLSSGVHTFPAVLQSDLYTLSSSVTVPSSTWPSETVTCNVA<br>HPASSTKVDKKIVPRDCGCKPCICTVPEVSSVFIFPPKPKDVLT<br>ITLTPKVTCVVVDISKDDPEVQFSWFVDDVEVHTAQTQPREEQ<br>FNSTFRSVSELPIMHQDWLNGKEFKCRVNSAAFPAPIEKTISKT<br>KGRPKAPQVYTIPPPKEQMAKDKVSLTCMITDFFPEDITVEWQ<br>WNGQPAENYKNTQPIMDTDGSYFVYSKLNVQKSNWEAGNTF<br>TCSVLHEGLHNHHTEKSLSHSPGK | 24 |
| Pab2 Light Chain | ATGAGGTTCTCTGCTCAGCTTCTGGGGCTGCTTGTGCTCTG<br>GATCCCTGGATCCACTGCAGATATTGTGATGACGCAGGCTG<br>CATTCTCCAATCCAGTCACTCTTGGAACATCAGCTTCCATC | 25 |

| Name | Sequence | SEQ ID NO: |
|---|---|---|
|  | TCCTGCAGGTCTAGTAAGAGTCTCCTACATAGTAATGGCAT CACTTATTTGTATTGGTATCTGCAGAAGCCAGGCCAGTCTC CTCAGCTCCTGATTTATCAGATGTCCAACCTTGCCTCAGGA GTCCCAGACAGGTTCAGTAGCAGTGGGTCAGGAACTGATT TCACACTGAGAATCAGCAGAGTGGAGGCTGAGGATGTGGG TGTTTATTACTGTGCTCAAAATCTAGAACTTCCGCTCACGTT CGGTGCTGGGACCAAGCTGGAGCTGAAACGGGCTGATGCT GCACCAACTGTATCCATCTTCCCACCATCCAGTGAGCAGTT AACATCTGGAGGTGCCTCAGTCGTGTGCTTCTTGAACAACT TCTACCCCAAAGACATCAATGTCAAGTGGAAGATTGATGG CAGTGAACGACAAAATGGCGTCCTGAACAGTTGGACTGAT CAGGACAGCAAAGACAGCACCTACAGCATGAGCAGCACCC TCACGTTGACCAAGGACGAGTATGAACGACATAACAGCTA TACCTGTGAGGCCACTCACAAGACATCAACTTCACCCATTG TCAAGAGCTTCAACAGGAATGAGTGTTAG |  |
| Pab2 Light Chain Leader | ATGAGGTTCTCTGCTCAGCTTCTGGGGCTGCTTGTGCTCTG GATCCCTGGATCCACTGCA | 26 |
| Pab2 Light Chain FR1 | GATATTGTGATGACGCAGGCTGCATTCTCCAATCCAGTCAC TCTTGGAACATCAGCTTCCATCTCCTGC | 27 |
| Pab2 Light Chain CDR1 | AGGTCTAGTAAGAGTCTCCTACATAGTAATGGCATCACTTA TTTGTAT | 28 |
| Pab2 Light Chain FR2 | TGGTATCTGCAGAAGCCAGGCCAGTCTCCTCAGCTCCTGAT TTAT | 29 |
| Pab2 Light Chain CDR2 | CAGATGTCCAACCTTGCCTCA | 30 |
| Pab2 Light Chain FR 3 | GGAGTCCCAGACAGGTTCAGTAGCAGTGGGTCAGGAACTG ATTTCACACTGAGAATCAGCAGAGTGGAGGCTGAGGATGT GGGTGTTTATTACTGT | 31 |
| Pab2 Light Chain CDR3 | GCTCAAAATCTAGAACTTCCGCTCACG | 32 |
| Pab2 Light Chain FR 4 | TTCGGTGCTGGGACCAAGCTGGAGCTGAAA | 33 |
| Pab2 Light Chain Variable Region | GATATTGTGATGACGCAGGCTGCATTCTCCAATCCAGTCAC TCTTGGAACATCAGCTTCCATCTCCTGCAGGTCTAGTAAGAG TCTCCTACATAGTAATGGCATCACTTATTTGTATTGGTATCTG CAGAAGCCAGGCCAGTCTCCTCAGCTCCTGATTTATCAGATG TCCAACCTTGCCTCAGGAGTCCCAGACAGGTTCAGTAGCAGTG GGTCAGGAACTGATTTCACACTGAGAATCAGCAGAGTGGAGGCT GAGGATGTGGGTGTTTATTACTGTGCTCAAAATCTAGAACTT CCGCTCACGTTCGGTGCTGGGACCAAGCTGGAGCTGAAA | 34 |
| Pab2 Light Chain Constant Region | CTGTGCTCAAAATCTAGAACTTCCGCTCACGTTCGGTGCTG GGACCAAGCTGGAGCTGAAACGGGCTGATGCTGCACCAAC TGTATCCATCTTCCCACCATCCAGTGAGCAGTTAACATCTG GAGGTGCCTCAGTCGTGTGCTTCTTGAACAACTTCTACCCC AAAGACATCAATGTCAAGTGGAAGATTGATGGCAGTGAAC GACAAAATGGCGTCCTGAACAGTTGGACTGATCAGGACAG CAAAGACAGCACCTACAGCATGAGCAGCACCCTCACGTTG ACCAAGGACGAGTATGAACGACATAACAGCTATACCTGTG AGGCCACTCACAAGACATCAACTTCACCCATTGTCAAGAG CTTCAACAGGAATGAGTGT | 35 |
| Pab2 Light Chain | MRFSAQLLGLLVLWIPGSTADIVMTQAAFSNPVTLGTSASISC RSSKSLLHSNGITYLYWYLQKPGQSPQLLIYQMSNLASGVPDR FSSSGSGTDFTLRISRVEAEDVGVYYCAQNLELPLTFGAGTKL ELKRADAAPTVS1FPPSSEQLTSGGASVVCFLNNFYPKDINVK WK1DGSERQNGVLNSWTDQDSKDSTYSMSSTLTLTKDEYER HNSYTCEATHKTSTSP1VKSFNRNEC | 36 |
| Pab2 Light Chain Leader | MRFSAQLLGLLVLWIPGSTA | 37 |
| Pab2 Light Chain FR1 | DIVMTQAAFSNPVTLGTSASISC | 38 |
| Pab2 Light Chain CDR1 | RSSKSLLHSNGITYLY | 39 |

| Name | Sequence | SEQ ID NO: |
|---|---|---|
| Pab2 Light Chain FR2 | WYLQKPGQSPQLLIY | 40 |
| Pab2 Light Chain CDR2 | QMSNLAS | 41 |
| Pab2 Light Chain FR 3 | GVPDRFSSSGSGTDFTLRISRVEAEDVGVYYC | 42 |
| Pab2 Light Chain CDR3 | AQNLELPLT | 43 |
| Pab2 Light Chain FR 4 | FGAGTKLELK | 44 |
| Pab2 Light Chain Variable Region | DIVMTQAAFSNPVTLGTSASISCRSSKSLLHSNGITYLYWYLQKPGQSPQLLIYQMSNLASGVPDRFSSSGSGTDFTLRISRVEAEDVGVYYCAQNLELPLTFGAGTKLELK | 45 |
| Pab2 Light Chain Constant Region | RADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC | 46 |

Pab1 Sequences

| Name | Sequence | SEQ ID NO: |
|---|---|---|
| Pab1 Heavy Chain | ATGGCTTGGGTGTGGACCTTGCTATTCCTGATGGCAGCTGCCCAAAGTATCCAAGCACAGATCCAGTTGGTGCAGTCTGGACCTGAGCTGAAGAAGCCTGGAGAGACAGTCAAGATCTCCTGCAAGGCTTCTGGTTATACCTTCACAGACTATTCAATGCACTGGGTGAAGCAGGCTCCAGGAAAGGGTTTAAAGTGGATGGGCTGGATAAACACTGAGACTGGTGAGCCAACATATGCAGATGACTTCAAGGGACGGTTTGCCTTCTCTTTGGAAACCTCTGCCAGCACTGCCTATTTGCAGATCAACAACCTCAAAAATGAGGACACGGCTACATATTTCTGTGCCCCCGGAGGGTTTGCTTACTGGGGCCAAGGGACTCTGGTCACTGTCTCTGCAGCCAAAACAACACCCCCATCAGTCTATCCACTGGCCCCTGGGTGTGGAGATACAACTGGTTCCTCCGTGACTCTGGGATGCCTGGTCAAGGGCTACTTCCCTGAGTCAGTGACTGTGACTTGGAACTCTGGATCCCTGTCCAGCAGTGTGCACACCTTCCCAGCTCTCCTGCAGTCTGGACTCTACACTATGAGCAGCTCAGTGACTGTCCCCTCCAGCACCTGGCCAAGTCAGACCGTCACCTGCAGCGTTGCTCACCCAGCCAGCAGCACCACGGTGGACAAAAAACTTGAGCCCAGCGGGCCCATTTCAACAATCAACCCCTGTCCTCCATGCAAGGAGTGTCACAAATGCCCAGCTCCTAACCTCGAGGGTGGACCATCCGTCTTCATCTTCCCTCCAAATATCAAGGATGTACTCATGATCTCCCTGACACCCAAGGTCACGTGTGTGGTGGTGGATGTGAGCGAGGATGACCCAGACGTCCAGATCAGCTGGTTTGTGAACAACGTGGAAGTACACACAGCTCAGACACAAACCCATAGAGAGGATTACAACAGTACTATCCGGGTGGTCAGCACCCTCCCCATCCAGCACCAGGACTGGATGAGTGGCAAGGAGTTCAAATGCAAGGTCAACAACAAAGACCTCCCATCACCCATCGAGAGAACCATCTCAAAAATTAAAGGGCTAGTCAGAGCTCCACAAGTATACATCTTGCCGCCACCAGCAGAGCAGTTGTCCAGGAAAGATGTCAGTCTCACTTGCCTGGTCGTGGGCTTCAACCCTGGAGACATCAGTGTGGAGTGGACCAGCAATGGGCATACAGAGGAGAACTACAAGGACACCGCACCAGTCCTGGACTCTGACGGTTCTTACTTCATATATAGCAAGCTCAATATGAAAACAAGCAAGTGGGAGAAAACAGATTCCTTCTCATGCAACGTGAGACACGAGGGTCTGAAAAATTACTACCTGAAGAAGACCATCTCCCGGTCTCCGGGTAAATGA | 47 |
| Pab1 Heavy Chain Leader | ATGGCTTGGGTGTGGACCTTGCTATTCCTGATGGCAGCTGCCCAAAGTATCCAAGCA | 48 |
| Pab1 Heavy Chain FR1 | CAGATCCAGTTGGTGCAGTCTGGACCTGAGCTGAAGAAGCCTGGAGAGACAGTCAAGATCTCCTGCAAGGCTTCTGGTTATACCTTCACA | 49 |

| Name | Sequence | SEQ ID NO: |
|---|---|---|
| Pab1 Heavy Chain CDR1 | GACTATTCAATGCAC | 50 |
| Pab1 Heavy Chain FR2 | TGGGTGAAGCAGGCTCCAGGAAAGGGTTTAAAGTGGATGGGC | 51 |
| Pab1 Heavy Chain CDR2 | TGGATAAACACTGAGACTGGTGAGCCAACATATGCAGATG ACTTCAAGGGA | 52 |
| Pab1 Heavy Chain FR 3 | CGGTTTGCCTTCTCTTTGGAAACCTCTGCCAGCACTGCCTAT TTGCAGATCAACAACCTCAAAAATGAGGACACGGCTACAT ATTTCTGTGCCCCC | 53 |
| Pab1 Heavy Chain CDR3 | GGAGGGTTTGCTTAC | 54 |
| Pab1 Heavy Chain FR 4 | TGGGGCCAAGGGACTCTGGTCACTGTCTCTGCA | 55 |
| Pab1 Heavy Chain Variable Region | CAGATCCAGTTGGTGCAGTCTGGACCTGAGCTGAAGAAGC CTGGAGAGACAGTCAAGATCTCCTGCAAGGCTTCTGGTTAT ACCTTCACAGACTATTCAATGCACTGGGTGAAGCAGGCTCC AGGAAAGGGTTTAAAGTGGATGGGCTGGATAAACACTGAG ACTGGTGAGCCAACATATGCAGATGACTTCAAGGGACGGT TTGCCTTCTCTTTGGAAACCTCTGCCAGCACTGCCTATTTGC AGATCAACAACCTCAAAAATGAGGACACGGCTACATATTT CTGTGCCCCCGGAGGGTTTGCTTACTGGGGCCAAGGGACTC TGGTCACTGTCTCTGCA | 56 |
| Pab1 Heavy Chain Constant Region | GCCAAAACAACACCCCCATCAGTCTATCCACTGGCCCCTGG GTGTGGAGATACAACTGGTTCCTCCGTGACTCTGGGATGCC TGGTCAAGGGCTACTTCCCTGAGTCAGTGACTGTGACTTGG AACTCTGGATCCCTGTCCAGCAGTGTGCACACCTTCCCAGC TCTCCTGCAGTCTGGACTCTACACTATGAGCAGCTCAGTGA CTGTCCCCTCCAGCACCTGGCCAAGTCAGACCGTCACCTGC AGCGTTGCTCACCCAGCCAGCAGCACCACGGTGGACAAAA AACTTGAGCCCAGCGGGCCCATTTCAACAATCAACCCCTGT CCTCCATGCAAGGAGTGTCACAAATGCCCAGCTCCTAACCT CGAGGGTGGACCATCCGTCTTCATCTTCCCTCCAAATATCA AGGATGTACTCATGATCTCCCTGACACCCAAGGTCACGTGT GTGGTGGTGGATGTGAGCGAGGATGACCCAGACGTCCAGA TCAGCTGGTTTGTGAACAACGTGGAAGTACACACAGCTCA GACACAAACCCATAGAGAGGATTACAACAGTACTATCCGG GTGGTCAGCACCCTCCCCATCCAGCACCAGGACTGGATGA GTGGCAAGGAGTTCAAATGCAAGGTCAACAACAAAGACCT CCCATCACCCATCGAGAGAACCATCTCAAAAATTAAAGGG CTAGTCAGAGCTCCACAAGTATACATCTTGCCGCCACCAGC AGAGCAGTTGTCCAGGAAAGATGTCAGTCTCACTTGCCTGG TCGTGGGCTTCAACCCTGGAGACATCAGTGTGGAGTGGACC AGCAATGGGCATACAGAGGAGAACTACAAGGACACCGCACC AGTCCTGGACTCTGACGGTTCTTACTTCATATATAGCAAGCT CAATATGAAAACAAGCAAGTGGGAGAAAACAGATTCCTTCT CATGCAACGTGAGACACGAGGGTCTGAAAAATTACTACCT GAAGAAGACCATCTCCCGGTCTCCGGGTAAA | 57 |
| Pab1 Heavy Chain | MAWVWTLLFLMAAAQSIQAQIQLVQSGPELKKPGETVKISCK ASGYTFTDYSMHWVKQAPGKGLKWMGWINTETGEPTYADD FKGRFAFSLETSASTAYLQINNLKNEDTATYFCAPGGFAYWG QGTLVTVSAAKTTPPSVYPLAPGCGDTTGSSVTLGCLVKGYF PESVTVTWNSGSLSSSVHTFPALLQSGLYTMSSSVTVPSSTWP SQTVTCSVAHPASSTTVDKKLEPSGPISTINPCPPCKECHKCPA PNLEGGPSVFIFPPNIKDVLMISLTPKVTCVVVDVSEDDPDVQI SWFVNNVEVHTAQTQTHREDYNSTIRVVSTLPIQHQDWMSG KEFKCKVNNKDLPSPIERTISKIKGLVRAPQVYILPPPAEQLSR KDVSLTCLVVGFNPGDISVEWTSNGHTEENYKDTAPVLDSDG SYFIYSKLNMKTSKWEKTDSFSCNVRHEGLKNYYLKKTISRSP GK | 58 |
| Pab1 Heavy Chain Leader | MAWVWTLLFLMAAAQSIQA | 59 |
| Pab1 Heavy Chain FR1 | QIQLVQSGPELKKPGETVKISCKASGYTFT | 60 |
| Pab1 Heavy Chain CDR1 | DYSMH | 61 |

| Name | Sequence | SEQ ID NO: |
|---|---|---|
| Pab1 Heavy Chain FR2 | WVKQAPGKGLKWMG | 62 |
| Pab1 Heavy Chain CDR2 | WINTETGEPTYADDFKG | 63 |
| Pab1 Heavy Chain FR 3 | RFAFSLETSASTAYLQINNLKNEDTATYFCAP | 64 |
| PAb1 Heavy Chain CDR3 | GGFAY | 65 |
| PAb1 Heavy Chain FR 4 | WGQGTLVTVSA | 66 |
| PAb1 Heavy Chain Variable Region | QIQLVQSGPELKKPGETVKISCKASGYTFTDYSMHWVKQAPG KGLKWMGWINTETGEPTYADDFKGRFAFSLETSASTAYLQIN NLKNEDTATYFCAPGGFAYWGQGTLVTVSA | 67 |
| PAb1 Heavy Chain Constant Region | AKTTPPSVYPLAPGCGDTTGSSVTLGCLVKGYFPESVTVTWN SGSLSSSVHTFPALLQSGLYTMSSSVTVPSSTWPSQTVTCSVA HPASSTTVDKKLEPSGPISTINPCPPCKECHKCPAPNLEGGPSV FIFPPNIKDVLMISLTPKVTCVVVDVSEDDPDVQISWFVNNVE VHTAQTQTHREDYNSTIRVVSTLPIQHQDWMSGKEFKCKVN NKDLPSPIERTISKIKGLVRAPQVYILPPPAEQLSRKDVSLTCL VVGFNPGDISVEWTSNGHTEENYKDTAPVLDSDGSYFIYSKLN MKTSKWEKTDSFSCNVRHEGLKNYYLKKTISRSPGK | 68 |
| PAb1 Light Chain | ATGAGGTGCCTAGCTGAGTTCCTGGGGCTGCTTGTGCTCTG GATCCCTGGAGCCATTGGGGATATTGTGATGACTCAGGCTG CACCCTCTGTACCTGTCACTCCTGGAGAGTCAGTATCCATC TCCTGCAGGTCTAGTAAGAGTCTCCTGCATAGTAATGGCAA CACTTACTTGTATTGGTTCCTGCAGAGGCCAGGCCAGTCTC CTCAGCTCCTGATATATCGGATGTCCAACCTTGCCTCAGGA GTCCCAGACAGGTTCAGTGGCAGTGGGTCAGGAACTGCTTT CACACTGAGAATCAGTAGAGTGGAGGCTGAGGATGTGGGT GTTTATTACTGTATGCAACATCTAGAATATCCGCTCACGTT CGGTGCTGGGACCAAGCTGGAGCTGAAACGGGCTGATGCT GCACCAACTGTATCCATCTTCCCACCATCCAGTGAGCAGTT AACATCTGGAGGTGCCTCAGTCGTGTGCTTCTTGAACAACT TCTACCCCAAAGACATCAATGTCAAGTGGAAGATTGATGG CAGTGAACGACAAAATGGCGTCCTGAACAGTTGGACTGAT CAGGACAGCAAAGACAGCACCTACAGCATGAGCAGCACCC TCACGTTGACCAAGGACGAGTATGAACGACATAACAGCTA TACCTGTGAGGCCACTCACAAGACATCAACTTCACCCATTG TCAAGAGCTTCAACAGGAATGAGTGTTAG | 69 |
| PAb1 Light Chain Leader | ATGAGGTGCCTAGCTGAGTTCCTGGGGCTGCTTGTGCTCTG GATCCCTGGAGCCATTGGG | 70 |
| PAb1 Light Chain FR1 | GATATTGTGATGACTCAGGCTGCACCCTCTGTACCTGTCAC TCCTGGAGAGTCAGTATCCATCTCCTGC | 71 |
| PAb1 Light Chain CDR1 | AGGTCTAGTAAGAGTCTCCTGCATAGTAATGGCAACACTTA CTTGTAT | 72 |
| PAb1 Light Chain FR2 | TGGTTCCTGCAGAGGCCAGGCCAGTCTCCTCAGCTCCTGAT ATAT | 73 |
| PAb1 Light Chain CDR2 | CGGATGTCCAACCTTGCCTCA | 74 |
| PAb1 Light Chain FR 3 | GGAGTCCCAGACAGGTTCAGTGGCAGTGGGTCAGGAACTG CTTTCACACTGAGAATCAGTAGAGTGGAGGCTGAGGATGT GGGTGTTTATTACTGT | 75 |
| PAb1 Light Chain CDR3 | ATGCAACATCTAGAATATCCGCTCACG | 76 |
| PAb1 Light Chain FR 4 | TTCGGTGCTGGGACCAAGCTGGAGCTGAAA | 77 |
| PAb1 Light Chain Variable Region | GATATTGTGATGACTCAGGCTGCACCCTCTGTACCTGTCAC TCCTGGAGAGTCAGTATCCATCTCCTGCAGGTCTAGTAAGA GTCCTGCATAGTAATGGCAACACTTACTTGTATTGGTTC | 78 |

| Name | Sequence | SEQ ID NO: |
|---|---|---|
| | CTGCAGAGGCCAGGCCAGTCTCCTCAGCTCCTGATATATCG GATGTCCAACCTTGCCTCAGGAGTCCCAGACAGGTTCAGTG GCAGTGGGTCAGGAACTGCTTTCACACTGAGAATCAGTAG AGTGGAGGCTGAGGATGTGGGTGTTTATTACTGTATGCAAC ATCTAGAATATCCGCTCACGTTCGGTGCTGGGACCAAGCTG GAGCTGAAA | |
| PAb1 Light Chain Constant Region | CGGGCTGATGCTGCACCAACTGTATCCATCTTCCCACCATC CAGTGAGCAGTTAACATCTGGAGGTGCCTCAGTCGTGTGCT TCTTGAACAACTTCTACCCCAAAGACATCAATGTCAAGTGG AAGATTGATGGCAGTGAACGACAAAATGGCGTCCTGAACA GTTGGACTGATCAGGACAGCAAAGACAGCACCTACAGCAT GAGCAGCACCCTCACGTTGACCAAGGACGAGTATGAACGA CATAACAGCTATACCTGTGAGGCCACTCACAAGACATCAA CTTCACCCATTGTCAAGAGCTTCAACAGGAATGAGTGT | 79 |
| PAb1 Light Chain | MRCLAEFLGLLVLWIPGAIGDIVMTQAAPSVPVTPGESVSISC RSSKSLLHSNGNTYLYWFLQRPGQSPQLLIYRMSNLASGVPD RFSGSGSGTAFTLRISRVEAEDVGVYYCMQHLEYPLTFGAGT KLELKRADAAPTVSIFPPSSEQLTSGGASVVCFLNNFYPKDIN VKWKIDGSERQNGVLNSWTDQDSKDSTYSMSSTLTLTKDEYE RHNSYTCEATHKTSTSPIVKSFNRNEC | 80 |
| PAb1 Light Chain Leader | MRCLAEFLGLLVLWIPGAIG | 81 |
| PAb1 Light Chain FR1 | DIVMTQAAPSVPVTPGESVSISC | 82 |
| PAb1 Light Chain CDR1 | RSSKSLLHSNGNTYLY | 83 |
| PAb1 Light Chain FR2 | WFLQRPGQSPQLLIY | 84 |
| PAb1 Light Chain CDR2 | RMSNLAS | 85 |
| PAb1 Light Chain FR 3 | GVPDRFSGSGSGTAFTLRISRVEAEDVGVYYC | 86 |
| PAb1 Light Chain CDR3 | MQHLEYPLT | 87 |
| PAb1 Light Chain FR 4 | FGAGTKLELKR | 88 |
| PAb1 Light Chain Variable Region | DIVMTQAAPSVPVTPGESVSISCRSSKSLLHSNGNTYLYWFLQ RPGQSPQLLIYRMSNLASGVPDRFSGSGSGTAFTLRISRVEAE DVGVYYCMQHLEYPLTFGAGTKLELKR | 89 |
| PAb1 Light Chain Constant Region | ADAAPTVSIFPPSSEQLTSGGASVVCFLNNFYPKDINVKWKID GSERQNGVLNSWTDQDSKDSTYSMSSTLTLTKDEYERHNSYT CEATHKTSTSPIVKSFNRNEC | 90 |

What is claimed is:

1. A method of treating a cancer in a subject, comprising administering to the subject:
   (i) an antibody or antigen binding fragment comprising six complementarity determining regions (CDRs): CDRH1, CDRH2, CDRH3, CDRL1, CDRL2, and CDRL3, wherein
   (a) CDRH1 comprises a sequence as set forth in SEQ ID NO: 17, CDRH2 comprises a sequence as set forth in SEQ ID NO: 19, CDRH3 comprises a sequence as set forth in SEQ ID NO: 21, CDRL1 comprises a sequence as set forth in SEQ ID NO: 39, CDRL2 comprises a sequence as set forth in SEQ ID NO: 41, and CDRL3 comprises a sequence as set forth in SEQ ID NO: 43; or
   (b) CDRH1 comprises a sequence as set forth in SEQ ID NO: 61, CDRH2 comprises a sequence as set forth in SEQ ID NO: 63, CDRH3 comprises a sequence as set forth in SEQ ID NO: 65, CDRL1 comprises a sequence as set forth in SEQ ID NO: 83, CDRL2 comprises a sequence as set forth in SEQ ID NO: 85, and CDRL3 comprises a sequence as set forth in SEQ ID NO: 87; and
   (ii) an anti-cancer agent,
   wherein the cancer is characterized by expression of the amino acid sequence of SEQ ID NO: 2 on the surface of a cancer cell, thereby treating the cancer in the subject.

2. The method of claim 1, wherein (i) and (ii) are administered simultaneously.

3. The method of claim 1, wherein (i) and (ii) are administered sequentially.

4. The method of claim 1, wherein the anti-cancer agent is Paclitaxel Albumin-stabilized Nanoparticle Formulation, Fluorouracil, Everolimus, Erlotinib Hydrochloride, Gemcitabine Hydrochloride, Mitomycin C, Sunitinib Malate, Altretamine, Melphalan, Bevacizumab, Carboplatin, Cyclophosphamide, Cisplatin, Doxorubicin Hydrochloride, Doxorubicin Hydrochloride Liposome, Topotecan Hydrochloride, Olaparib, Niraparib Tosylate Monohydrate, Paclitaxel, Rucaparib Camsylate, or Thiotepa.

5. The method of claim 1, wherein the anti-cancer agent is a chemotherapeutic agent.

6. The method of claim 5, wherein the chemotherapeutic agent is gemcitabine.

7. The method of claim 1, wherein the antibody or antigen binding fragment specifically binds the amino acid sequence set forth in SEQ ID NO: 2.

8. The method of claim 1, wherein the antibody or antigen binding fragment comprises a heavy chain variable region and a light chain variable region comprising the amino acid sequences set forth in;
   (a) SEQ ID NOs: 23 and 45, respectively; or
   (b) SEQ ID NOs: 67 and 89, respectively.

9. The method of claim 1, wherein the cancer is ovarian cancer, esophageal cancer, head and neck squamous cell carcinoma, or pancreatic cancer.

10. A method of treating a cancer in a subject that is receiving an anti-cancer agent, comprising administering to the subject an antibody or antigen binding fragment comprising six complementarity determining regions (CDRs): CDRH1, CDRH2, CDRH3, CDRL1, CDRL2, and CDRL3, wherein
    (a) CDRH1 comprises a sequence as set forth in SEQ ID NO: 17, CDRH2 comprises a sequence as set forth in SEQ ID NO: 19, CDRH3 comprises a sequence as set forth in SEQ ID NO: 21, CDRL1 comprises a sequence as set forth in SEQ ID NO: 39, CDRL2 comprises a sequence as set forth in SEQ ID NO: 41, and CDRL3 comprises a sequence as set forth in SEQ ID NO: 43; or
    (b) CDRH1 comprises a sequence as set forth in SEQ ID NO: 61, CDRH2 comprises a sequence as set forth in SEQ ID NO: 63, CDRH3 comprises a sequence as set forth in SEQ ID NO: 65, CDRL1 comprises a sequence as set forth in SEQ ID NO: 83, CDRL2 comprises a sequence as set forth in SEQ ID NO: 85, and CDRL3 comprises a sequence as set forth in SEQ ID NO: 87,
    wherein the cancer is characterized by expression of the amino acid sequence of SEQ ID NO: 2 on the surface of a cancer cell.

11. The method of claim 10, wherein the anti-cancer agent is a chemotherapeutic agent.

12. The method of claim 11, wherein the chemotherapeutic agent is gemcitabine.

13. The method of claim 10, wherein the antibody or antigen binding fragment comprises a heavy chain variable region and a light chain variable region comprising the amino acid sequences set forth in:
    (a) SEQ ID NOs: 23 and 45, respectively; or
    (b) SEQ ID NOs: 67 and 89, respectively.

14. A method of treating a cancer in a subject that is receiving an antibody or antigen binding fragment comprising six complementarity determining regions (CDRs): CDRH1, CDRH2, CDRH3, CDRL1, CDRL2, and CDRL3, wherein (a) CDRH1 comprises a sequence as set forth in SEQ ID NO: 17, CDRH2 comprises a sequence as set forth in SEQ ID NO: 19, CDRH3 comprises a sequence as set forth in SEQ ID NO: 21, CDRL1 comprises a sequence as set forth in SEQ ID NO: 39, CDRL2 comprises a sequence as set forth in SEQ ID NO: 41, and CDRL3 comprises a sequence as set forth in SEQ ID NO: 43; or (b) CDRH1 comprises a sequence as set forth in SEQ ID NO: 61, CDRH2 comprises a sequence as set forth in SEQ ID NO: 63, CDRH3 comprises a sequence as set forth in SEQ ID NO: 65, CDRL1 comprises a sequence as set forth in SEQ ID NO: 83, CDRL2 comprises a sequence as set forth in SEQ ID NO: 85, and CDRL3 comprises a sequence as set forth in SEQ ID NO: 87, comprising administering to the subject an anti-cancer agent, and wherein the cancer is characterized by expression of the amino acid sequence of SEQ ID NO: 2 on the surface of a cancer cell.

15. The method of claim 14, wherein the anti-cancer agent is a chemotherapeutic agent.

16. The method of claim 15, wherein the chemotherapeutic agent is gemcitabine.

17. The method of claim 14, wherein the antibody or antigen binding fragment comprises a heavy chain variable region and a light chain variable region comprising the amino acid sequences set forth in:

(a) SEQ ID NOs: 23 and 45, respectively; or (b) SEQ ID NOs: 67 and 89, respectively.

18. The method of claim 9, wherein the pancreatic cancer is pancreatic ductal adenocarcinoma (PDAC).

\* \* \* \* \*

SEQUENCE LISTING

<160> NUMBER OF SEQ ID NOS: 91

<210> SEQ ID NO 1
<211> LENGTH: 4684
<212> TYPE: PRT
<213> ORGANISM: Homo sapiens

<400> SEQUENCE: 1

Met Val Ala Gly Met Leu Met Pro Arg Asp Gln Leu Arg Ala Ile Tyr
1               5                   10                  15

Glu Val Leu Phe Arg Glu Gly Val Met Val Ala Lys Lys Asp Arg Arg
            20                  25                  30

```
Pro Arg Ser Leu His Pro His Val Pro Gly Val Thr Asn Leu Gln Val
         35                  40                  45

Met Arg Ala Met Ala Ser Leu Arg Ala Arg Gly Leu Val Arg Glu Thr
 50                  55                  60

Phe Ala Trp Cys His Phe Tyr Trp Tyr Leu Thr Asn Glu Gly Ile Ala
 65                  70                  75                  80

His Leu Arg Gln Tyr Leu His Leu Pro Pro Glu Ile Val Pro Ala Ser
                 85                  90                  95

Leu Gln Arg Val Arg Arg Pro Val Ala Met Val Met Pro Ala Arg Arg
                100                 105                 110

Thr Pro His Val Gln Ala Val Gln Gly Pro Leu Gly Ser Pro Pro Lys
            115                 120                 125

Arg Gly Pro Leu Pro Thr Glu Glu Gln Arg Val Tyr Arg Arg Lys Glu
        130                 135                 140

Leu Glu Glu Val Ser Pro Glu Thr Pro Val Val Pro Ala Thr Thr Gln
145                 150                 155                 160

Arg Thr Leu Ala Arg Pro Gly Pro Glu Pro Ala Pro Ala Thr Asp Glu
                165                 170                 175

Arg Asp Arg Val Gln Lys Lys Thr Phe Thr Lys Trp Val Asn Lys His
            180                 185                 190

Leu Ile Lys Ala Gln Arg His Ile Ser Asp Leu Tyr Glu Asp Leu Arg
        195                 200                 205

Asp Gly His Asn Leu Ile Ser Leu Leu Glu Val Leu Ser Gly Asp Ser
    210                 215                 220

Leu Pro Arg Glu Lys Gly Arg Met Arg Phe His Lys Leu Gln Asn Val
225                 230                 235                 240

Gln Ile Ala Leu Asp Tyr Leu Arg His Arg Gln Val Lys Leu Val Asn
                245                 250                 255

Ile Arg Asn Asp Asp Ile Ala Asp Gly Asn Pro Lys Leu Thr Leu Gly
            260                 265                 270

Leu Ile Trp Thr Ile Ile Leu His Phe Gln Ile Ser Asp Ile Gln Val
        275                 280                 285

Ser Gly Gln Ser Glu Asp Met Thr Ala Lys Glu Lys Leu Leu Leu Trp
    290                 295                 300

Ser Gln Arg Met Val Glu Gly Tyr Gln Gly Leu Arg Cys Asp Asn Phe
305                 310                 315                 320

Thr Ser Ser Trp Arg Asp Gly Arg Leu Phe Asn Ala Ile Ile His Arg
                325                 330                 335

His Lys Pro Leu Leu Ile Asp Met Asn Lys Val Tyr Arg Gln Thr Asn
            340                 345                 350

Leu Glu Asn Leu Asp Gln Ala Phe Ser Val Ala Glu Arg Asp Leu Gly
        355                 360                 365

Val Thr Arg Leu Leu Asp Pro Glu Asp Val Asp Val Pro Gln Pro Asp
    370                 375                 380

Glu Lys Ser Ile Ile Thr Tyr Val Ser Ser Leu Tyr Asp Ala Met Pro
385                 390                 395                 400

Arg Val Pro Asp Val Gln Asp Gly Val Arg Ala Asn Glu Leu Gln Leu
                405                 410                 415

Arg Trp Gln Glu Tyr Arg Glu Leu Val Leu Leu Leu Gln Trp Met
            420                 425                 430

Arg His His Thr Ala Ala Phe Glu Glu Arg Arg Phe Pro Ser Ser Phe
        435                 440                 445

Glu Glu Ile Glu Ile Leu Trp Ser Gln Phe Leu Lys Phe Lys Glu Met
```

-continued

```
            450                 455                 460
Glu Leu Pro Ala Lys Glu Ala Asp Lys Asn Arg Ser Lys Gly Ile Tyr
465                 470                 475                 480
Gln Ser Leu Glu Gly Ala Val Gln Ala Gly Gln Leu Lys Val Pro Pro
                    485                 490                 495
Gly Tyr His Pro Leu Asp Val Glu Lys Glu Trp Gly Lys Leu His Val
                500                 505                 510
Ala Ile Leu Glu Arg Glu Lys Gln Leu Arg Ser Glu Phe Glu Arg Leu
                515                 520                 525
Glu Cys Leu Gln Arg Ile Val Thr Lys Leu Gln Met Glu Ala Gly Leu
            530                 535                 540
Cys Glu Glu Gln Leu Asn Gln Ala Asp Ala Leu Leu Gln Ser Asp Val
545                 550                 555                 560
Arg Leu Leu Ala Ala Gly Lys Val Pro Gln Arg Ala Gly Glu Val Glu
                    565                 570                 575
Arg Asp Leu Asp Lys Ala Asp Ser Met Ile Arg Leu Leu Phe Asn Asp
                580                 585                 590
Val Gln Thr Leu Lys Asp Gly Arg His Pro Gln Gly Glu Gln Met Tyr
                595                 600                 605
Arg Arg Val Tyr Arg Leu His Glu Arg Leu Val Ala Ile Arg Thr Glu
610                 615                 620
Tyr Asn Leu Arg Leu Lys Ala Gly Val Ala Ala Pro Ala Thr Gln Val
625                 630                 635                 640
Ala Gln Val Thr Leu Gln Ser Val Gln Arg Arg Pro Glu Leu Glu Asp
                    645                 650                 655
Ser Thr Leu Arg Tyr Leu Gln Asp Leu Leu Ala Trp Val Glu Glu Asn
                    660                 665                 670
Gln His Arg Val Asp Gly Ala Glu Trp Gly Val Asp Leu Pro Ser Val
                675                 680                 685
Glu Ala Gln Leu Gly Ser His Arg Gly Leu His Gln Ser Ile Glu Glu
                690                 695                 700
Phe Arg Ala Lys Ile Glu Arg Ala Arg Ser Asp Glu Gly Gln Leu Ser
705                 710                 715                 720
Pro Ala Thr Arg Gly Ala Tyr Arg Asp Cys Leu Gly Arg Leu Asp Leu
                    725                 730                 735
Gln Tyr Ala Lys Leu Leu Asn Ser Ser Lys Ala Arg Leu Arg Ser Leu
                740                 745                 750
Glu Ser Leu His Ser Phe Val Ala Ala Ala Thr Lys Glu Leu Met Trp
                755                 760                 765
Leu Asn Glu Lys Glu Glu Glu Val Gly Phe Asp Trp Ser Asp Arg
                770                 775                 780
Asn Thr Asn Met Thr Ala Lys Lys Glu Ser Tyr Ser Ala Leu Met Arg
785                 790                 795                 800
Glu Leu Glu Leu Lys Glu Lys Lys Ile Lys Glu Leu Gln Asn Ala Gly
                    805                 810                 815
Asp Arg Leu Leu Arg Glu Asp His Pro Ala Arg Pro Thr Val Glu Ser
                820                 825                 830
Phe Gln Ala Ala Leu Gln Thr Gln Trp Ser Trp Met Leu Gln Leu Cys
            835                 840                 845
Cys Cys Ile Glu Ala His Leu Lys Glu Asn Ala Ala Tyr Phe Gln Phe
            850                 855                 860
Phe Ser Asp Val Arg Glu Ala Glu Gly Gln Leu Gln Lys Leu Gln Glu
865                 870                 875                 880
```

```
Ala Leu Arg Arg Lys Tyr Ser Cys Asp Arg Ser Ala Thr Val Thr Arg
            885                 890                 895

Leu Glu Asp Leu Leu Gln Asp Ala Gln Asp Glu Lys Glu Gln Leu Asn
        900                 905                 910

Glu Tyr Lys Gly His Leu Ser Gly Leu Ala Lys Arg Ala Lys Ala Val
        915                 920                 925

Val Gln Leu Lys Pro Arg His Pro Ala His Pro Met Arg Gly Arg Leu
        930                 935                 940

Pro Leu Leu Ala Val Cys Asp Tyr Lys Gln Val Glu Val Thr Val His
945                 950                 955                 960

Lys Gly Asp Glu Cys Gln Leu Val Gly Pro Ala Gln Pro Ser His Trp
                965                 970                 975

Lys Val Leu Ser Ser Ser Gly Ser Glu Ala Ala Val Pro Ser Val Cys
                980                 985                 990

Phe Leu Val Pro Pro Asn Gln Glu Ala Gln Glu Ala Val Thr Arg
            995                 1000                1005

Leu Glu Ala Gln His Gln Ala Leu Val Thr Leu Trp His Gln Leu
    1010                1015                1020

His Val Asp Met Lys Ser Leu Leu Ala Trp Gln Ser Leu Arg Arg
    1025                1030                1035

Asp Val Gln Leu Ile Arg Ser Trp Ser Leu Ala Thr Phe Arg Thr
    1040                1045                1050

Leu Lys Pro Glu Glu Gln Arg Gln Ala Leu His Ser Leu Glu Leu
    1055                1060                1065

His Tyr Gln Ala Phe Leu Arg Asp Ser Gln Asp Ala Gly Gly Phe
    1070                1075                1080

Gly Pro Glu Asp Arg Leu Met Ala Glu Arg Glu Tyr Gly Ser Cys
    1085                1090                1095

Ser His His Tyr Gln Gln Leu Leu Gln Ser Leu Glu Gln Gly Ala
    1100                1105                1110

Gln Glu Glu Ser Arg Cys Gln Arg Cys Ile Ser Glu Leu Lys Asp
    1115                1120                1125

Ile Arg Leu Gln Leu Glu Ala Cys Glu Thr Arg Thr Val His Arg
    1130                1135                1140

Leu Arg Leu Pro Leu Asp Lys Glu Pro Ala Arg Glu Cys Ala Gln
    1145                1150                1155

Arg Ile Ala Glu Gln Gln Lys Ala Gln Ala Glu Val Glu Gly Leu
    1160                1165                1170

Gly Lys Gly Val Ala Arg Leu Ser Ala Glu Ala Glu Lys Val Leu
    1175                1180                1185

Ala Leu Pro Glu Pro Ser Pro Ala Ala Pro Thr Leu Arg Ser Glu
    1190                1195                1200

Leu Glu Leu Thr Leu Gly Lys Leu Glu Gln Val Arg Ser Leu Ser
    1205                1210                1215

Ala Ile Tyr Leu Glu Lys Leu Lys Thr Ile Ser Leu Val Ile Arg
    1220                1225                1230

Gly Thr Gln Gly Ala Glu Glu Val Leu Arg Ala His Glu Glu Gln
    1235                1240                1245

Leu Lys Glu Ala Gln Ala Val Pro Ala Thr Leu Pro Glu Leu Glu
    1250                1255                1260

Ala Thr Lys Ala Ser Leu Lys Lys Leu Arg Ala Gln Ala Glu Ala
    1265                1270                1275
```

-continued

```
Gln Gln Pro Thr Phe Asp Ala Leu Arg Asp Glu Leu Arg Gly Ala
    1280                1285                1290

Gln Glu Val Gly Glu Arg Leu Gln Gln Arg His Gly Glu Arg Asp
    1295                1300                1305

Val Glu Val Glu Arg Trp Arg Glu Arg Val Ala Gln Leu Leu Glu
    1310                1315                1320

Arg Trp Gln Ala Val Leu Ala Gln Thr Asp Val Arg Gln Arg Glu
    1325                1330                1335

Leu Glu Gln Leu Gly Arg Gln Leu Arg Tyr Tyr Arg Glu Ser Ala
    1340                1345                1350

Asp Pro Leu Gly Ala Trp Leu Gln Asp Ala Arg Arg Gln Glu
    1355                1360                1365

Gln Ile Gln Ala Met Pro Leu Ala Asp Ser Gln Ala Val Arg Glu
    1370                1375                1380

Gln Leu Arg Gln Glu Gln Ala Leu Leu Glu Glu Ile Glu Arg His
    1385                1390                1395

Gly Glu Lys Val Glu Glu Cys Gln Arg Phe Ala Lys Gln Tyr Ile
    1400                1405                1410

Asn Ala Ile Lys Asp Tyr Glu Leu Gln Leu Val Thr Tyr Lys Ala
    1415                1420                1425

Gln Leu Glu Pro Val Ala Ser Pro Ala Lys Lys Pro Lys Val Gln
    1430                1435                1440

Ser Gly Ser Glu Ser Val Ile Gln Glu Tyr Val Asp Leu Arg Thr
    1445                1450                1455

His Tyr Ser Glu Leu Thr Thr Leu Thr Ser Gln Tyr Ile Lys Phe
    1460                1465                1470

Ile Ser Glu Thr Leu Arg Arg Met Glu Glu Glu Arg Leu Ala
    1475                1480                1485

Glu Gln Gln Arg Ala Glu Glu Arg Glu Arg Leu Ala Glu Val Glu
    1490                1495                1500

Ala Ala Leu Glu Lys Gln Arg Gln Leu Ala Glu Ala His Ala Gln
    1505                1510                1515

Ala Lys Ala Gln Ala Glu Arg Glu Ala Lys Glu Leu Gln Gln Arg
    1520                1525                1530

Met Gln Glu Glu Val Val Arg Glu Glu Ala Ala Val Asp Ala
    1535                1540                1545

Gln Gln Gln Lys Arg Ser Ile Gln Glu Glu Leu Gln Gln Leu Arg
    1550                1555                1560

Gln Ser Ser Glu Ala Glu Ile Gln Ala Lys Ala Arg Gln Ala Glu
    1565                1570                1575

Ala Ala Glu Arg Ser Arg Leu Arg Ile Glu Glu Glu Ile Arg Val
    1580                1585                1590

Val Arg Leu Gln Leu Glu Ala Thr Glu Arg Gln Arg Gly Gly Ala
    1595                1600                1605

Glu Gly Glu Leu Gln Ala Leu Arg Ala Arg Ala Glu Glu Ala Glu
    1610                1615                1620

Ala Gln Lys Arg Gln Ala Gln Glu Glu Ala Glu Arg Leu Arg Arg
    1625                1630                1635

Gln Val Gln Asp Glu Ser Gln Arg Lys Arg Gln Ala Glu Val Glu
    1640                1645                1650

Leu Ala Ser Arg Val Lys Ala Glu Ala Glu Ala Ala Arg Glu Lys
    1655                1660                1665

Gln Arg Ala Leu Gln Ala Leu Glu Glu Leu Arg Leu Gln Ala Glu
```

```
            1670                1675                1680

Glu Ala Glu Arg Arg Leu Arg Gln Ala Glu Val Glu Arg Ala Arg
            1685                1690                1695

Gln Val Gln Val Ala Leu Glu Thr Ala Gln Arg Ser Ala Glu Ala
            1700                1705                1710

Glu Leu Gln Ser Lys Arg Ala Ser Phe Ala Glu Lys Thr Ala Gln
            1715                1720                1725

Leu Glu Arg Ser Leu Gln Glu Glu His Val Ala Val Ala Gln Leu
            1730                1735                1740

Arg Glu Glu Ala Glu Arg Ala Gln Gln Gln Ala Glu Ala Glu
            1745                1750                1755

Arg Ala Arg Glu Glu Ala Glu Arg Glu Leu Glu Arg Trp Gln Leu
            1760                1765                1770

Lys Ala Asn Glu Ala Leu Arg Leu Arg Leu Gln Ala Glu Glu Val
            1775                1780                1785

Ala Gln Gln Lys Ser Leu Ala Gln Ala Glu Ala Glu Lys Gln Lys
            1790                1795                1800

Glu Glu Ala Glu Arg Glu Ala Arg Arg Arg Gly Lys Ala Glu Glu
            1805                1810                1815

Gln Ala Val Arg Gln Arg Glu Leu Ala Glu Gln Glu Leu Glu Lys
            1820                1825                1830

Gln Arg Gln Leu Ala Glu Gly Thr Ala Gly Gln Arg Leu Ala Ala
            1835                1840                1845

Glu Gln Glu Leu Ile Arg Leu Arg Ala Glu Thr Glu Gln Gly Glu
            1850                1855                1860

Gln Gln Arg Gln Leu Leu Glu Glu Leu Ala Arg Leu Gln Arg
            1865                1870                1875

Glu Ala Ala Ala Thr Gln Lys Arg Gln Glu Leu Glu Ala Glu
            1880                1885                1890

Leu Ala Lys Val Arg Ala Glu Met Glu Val Leu Leu Ala Ser Lys
            1895                1900                1905

Ala Arg Ala Glu Glu Glu Ser Arg Ser Thr Ser Glu Lys Ser Lys
            1910                1915                1920

Gln Arg Leu Glu Ala Glu Ala Gly Arg Phe Arg Glu Leu Ala Glu
            1925                1930                1935

Glu Ala Ala Arg Leu Arg Ala Leu Ala Glu Glu Ala Lys Arg Gln
            1940                1945                1950

Arg Gln Leu Ala Glu Glu Asp Ala Ala Arg Gln Arg Ala Glu Ala
            1955                1960                1965

Glu Arg Val Leu Ala Glu Lys Leu Ala Ala Ile Gly Glu Ala Thr
            1970                1975                1980

Arg Leu Lys Thr Glu Ala Glu Ile Ala Leu Lys Glu Lys Glu Ala
            1985                1990                1995

Glu Asn Glu Arg Leu Arg Arg Leu Ala Glu Asp Glu Ala Phe Gln
            2000                2005                2010

Arg Arg Arg Leu Glu Glu Gln Ala Ala Gln His Lys Ala Asp Ile
            2015                2020                2025

Glu Glu Arg Leu Ala Gln Leu Arg Lys Ala Ser Asp Ser Glu Leu
            2030                2035                2040

Glu Arg Gln Lys Gly Leu Val Glu Asp Thr Leu Arg Gln Arg Arg
            2045                2050                2055

Gln Val Glu Glu Glu Ile Leu Ala Leu Lys Ala Ser Phe Glu Lys
            2060                2065                2070
```

```
Ala Ala Ala Gly Lys Ala Glu Leu Glu Leu Gly Arg Ile
2075            2080            2085

Arg Ser Asn Ala Glu Asp Thr Leu Arg Ser Lys Glu Gln Ala Glu
2090            2095            2100

Leu Glu Ala Ala Arg Gln Arg Gln Leu Ala Ala Glu Glu Arg
2105            2110            2115

Arg Arg Arg Glu Ala Glu Arg Val Gln Lys Ser Leu Ala Ala
2120            2125            2130

Glu Glu Glu Ala Ala Arg Gln Arg Lys Ala Ala Leu Glu Glu Val
2135            2140            2145

Glu Arg Leu Lys Ala Lys Val Glu Glu Ala Arg Arg Leu Arg Glu
2150            2155            2160

Arg Ala Glu Gln Glu Ser Ala Arg Gln Leu Gln Leu Ala Gln Glu
2165            2170            2175

Ala Ala Gln Lys Arg Leu Gln Ala Glu Glu Lys Ala His Ala Phe
2180            2185            2190

Ala Val Gln Gln Lys Glu Gln Glu Leu Gln Gln Thr Leu Gln Gln
2195            2200            2205

Glu Gln Ser Val Leu Asp Gln Leu Arg Gly Glu Ala Glu Ala Ala
2210            2215            2220

Arg Arg Ala Ala Glu Glu Ala Glu Glu Ala Arg Val Gln Ala Glu
2225            2230            2235

Arg Glu Ala Ala Gln Ser Arg Arg Gln Val Glu Glu Ala Glu Arg
2240            2245            2250

Leu Lys Gln Ser Ala Glu Glu Gln Ala Gln Ala Arg Ala Gln Ala
2255            2260            2265

Gln Ala Ala Ala Glu Lys Leu Arg Lys Glu Ala Glu Gln Glu Ala
2270            2275            2280

Ala Arg Arg Ala Gln Ala Glu Gln Ala Ala Leu Arg Gln Lys Gln
2285            2290            2295

Ala Ala Asp Ala Glu Met Glu Lys His Lys Lys Phe Ala Glu Gln
2300            2305            2310

Thr Leu Arg Gln Lys Ala Gln Val Glu Gln Glu Leu Thr Thr Leu
2315            2320            2325

Arg Leu Gln Leu Glu Glu Thr Asp His Gln Lys Asn Leu Leu Asp
2330            2335            2340

Glu Glu Leu Gln Arg Leu Lys Ala Glu Ala Thr Glu Ala Ala Arg
2345            2350            2355

Gln Arg Ser Gln Val Glu Glu Glu Leu Phe Ser Val Arg Val Gln
2360            2365            2370

Met Glu Glu Leu Ser Lys Leu Lys Ala Arg Ile Glu Ala Glu Asn
2375            2380            2385

Arg Ala Leu Ile Leu Arg Asp Lys Asp Asn Thr Gln Arg Phe Leu
2390            2395            2400

Gln Glu Glu Ala Glu Lys Met Lys Gln Val Ala Glu Glu Ala Ala
2405            2410            2415

Arg Leu Ser Val Ala Ala Gln Glu Ala Ala Arg Leu Arg Gln Leu
2420            2425            2430

Ala Glu Glu Asp Leu Ala Gln Gln Arg Ala Leu Ala Glu Lys Met
2435            2440            2445

Leu Lys Glu Lys Met Gln Ala Val Gln Glu Ala Thr Arg Leu Lys
2450            2455            2460
```

-continued

Ala Glu Ala Glu Leu Leu Gln Gln Lys Glu Leu Ala Gln Glu
2465                2470                2475

Gln Ala Arg Arg Leu Gln Glu Asp Lys Glu Gln Met Ala Gln
2480                2485                2490

Leu Ala Glu Glu Thr Gln Gly Phe Gln Arg Thr Leu Glu Ala Glu
2495                2500                2505

Arg Gln Arg Gln Leu Glu Met Ser Ala Glu Ala Glu Arg Leu Lys
2510                2515                2520

Leu Arg Val Ala Glu Met Ser Arg Ala Gln Ala Arg Ala Glu Glu
2525                2530                2535

Asp Ala Gln Arg Phe Arg Lys Gln Ala Glu Glu Ile Gly Glu Lys
2540                2545                2550

Leu His Arg Thr Glu Leu Ala Thr Gln Glu Lys Val Thr Leu Val
2555                2560                2565

Gln Thr Leu Glu Ile Gln Arg Gln Gln Ser Asp His Asp Ala Glu
2570                2575                2580

Arg Leu Arg Glu Ala Ile Ala Glu Leu Glu Arg Glu Lys Glu Lys
2585                2590                2595

Leu Gln Gln Glu Ala Lys Leu Leu Gln Leu Lys Ser Glu Glu Met
2600                2605                2610

Gln Thr Val Gln Gln Glu Gln Leu Leu Gln Glu Thr Gln Ala Leu
2615                2620                2625

Gln Gln Ser Phe Leu Ser Glu Lys Asp Ser Leu Leu Gln Arg Glu
2630                2635                2640

Arg Phe Ile Glu Gln Glu Lys Ala Lys Leu Glu Gln Leu Phe Gln
2645                2650                2655

Asp Glu Val Ala Lys Ala Gln Gln Leu Arg Glu Glu Gln Gln Arg
2660                2665                2670

Gln Gln Gln Gln Met Glu Gln Glu Arg Gln Arg Leu Val Ala Ser
2675                2680                2685

Met Glu Glu Ala Arg Arg Arg Gln His Glu Ala Glu Glu Gly Val
2690                2695                2700

Arg Arg Lys Gln Glu Glu Leu Gln Gln Leu Glu Gln Gln Arg Arg
2705                2710                2715

Gln Gln Glu Glu Leu Leu Ala Glu Glu Asn Gln Arg Leu Arg Glu
2720                2725                2730

Gln Leu Gln Leu Leu Glu Glu Gln His Arg Ala Ala Leu Ala His
2735                2740                2745

Ser Glu Glu Val Thr Ala Ser Gln Val Ala Ala Thr Lys Thr Leu
2750                2755                2760

Pro Asn Gly Arg Asp Ala Leu Asp Gly Pro Ala Ala Glu Ala Glu
2765                2770                2775

Pro Glu His Ser Phe Asp Gly Leu Arg Arg Lys Val Ser Ala Gln
2780                2785                2790

Arg Leu Gln Glu Ala Gly Ile Leu Ser Ala Glu Glu Leu Gln Arg
2795                2800                2805

Leu Ala Gln Gly His Thr Thr Val Asp Glu Leu Ala Arg Arg Glu
2810                2815                2820

Asp Val Arg His Tyr Leu Gln Gly Arg Ser Ser Ile Ala Gly Leu
2825                2830                2835

Leu Leu Lys Ala Thr Asn Glu Lys Leu Ser Val Tyr Ala Ala Leu
2840                2845                2850

Gln Arg Gln Leu Leu Ser Pro Gly Thr Ala Leu Ile Leu Leu Glu

```
                 2855                2860                2865
Ala Gln Ala Ala Ser Gly Phe Leu Leu Asp Pro Val Arg Asn Arg
                 2870                2875                2880
Arg Leu Thr Val Asn Glu Ala Val Lys Glu Gly Val Val Gly Pro
                 2885                2890                2895
Glu Leu His His Lys Leu Leu Ser Ala Glu Arg Ala Val Thr Gly
                 2900                2905                2910
Tyr Lys Asp Pro Tyr Thr Gly Gln Gln Ile Ser Leu Phe Gln Ala
                 2915                2920                2925
Met Gln Lys Gly Leu Ile Val Arg Glu His Gly Ile Arg Leu Leu
                 2930                2935                2940
Glu Ala Gln Ile Ala Thr Gly Gly Val Ile Asp Pro Val His Ser
                 2945                2950                2955
His Arg Val Pro Val Asp Val Ala Tyr Arg Arg Gly Tyr Phe Asp
                 2960                2965                2970
Glu Glu Met Asn Arg Val Leu Ala Asp Pro Ser Asp Asp Thr Lys
                 2975                2980                2985
Gly Phe Phe Asp Pro Asn Thr His Glu Asn Leu Thr Tyr Leu Gln
                 2990                2995                3000
Leu Leu Glu Arg Cys Val Glu Asp Pro Glu Thr Gly Leu Cys Leu
                 3005                3010                3015
Leu Pro Leu Thr Asp Lys Ala Ala Lys Gly Gly Glu Leu Val Tyr
                 3020                3025                3030
Thr Asp Ser Glu Ala Arg Asp Val Phe Glu Lys Ala Thr Val Ser
                 3035                3040                3045
Ala Pro Phe Gly Lys Phe Gln Gly Lys Thr Val Thr Ile Trp Glu
                 3050                3055                3060
Ile Ile Asn Ser Glu Tyr Phe Thr Ala Glu Gln Arg Arg Asp Leu
                 3065                3070                3075
Leu Arg Gln Phe Arg Thr Gly Arg Ile Thr Val Glu Lys Ile Ile
                 3080                3085                3090
Lys Ile Ile Ile Thr Val Val Glu Glu Gln Glu Gln Lys Gly Arg
                 3095                3100                3105
Leu Cys Phe Glu Gly Leu Arg Ser Leu Val Pro Ala Ala Glu Leu
                 3110                3115                3120
Leu Glu Ser Arg Val Ile Asp Arg Glu Leu Tyr Gln Gln Leu Gln
                 3125                3130                3135
Arg Gly Glu Arg Ser Val Arg Asp Val Ala Glu Val Asp Thr Val
                 3140                3145                3150
Arg Arg Ala Leu Arg Gly Ala Asn Val Ile Ala Gly Val Trp Leu
                 3155                3160                3165
Glu Glu Ala Gly Gln Lys Leu Ser Ile Tyr Asn Ala Leu Lys Lys
                 3170                3175                3180
Asp Leu Leu Pro Ser Asp Met Ala Val Ala Leu Leu Glu Ala Gln
                 3185                3190                3195
Ala Gly Thr Gly His Ile Ile Asp Pro Ala Thr Ser Ala Arg Leu
                 3200                3205                3210
Thr Val Asp Glu Ala Val Arg Ala Gly Leu Val Gly Pro Glu Phe
                 3215                3220                3225
His Glu Lys Leu Leu Ser Ala Glu Lys Ala Val Thr Gly Tyr Arg
                 3230                3235                3240
Asp Pro Tyr Thr Gly Gln Ser Val Ser Leu Phe Gln Ala Leu Lys
                 3245                3250                3255
```

```
Lys Gly Leu Ile Pro Arg Glu Gln Gly Leu Arg Leu Leu Asp Ala
3260              3265              3270

Gln Leu Ser Thr Gly Gly Ile Val Asp Pro Ser Lys Ser His Arg
3275              3280              3285

Val Pro Leu Asp Val Ala Cys Ala Arg Gly Cys Leu Asp Glu Glu
3290              3295              3300

Thr Ser Arg Ala Leu Ser Ala Pro Arg Ala Asp Ala Lys Ala Tyr
3305              3310              3315

Ser Asp Pro Ser Thr Gly Glu Pro Ala Thr Tyr Gly Glu Leu Gln
3320              3325              3330

Gln Arg Cys Arg Pro Asp Gln Leu Thr Gly Leu Ser Leu Leu Pro
3335              3340              3345

Leu Ser Glu Lys Ala Ala Arg Ala Arg Gln Glu Glu Leu Tyr Ser
3350              3355              3360

Glu Leu Gln Ala Arg Glu Thr Phe Glu Lys Thr Pro Val Glu Val
3365              3370              3375

Pro Val Gly Gly Phe Lys Gly Arg Thr Val Thr Val Trp Glu Leu
3380              3385              3390

Ile Ser Ser Glu Tyr Phe Thr Ala Glu Gln Arg Gln Glu Leu Leu
3395              3400              3405

Arg Gln Phe Arg Thr Gly Lys Val Thr Val Glu Lys Val Ile Lys
3410              3415              3420

Ile Leu Ile Thr Ile Val Glu Glu Val Glu Thr Leu Arg Gln Glu
3425              3430              3435

Arg Leu Ser Phe Ser Gly Leu Arg Ala Pro Val Pro Ala Ser Glu
3440              3445              3450

Leu Leu Ala Ser Gly Val Leu Ser Arg Ala Gln Phe Glu Gln Leu
3455              3460              3465

Lys Asp Gly Lys Thr Thr Val Lys Asp Leu Ser Glu Leu Gly Ser
3470              3475              3480

Val Arg Thr Leu Leu Gln Gly Ser Gly Cys Leu Ala Gly Ile Tyr
3485              3490              3495

Leu Glu Asp Thr Lys Glu Lys Val Ser Ile Tyr Glu Ala Met Arg
3500              3505              3510

Arg Gly Leu Leu Arg Ala Thr Thr Ala Ala Leu Leu Glu Ala
3515              3520              3525

Gln Ala Ala Thr Gly Phe Leu Val Asp Pro Val Arg Asn Gln Arg
3530              3535              3540

Leu Tyr Val His Glu Ala Val Lys Ala Gly Val Val Gly Pro Glu
3545              3550              3555

Leu His Glu Gln Leu Leu Ser Ala Glu Lys Ala Val Thr Gly Tyr
3560              3565              3570

Arg Asp Pro Tyr Ser Gly Ser Thr Ile Ser Leu Phe Gln Ala Met
3575              3580              3585

Gln Lys Gly Leu Val Leu Arg Gln His Gly Ile Arg Leu Leu Glu
3590              3595              3600

Ala Gln Ile Ala Thr Gly Gly Ile Ile Asp Pro Val His Ser His
3605              3610              3615

Arg Val Pro Val Asp Val Ala Tyr Gln Arg Gly Tyr Phe Ser Glu
3620              3625              3630

Glu Met Asn Arg Val Leu Ala Asp Pro Ser Asp Asp Thr Lys Gly
3635              3640              3645
```

-continued

```
Phe Phe Asp Pro Asn Thr His Glu Asn Leu Thr Tyr Arg Gln Leu
3650                3655                3660

Leu Glu Arg Cys Val Glu Asp Pro Glu Thr Gly Leu Arg Leu Leu
3665                3670                3675

Pro Leu Lys Gly Ala Glu Lys Ala Glu Val Val Glu Thr Thr Gln
3680                3685                3690

Val Tyr Thr Glu Glu Thr Arg Arg Ala Phe Glu Glu Thr Gln
3695                3700                3705

Ile Asp Ile Pro Gly Gly Gly Ser His Gly Gly Ser Thr Met Ser
3710                3715                3720

Leu Trp Glu Val Met Gln Ser Asp Leu Ile Pro Glu Glu Gln Arg
3725                3730                3735

Ala Gln Leu Met Ala Asp Phe Gln Ala Gly Arg Val Thr Lys Glu
3740                3745                3750

Arg Met Ile Ile Ile Ile Ile Glu Ile Ile Glu Lys Thr Glu Ile
3755                3760                3765

Ile Arg Gln Gln Gly Leu Ala Ser Tyr Asp Tyr Val Arg Arg Arg
3770                3775                3780

Leu Thr Ala Glu Asp Leu Phe Glu Ala Arg Ile Ile Ser Leu Glu
3785                3790                3795

Thr Tyr Asn Leu Leu Arg Glu Gly Thr Arg Ser Leu Arg Glu Ala
3800                3805                3810

Leu Glu Ala Glu Ser Ala Trp Cys Tyr Leu Tyr Gly Thr Gly Ser
3815                3820                3825

Val Ala Gly Val Tyr Leu Pro Gly Ser Arg Gln Thr Leu Ser Ile
3830                3835                3840

Tyr Gln Ala Leu Lys Lys Gly Leu Leu Ser Ala Glu Val Ala Arg
3845                3850                3855

Leu Leu Leu Glu Ala Gln Ala Ala Thr Gly Phe Leu Leu Asp Pro
3860                3865                3870

Val Lys Gly Glu Arg Leu Thr Val Asp Glu Ala Val Arg Lys Gly
3875                3880                3885

Leu Val Gly Pro Glu Leu His Asp Arg Leu Leu Ser Ala Glu Arg
3890                3895                3900

Ala Val Thr Gly Tyr Arg Asp Pro Tyr Thr Glu Gln Thr Ile Ser
3905                3910                3915

Leu Phe Gln Ala Met Lys Lys Glu Leu Ile Pro Thr Glu Glu Ala
3920                3925                3930

Leu Arg Leu Leu Asp Ala Gln Leu Ala Thr Gly Gly Ile Val Asp
3935                3940                3945

Pro Arg Leu Gly Phe His Leu Pro Leu Glu Val Ala Tyr Gln Arg
3950                3955                3960

Gly Tyr Leu Asn Lys Asp Thr His Asp Gln Leu Ser Glu Pro Ser
3965                3970                3975

Glu Val Arg Ser Tyr Val Asp Pro Ser Thr Asp Glu Arg Leu Ser
3980                3985                3990

Tyr Thr Gln Leu Leu Arg Arg Cys Arg Arg Asp Asp Gly Thr Gly
3995                4000                4005

Gln Leu Leu Pro Leu Ser Asp Ala Arg Lys Leu Thr Phe Arg
4010                4015                4020

Gly Leu Arg Lys Gln Ile Thr Met Glu Glu Leu Val Arg Ser Gln
4025                4030                4035

Val Met Asp Glu Ala Thr Ala Leu Gln Leu Arg Glu Gly Leu Thr
```

```
                4040            4045            4050
Ser Ile Glu Glu Val Thr Lys Asn Leu Gln Lys Phe Leu Glu Gly
    4055            4060            4065

Thr Ser Cys Ile Ala Gly Val Phe Val Asp Ala Thr Lys Glu Arg
    4070            4075            4080

Leu Ser Val Tyr Gln Ala Met Lys Lys Gly Ile Ile Arg Pro Gly
    4085            4090            4095

Thr Ala Phe Glu Leu Leu Glu Ala Gln Ala Ala Thr Gly Tyr Val
    4100            4105            4110

Ile Asp Pro Ile Lys Gly Leu Lys Leu Thr Val Glu Glu Ala Val
    4115            4120            4125

Arg Met Gly Ile Val Gly Pro Glu Phe Lys Asp Lys Leu Leu Ser
    4130            4135            4140

Ala Glu Arg Ala Val Thr Gly Tyr Lys Asp Pro Tyr Ser Gly Lys
    4145            4150            4155

Leu Ile Ser Leu Phe Gln Ala Met Lys Lys Gly Leu Ile Leu Lys
    4160            4165            4170

Asp His Gly Ile Arg Leu Leu Glu Ala Gln Ile Ala Thr Gly Gly
    4175            4180            4185

Ile Ile Asp Pro Glu Glu Ser His Arg Leu Pro Val Glu Val Ala
    4190            4195            4200

Tyr Lys Arg Gly Leu Phe Asp Glu Glu Met Asn Glu Ile Leu Thr
    4205            4210            4215

Asp Pro Ser Asp Asp Thr Lys Gly Phe Phe Asp Pro Asn Thr Glu
    4220            4225            4230

Glu Asn Leu Thr Tyr Leu Gln Leu Met Glu Arg Cys Ile Thr Asp
    4235            4240            4245

Pro Gln Thr Gly Leu Cys Leu Leu Pro Leu Lys Glu Lys Lys Arg
    4250            4255            4260

Glu Arg Lys Thr Ser Ser Lys Ser Ser Val Arg Lys Arg Arg Val
    4265            4270            4275

Val Ile Val Asp Pro Glu Thr Gly Lys Glu Met Ser Val Tyr Glu
    4280            4285            4290

Ala Tyr Arg Lys Gly Leu Ile Asp His Gln Thr Tyr Leu Glu Leu
    4295            4300            4305

Ser Glu Gln Glu Cys Glu Trp Glu Glu Ile Thr Ile Ser Ser Ser
    4310            4315            4320

Asp Gly Val Val Lys Ser Met Ile Ile Asp Arg Arg Ser Gly Arg
    4325            4330            4335

Gln Tyr Asp Ile Asp Asp Ala Ile Ala Lys Asn Leu Ile Asp Arg
    4340            4345            4350

Ser Ala Leu Asp Gln Tyr Arg Ala Gly Thr Leu Ser Ile Thr Glu
    4355            4360            4365

Phe Ala Asp Met Leu Ser Gly Asn Ala Gly Gly Phe Arg Ser Arg
    4370            4375            4380

Ser Ser Ser Val Gly Ser Ser Ser Ser Tyr Pro Ile Ser Pro Ala
    4385            4390            4395

Val Ser Arg Thr Gln Leu Ala Ser Trp Ser Asp Pro Thr Glu Glu
    4400            4405            4410

Thr Gly Pro Val Ala Gly Ile Leu Asp Thr Glu Thr Leu Glu Lys
    4415            4420            4425

Val Ser Ile Thr Glu Ala Met His Arg Asn Leu Val Asp Asn Ile
    4430            4435            4440
```

```
Thr Gly Gln Arg Leu Leu Glu Ala Gln Ala Cys Thr Gly Gly Ile
    4445                4450                4455

Ile Asp Pro Ser Thr Gly Glu Arg Phe Pro Val Thr Asp Ala Val
4460                4465                4470

Asn Lys Gly Leu Val Asp Lys Ile Met Val Asp Arg Ile Asn Leu
    4475                4480                4485

Ala Gln Lys Ala Phe Cys Gly Phe Glu Asp Pro Arg Thr Lys Thr
    4490                4495                4500

Lys Met Ser Ala Ala Gln Ala Leu Lys Lys Gly Trp Leu Tyr Tyr
    4505                4510                4515

Glu Ala Gly Gln Arg Phe Leu Glu Val Gln Tyr Leu Thr Gly Gly
    4520                4525                4530

Leu Ile Glu Pro Asp Thr Pro Gly Arg Val Pro Leu Asp Glu Ala
    4535                4540                4545

Leu Gln Arg Gly Thr Val Asp Ala Arg Thr Ala Gln Lys Leu Arg
    4550                4555                4560

Asp Val Gly Ala Tyr Ser Lys Tyr Leu Thr Cys Pro Lys Thr Lys
    4565                4570                4575

Leu Lys Ile Ser Tyr Lys Asp Ala Leu Asp Arg Ser Met Val Glu
    4580                4585                4590

Glu Gly Thr Gly Leu Arg Leu Leu Glu Ala Ala Ala Gln Ser Thr
    4595                4600                4605

Lys Gly Tyr Tyr Ser Pro Tyr Ser Val Ser Gly Ser Gly Ser Thr
    4610                4615                4620

Ala Gly Ser Arg Thr Gly Ser Arg Thr Gly Ser Arg Ala Gly Ser
    4625                4630                4635

Arg Arg Gly Ser Phe Asp Ala Thr Gly Ser Gly Phe Ser Met Thr
    4640                4645                4650

Phe Ser Ser Ser Ser Tyr Ser Ser Gly Tyr Gly Arg Arg Tyr
    4655                4660                4665

Ala Ser Gly Ser Ser Ala Ser Leu Gly Gly Pro Glu Ser Ala Val
    4670                4675                4680

Ala

<210> SEQ ID NO 2
<211> LENGTH: 364
<212> TYPE: PRT
<213> ORGANISM: Homo sapiens

<400> SEQUENCE: 2

Ser Ser Ser Asp Gly Val Val Lys Ser Met Ile Ile Asp Arg Arg Ser
1               5                   10                  15

Gly Arg Gln Tyr Asp Ile Asp Asp Ala Ile Ala Lys Asn Leu Ile Asp
                20                  25                  30

Arg Ser Ala Leu Asp Gln Tyr Arg Ala Gly Thr Leu Ser Ile Thr Glu
            35                  40                  45

Phe Ala Asp Met Leu Ser Gly Asn Ala Gly Gly Phe Arg Ser Arg Ser
        50                  55                  60

Ser Ser Val Gly Ser Ser Ser Tyr Pro Ile Ser Pro Ala Val Ser
65                  70                  75                  80

Arg Thr Gln Leu Ala Ser Trp Ser Asp Pro Thr Glu Glu Thr Gly Pro
                85                  90                  95

Val Ala Gly Ile Leu Asp Thr Glu Thr Leu Glu Lys Val Ser Ile Thr
                100                 105                 110
```

-continued

Glu Ala Met His Arg Asn Leu Val Asp Asn Ile Thr Gly Gln Arg Leu
            115                 120                 125

Leu Glu Ala Gln Ala Cys Thr Gly Gly Ile Ile Asp Pro Ser Thr Gly
        130                 135                 140

Glu Arg Phe Pro Val Thr Asp Ala Val Asn Lys Gly Leu Val Asp Lys
145                 150                 155                 160

Ile Met Val Asp Arg Ile Asn Leu Ala Gln Lys Ala Phe Cys Gly Phe
                165                 170                 175

Glu Asp Pro Arg Thr Lys Thr Lys Met Ser Ala Ala Gln Ala Leu Lys
            180                 185                 190

Lys Gly Trp Leu Tyr Tyr Glu Ala Gly Gln Arg Phe Leu Glu Val Gln
        195                 200                 205

Tyr Leu Thr Gly Gly Leu Ile Glu Pro Asp Thr Pro Gly Arg Val Pro
    210                 215                 220

Leu Asp Glu Ala Leu Gln Arg Gly Thr Val Asp Ala Arg Thr Ala Gln
225                 230                 235                 240

Lys Leu Arg Asp Val Gly Ala Tyr Ser Lys Tyr Leu Thr Cys Pro Lys
                245                 250                 255

Thr Lys Leu Lys Ile Ser Tyr Lys Asp Ala Leu Asp Arg Ser Met Val
            260                 265                 270

Glu Glu Gly Thr Gly Leu Arg Leu Leu Glu Ala Ala Gln Ser Thr
        275                 280                 285

Lys Gly Tyr Tyr Ser Pro Tyr Ser Val Ser Gly Ser Gly Ser Thr Ala
    290                 295                 300

Gly Ser Arg Thr Gly Ser Arg Thr Gly Ser Arg Ala Gly Ser Arg Arg
305                 310                 315                 320

Gly Ser Phe Asp Ala Thr Gly Ser Gly Phe Ser Met Thr Phe Ser Ser
                325                 330                 335

Ser Ser Tyr Ser Ser Ser Gly Tyr Gly Arg Arg Tyr Ala Ser Gly Ser
            340                 345                 350

Ser Ala Ser Leu Gly Gly Pro Glu Ser Ala Val Ala
        355                 360

<210> SEQ ID NO 3
<211> LENGTH: 1398
<212> TYPE: DNA
<213> ORGANISM: Artificial Sequence
<220> FEATURE:
<223> OTHER INFORMATION: Synthetic Polynucleotide

<400> SEQUENCE: 3
atgaacttcg ggctcagctt gattttcctt gccctcattt taaaaggtgt ccagtgtgag    60
gtgcagctgg tggagtctgg gggagacttg gtgaagcctg agggtccct gaaactctcc    120 tgtgcagcct ctggattcac tttcagtagg tatggcatgt cttgggttcg ccagactcca    180
gacaagaggc tggagtgggt cgcaaccatt agtattggtg gtacttacac ctactatcca    240
gacagtatga agggcgatt caccatctcc agagacaatg ccaagaacac cctgtacctg    300
caaatgagca gtctgaagtc tgaggacaca gccatgtatt actgtgcaag acgggggtat    360
ggtaactact cttactatgg tatggactac tggggtcaag gaacctcagt caccgtctcc    420
tcagccaaaa cgacaccccc atctgtctat ccactggccc ctggatctgc tgcccaaact    480
aactccatgg tgaccctggg atgcctggtc aagggctatt ccctgagcc agtgacagtg    540 acctggaact ctggatccct gtccagcggg gtgcacacct tcccagctgt cctgcagtct    600

```
gacctctaca ctctgagcag ctcagtgact gtccctcca gcacctggcc cagcgagacc      660
gtcacctgca acgttgccca cccggccagc agcaccaagg tggacaagaa aattgtgccc      720
agggattgtg gttgtaagcc ttgcatatgt acagtcccag aagtatcatc tgtcttcatc      780
ttccccccaa agcccaagga tgtgctcacc attactctga ctcctaaggt cacgtgtgtt      840
gtggtagaca tcagcaagga tgatcccgag gtccagttca gctggtttgt agatgatgtg      900
gaggtgcaca cagctcagac gcaaccccgg gaggagcagt tcaacagcac tttccgctca      960
gtcagtgaac ttcccatcat gcaccaggac tggctcaatg gcaaggagtt caaatgcagg     1020
gtcaacagtg cagctttccc tgcccccatc gagaaaacca ctccaaaac caaaggcaga     1080 ccgaaggctc acaggtgta caccattcca cctcccaagg agcagatggc caaggataaa     1140
gtcagtctga cctgcatgat aacagacttc ttccctgaag acattactgt ggagtggcag     1200
tggaatgggc agccagcgga gaactacaag aacactcagc ccatcatgga cacagatggc     1260
tcttacttcg tctacagcaa gctcaatgtg cagaagagca ctgggaggc aggaaatact     1320 ttcacctgct ctgtgttaca tgagggcctg cacaaccacc atactgagaa gagcctctcc     1380
cactctcctg gtaaatga                                                   1398

<210> SEQ ID NO 4
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 4
atgaacttcg ggctcagctt gattttcctt gccctcattt taaaggtgt ccagtgt         57

<210> SEQ ID NO 5
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 5
gaggtgcagc tggtggagtc tgggggagac ttggtgaagc ctggagggtc cctgaaactc      60
tcctgtgcag cctctggatt cactttcagt                                       90

<210> SEQ ID NO 6
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 6
aggtatggca tgtct                                                       15

<210> SEQ ID NO 7
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 7
tgggttcgcc agactccaga caagaggctg gagtgggtcg ca                         42
```

```
<210> SEQ ID NO 8
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 8
accattagta ttggtggtac ttacacctac tatccagaca gtatgaaggg g            51

<210> SEQ ID NO 9
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 9
cgattcacca tctccagaga caatgccaag aacaccctgt acctgcaaat gagcagtctg    60
aagtctgagg acacagccat gtattactgt gcaaga                              96

<210> SEQ ID NO 10
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 10
cgggggtatg gtaactactc ttactatggt atggactac                           39

<210> SEQ ID NO 11
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 11
tggggtcaag gaacctcagt caccgtctcc tca                                 33

<210> SEQ ID NO 12
<211> LENGTH: 366
<212> TYPE: DNA
<213> ORGANISM: Artificial Sequence
<220> FEATURE:
<223> OTHER INFORMATION: Synthetic Polynucleotide

<400> SEQUENCE: 12
gaggtgcagc tggtggagtc tgggggagac ttggtgaagc ctggagggtc cctgaaactc    60
tcctgtgcag cctctggatt cactttcagt aggtatggca tgtcttgggt tcgccagact   120
ccagacaaga ggctggagtg ggtcgcaacc attagtattg gtggtactta cacctactat   180
ccagacagta tgaaggggcg attcaccatc tccagagaca tgccaagaa cacccctgtac   240 ctgcaaatga gcagtctgaa gtctgaggac acagccatgt attactgtgc aagacggggg   300
tatggtaact actcttacta tggtatggac tactggggtc aaggaacctc agtcaccgtc   360
tcctca                                                              366

<210> SEQ ID NO 13
<211> LENGTH: 972
<212> TYPE: DNA
<213> ORGANISM: Artificial Sequence
<220> FEATURE:
```

<223> OTHER INFORMATION: Synthetic Polynucleotide

<400> SEQUENCE: 13

```
gccaaaacga caccccatc tgtctatcca ctggcccctg gatctgctgc ccaaactaac      60
tccatggtga ccctgggatg cctggtcaag ggctatttcc ctgagccagt gacagtgacc     120
tggaactctg gatccctgtc cagcggtgtg cacaccttcc cagctgtcct gcagtctgac    180
ctctacactc tgagcagctc agtgactgtc ccctccagca cctggcccag cgagaccgtc    240
acctgcaacg ttgcccaccc ggccagcagc accaaggtgg acaagaaaat tgtgcccagg    300
gattgtggtt gtaagccttg catatgtaca gtcccagaag tatcatctgt cttcatcttc    360
cccccaaagc ccaaggatgt gctcaccatt actctgactc ctaaggtcac gtgtgttgtg    420
gtagacatca gcaaggatga tcccgaggtc cagttcagct ggtttgtaga tgatgtggag    480
gtgcacacag ctcagacgca accccgggag gagcagttca cagcactttt ccgctcagtc    540
agtgaacttc ccatcatgca ccaggactgg ctcaatggca aggagttcaa atgcagggtc    600
aacagtgcag ctttccctgc ccccatcgag aaaaccatct ccaaaaccaa aggcagaccg    660
aaggctccac aggtgtacac cattccacct cccaaggagc agatggccaa ggataaagtc    720
agtctgacct gcatgataac agacttcttc cctgaagaca ttactgtgga gtggcagtgg    780
aatgggcagc cagcggagaa ctacaagaac actcagccca tcatggacac agatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aa                                                         972
```

<210> SEQ ID NO 14
<211> LENGTH: 201
<212> TYPE: PRT
<213> ORGANISM: Artificial Sequence
<220> FEATURE:
<223> OTHER INFORMATION: Synthetic Polypeptide

<400> SEQUENCE: 14

```
Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
                20                  25                  30

Pro Gly Gly Ser Leu Lys Leu Ser Cys Ala Ala Ser Gly Phe Thr Phe
            35                  40                  45

Ser Arg Tyr Gly Met Ser Trp Val Arg Gln Thr Pro Asp Lys Arg Leu
        50                  55                  60

Glu Trp Val Ala Thr Ile Ser Ile Gly Gly Thr Tyr Thr Tyr Tyr Pro
65                  70                  75                  80

Asp Ser Met Lys Gly Arg Phe Thr Ile Ser Arg Asp Asn Ala Lys Asn
                85                  90                  95

Thr Leu Tyr Leu Gln Met Ser Ser Leu Lys Ser Glu Thr Ala Met
                100                 105                 110

Tyr Tyr Cys Ala Arg Arg Gly Tyr Gly Asn Tyr Ser Tyr Tyr Gly Met
            115                 120                 125

Asp Tyr Trp Gly Gln Gly Thr Ser Val Thr Val Ser Ala Lys Thr
        130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
```

```
                165                 170                 175
Pro Val Thr Val Thr Trp Asn Ser Gly Ser Leu Ser Ser Gly Val His
        180                 185                 190

Thr Phe Pro Ala Val Leu Gln Ser Asp
        195                 200

<210> SEQ ID NO 15
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 15

Met Asn Phe Gly Leu Ser Leu Ile Phe Leu Ala Leu Ile Leu Lys Gly
1               5                   10                  15

Val Gln Cys

<210> SEQ ID NO 16
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 16

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser
        20                  25                  30

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 17

Arg Tyr Gly Met Ser
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 18

Trp Val Arg Gln Thr Pro Asp Lys Arg Leu Glu Trp Val Ala
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 19

Thr Ile Ser Ile Gly Gly Thr Tyr Thr Tyr Tyr Pro Asp Ser Met Lys
1               5                   10                  15

Gly
```

```
<210> SEQ ID NO 20
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 20

Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Ala Arg
            20                  25                  30

<210> SEQ ID NO 21
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 21

Arg Gly Tyr Gly Asn Tyr Ser Tyr Tyr Gly Met Asp Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 22

Trp Gly Gln Gly Thr Ser Val Thr Val Ser Ser
1               5                   10

<210> SEQ ID NO 23
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 23

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Ser Ile Gly Gly Thr Tyr Thr Tyr Pro Asp Ser Met
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Gly Tyr Gly Asn Tyr Ser Tyr Tyr Gly Met Asp Tyr Trp
            100                 105                 110

Gly Gln Gly Thr Ser Val Thr Val Ser Ser
        115                 120

<210> SEQ ID NO 24
```

```
<211> LENGTH: 324
<212> TYPE: PRT
<213> ORGANISM: Artificial Sequence
<220> FEATURE:
<223> OTHER INFORMATION: Synthetic Polypeptide

<400> SEQUENCE: 24

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 25
<211> LENGTH: 720
<212> TYPE: DNA
<213> ORGANISM: Artificial Sequence
<220> FEATURE:
<223> OTHER INFORMATION: Synthetic Polynucleotide

<400> SEQUENCE: 25
```

```
atgaggttct ctgctcagct tctggggctg cttgtgctct ggatccctgg atccactgca      60
gatattgtga tgacgcaggc tgcattctcc aatccagtca ctcttggaac atcagcttcc     120
atctcctgca ggtctagtaa gagtctccta catagtaatg gcatcactta tttgtattgg     180
tatctgcaga agccaggcca gtctcctcag ctcctgattt atcagatgtc aaccttgcc      240 tcaggagtcc cagacaggtt cagtagcagt gggtcaggaa ctgatttcac actgagaatc     300
agcagagtgg aggctgagga tgtgggtgtt tattactgtg ctcaaaatct agaacttccg     360
ctcacgttcg gtgctgggac caagctggag ctgaaacggg ctgatgctgc accaactgta     420
tccatcttcc caccatccag tgagcagtta acatctggag gtgcctcagt cgtgtgcttc     480
ttgaacaact ctacccccaa agacatcaat gtcaagtgga gattgatgg cagtgaacga     540 caaaatggcg tcctgaacag ttggactgat caggacagca agacagcac ctacagcatg     600 agcagcaccc tcacgttgac caaggacgag tatgaacgac ataacagcta tacctgtgag     660
gccactcaca agacatcaac ttcacccatt gtcaagagct caacaggaa tgagtgttag     720
```

```
<210> SEQ ID NO 26
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 26
atgaggttct ctgctcagct tctggggctg cttgtgctct ggatccctgg atccactgca      60
```

```
<210> SEQ ID NO 27
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 27
gatattgtga tgacgcaggc tgcattctcc aatccagtca ctcttggaac atcagcttcc      60
atctcctgc                                                              69
```

```
<210> SEQ ID NO 28
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 28
aggtctagta agagtctcct acatagtaat ggcatcactt atttgtat                   48
```

```
<210> SEQ ID NO 29
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 29
tggtatctgc agaagccagg ccagtctcct cagctcctga tttat                      45
```

```
<210> SEQ ID NO 30
<211> LENGTH: 21
<212> TYPE: DNA
```

<210> SEQ ID NO 30
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 30
cagatgtcca accttgcctc a                                                21

<210> SEQ ID NO 31
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 31
ggagtcccag acaggttcag tagcagtggg tcaggaactg atttcacact gagaatcagc      60
agagtggagg ctgaggatgt gggtgtttat tactgt                                96

<210> SEQ ID NO 32
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 32
gctcaaaatc tagaacttcc gctcacg                                          27

<210> SEQ ID NO 33
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 33
ttcggtgctg ggaccaagct ggagctgaaa                                       30

<210> SEQ ID NO 34
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 34
gatattgtga tgacgcaggc tgcattctcc aatccagtca ctcttggaac atcagcttcc      60
atctcctgca ggtc                                                        74

<210> SEQ ID NO 35
<211> LENGTH: 382
<212> TYPE: DNA
<213> ORGANISM: Artificial Sequence
<220> FEATURE:
<223> OTHER INFORMATION: Synthetic Polynucleotide

<400> SEQUENCE: 35
ctgtgctcaa aatctagaac ttccgctcac gttcggtgct gggaccaagc tggagctgaa      60
acgggctgat gctgcaccaa ctgtatccat cttcccacca tccagtgagc agttaacatc     120
tggaggtgcc tcagtcgtgt gcttcttgaa caacttctac cccaaagaca tcaatgtcaa     180
gtggaagatt gatggcagtg aacgacaaaa tggcgtcctg aacagttgga ctgatcagga     240
cagcaaagac agcacctaca gcatgagcag caccctcacg ttgaccaagg acgagtatga     300
acgacataac agctatacct gtgaggccac tcacaagaca tcaacttcac ccattgtcaa    360
gagcttcaac aggaatgagt gt                                             382

<210> SEQ ID NO 36
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 36

Met Arg Phe Ser Ala Gln Leu Leu Gly Leu Leu Val Leu Trp Ile Pro
1               5                   10                  15

Gly Ser Thr Ala Asp Ile Val Met Thr Gln Ala Ala Phe Ser Asn Pro
            20                  25                  30

Val Thr Leu Gly Thr Ser Ala Ser Ile Ser Cys Arg Ser Ser Lys Ser
        35                  40                  45

Leu Leu His Ser Asn Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Leu Thr Phe Gly Ala Gly Thr Lys
        115                 120                 125

Leu Glu Leu Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 37
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 37

Met Arg Phe Ser Ala Gln Leu Leu Gly Leu Leu Val Leu Trp Ile Pro
1               5                   10                  15

Gly Ser Thr Ala
            20

<210> SEQ ID NO 38
<211> LENGTH: 23

```
<212> TYPE: PRT
<213> ORGANISM: Artificial Sequence
<220> FEATURE:
<223> OTHER INFORMATION: Synthetic Polypeptide

<400> SEQUENCE: 38

Asp Ile Val Met Thr Gln Ala Ala Phe Ser Asn Pro Val Thr Leu Gly
1               5                   10                  15

Thr Ser Ala Ser Ile Ser Cys
            20

<210> SEQ ID NO 39
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 39

Arg Ser Ser Lys Ser Leu Leu His Ser Asn Gly Ile Thr Tyr Leu Tyr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 40

Trp Tyr Leu Gln Lys Pro Gly Gln Ser Pro Gln Leu Leu Ile Tyr
1               5                   10                  15

<210> SEQ ID NO 41
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 41

Gln Met Ser Asn Leu Ala Ser
1               5

<210> SEQ ID NO 42
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 42

Gly Val Pro Asp Arg Phe Ser Ser Gly Ser Gly Thr Asp Phe Thr
1               5                   10                  15

Leu Arg Ile Ser Arg Val Glu Ala Glu Asp Val Gly Val Tyr Tyr Cys
            20                  25                  30

<210> SEQ ID NO 43
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 43

Ala Gln Asn Leu Glu Leu Pro Leu Thr
```

<210> SEQ ID NO 44
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 44

```
Phe Gly Ala Gly Thr Lys Leu Glu Leu Lys
1               5                   10
```

<210> SEQ ID NO 45
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 45

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110
```

<210> SEQ ID NO 46
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 46

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 47

<211> LENGTH: 1410
<212> TYPE: DNA
<213> ORGANISM: Artificial Sequence
<220> FEATURE:
<223> OTHER INFORMATION: Synthetic Polynucleotide

<400> SEQUENCE: 47

```
atggcttggg tgtggacctt gctattcctg atggcagctg cccaaagtat ccaagcacag      60
atccagttgg tgcagtctgg acctgagctg aagaagcctg agagacagt caagatctcc     120
tgcaaggctt ctggttatac cttcacagac tattcaatgc actgggtgaa gcaggctcca     180
ggaaagggtt taaagtggat gggctggata aacactgaga ctggtgagcc aacatatgca     240
gatgacttca agggacggtt tgccttctct ttggaaacct ctgccagcac tgcctatttg     300
cagatcaaca acctcaaaaa tgaggacacg gctacatatt tctgtgcccc cggagggttt     360
gcttactggg gccaagggac tctggtcact gtctctgcag ccaaaacaac cccccatca     420
gtctatccac tggcccctgg gtgtggagat acaactggtt cctccgtgac tctgggatgc     480
ctggtcaagg gctacttccc tgagtcagtg actgtgactt ggaactctgg atccctgtcc     540
agcagtgtgc acaccttccc agctctcctg cagtctggac tctacactat gagcagctca     600
gtgactgtcc cctccagcac ctggccaagt cagaccgtca cctgcagcgt tgctcaccca     660
gccagcagca ccacggtgga caaaaaactt gagcccagcg ggcccatttc aacaatcaac     720
ccctgtcctc catgcaagga gtgtcacaaa tgcccagctc ctaacctcga gggtggacca     780
tccgtcttca tcttccctcc aaatatcaag gatgtactca tgatctccct gacacccaag     840
gtcacgtgtg tggtggtgga tgtgagcgag gatgacccag acgtccagat cagctggttt     900
gtgaacaacg tggaagtaca cacagctcag acacaaaccc atagagagga ttacaacagt     960
actatccggg tggtcagcac cctccccatc cagcaccagg actggatgag tggcaaggag    1020
ttcaaatgca aggtcaacaa caaagacctc ccatcaccca tcgagagaac catctcaaaa    1080
attaaagggc tagtcagagc tccacaagta tacatcttgc cgccaccagc agagcagttg    1140
tccaggaaag atgtcagtct cacttgcctg gtcgtgggct tcaaccctgg agacatcagt    1200
gtggagtgga ccagcaatgg gcatacagag gagaactaca aggacaccgc accagtcctg    1260
gactctgacg gttcttactt catatatagc aagctcaata tgaaaacaag caagtgggag    1320
aaaacagatt ccttctcatg caacgtgaga cacgagggtc tgaaaaatta ctacctgaag    1380
aagaccatct cccggtctcc gggtaaatga                                     1410
```

<210> SEQ ID NO 48
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 48

```
atggcttggg tgtggacctt gctattcctg atggcagctg cccaaagtat ccaagca        57
```

<210> SEQ ID NO 49
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 49

```
cagatccagt tggtgcagtc tggacctgag ctgaagaagc ctggagagac agtcaagatc      60
```
tcctgcaagg cttctggtta taccttcaca                                              90

<210> SEQ ID NO 50
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 50
gactattcaa tgcac                                                              15

<210> SEQ ID NO 51
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 51
tgggtgaagc aggctccagg aaagggttta agtggatgg gc                                 42

<210> SEQ ID NO 52
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 52
tggataaaca ctgagactgg tgagccaaca tatgcagatg acttcaaggg a                      51

<210> SEQ ID NO 53
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 53
cggtttgcct tctctttgga aacctctgcc agcactgcct atttgcagat caacaacctc             60
aaaaatgagg acacggctac atatttctgt gccccc                                       96

<210> SEQ ID NO 54
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 54
ggagggtttg cttac                                                              15

<210> SEQ ID NO 55
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 55
tggggccaag ggactctggt cactgtctct gca                                          33

<210> SEQ ID NO 56

<211> LENGTH: 342
<212> TYPE: DNA
<213> ORGANISM: Artificial Sequence
<220> FEATURE:
<223> OTHER INFORMATION: Synthetic Polynucleotide

<400> SEQUENCE: 56

```
cagatccagt tggtgcagtc tggacctgag ctgaagaagc tggagagac agtcaagatc      60
tcctgcaagg cttctggtta taccttcaca gactattcaa tgcactgggt gaagcaggct    120
ccaggaaagg gtttaaagtg gatgggctgg ataaacactg agactggtga gccaacatat    180
gcagatgact caagggacg gtttgccttc tctttggaaa cctctgccag cactgcctat    240
ttgcagatca acaacctcaa aaatgaggac acggctacat atttctgtgc ccccggaggg    300
tttgcttact ggggccaagg gactctggtc actgtctctg ca                       342
```

<210> SEQ ID NO 57
<211> LENGTH: 1008
<212> TYPE: DNA
<213> ORGANISM: Artificial Sequence
<220> FEATURE:
<223> OTHER INFORMATION: Synthetic Polynucleotide

<400> SEQUENCE: 57

```
gccaaaacaa cacccccatc agtctatcca ctggcccctg ggtgtggaga tacaactggt      60
tcctccgtga ctctgggatg cctggtcaag ggctacttcc ctgagtcagt gactgtgact    120
tggaactctg gatccctgtc cagcagtgtg cacaccttcc cagctctcct gcagtctgga    180
ctctacacta tgagcagctc agtgactgtc ccctccagca cctggccaag tcagaccgtc    240
acctgcagcg ttgctcaccc agccagcagc accacggtgg acaaaaaact gagcccagc    300
gggcccattt caacaatcaa ccctgtcct ccatgcaagg agtgtcacaa atgcccagct    360
cctaacctcg agggtggacc atccgtcttc atcttccctc caaatatcaa ggatgtactc    420
atgatctccc tgacacccaa ggtcacgtgt gtggtggtgg atgtgagcga ggatgaccca    480
gacgtccaga tcagctggtt tgtgaacaac gtggaagtac acacagctca gacacaaacc    540
catagagagg attacaacag tactatccgg gtggtcagca ccctccccat ccagcaccag    600
gactggatga gtggcaagga gttcaaatgc aaggtcaaca acaaagacct cccatcaccc    660
atcgagagaa ccatctcaaa aattaaaggg ctagtcagag ctccacaagt atacatcttg    720
ccgccaccag cagagcagtt gtccaggaaa gatgtcagtc tcacttgcct ggtcgtgggc    780
ttcaaccctg agacatcag tgtggagtgg accagcaatg ggcatacaga ggagaactac    840
aaggacaccg caccagtcct ggactctgac ggttcttact tcatatatag caagctcaat    900
atgaaaacaa gcaagtggga aaaacagat tccttctcat gcaacgtgag acacgagggt    960
ctgaaaaatt actacctgaa gaagaccatc tcccggtctc cgggtaaa             1008
```

<210> SEQ ID NO 58
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 58

```
Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30
```

```
Pro Gly Glu Thr Val Lys Ile Ser Cys Lys Ala Ser Gly Tyr Thr Phe
            35                  40                  45

Thr Asp Tyr Ser Met His Trp Val Lys Gln Ala Pro Gly Lys Gly Leu
 50                  55                  60

Lys Trp Met Gly Trp Ile Asn Thr Glu Thr Gly Glu Pro Thr Tyr Ala
 65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
                100                 105                 110

Tyr Phe Cys Ala Pro Gly Gly Phe Ala Tyr Trp Gly Gln Gly Thr Leu
            115                 120                 125

Val Thr Val Ser Ala Ala Lys Thr Thr Pro Pro Ser Val Tyr Pro Leu
130                 135                 140

Ala Pro Gly Cys Gly Asp Thr Thr Gly Ser Ser Val Thr Leu Gly Cys
145                 150                 155                 160

Leu Val Lys Gly Tyr Phe Pro Glu Ser Val Thr Val Thr Trp Asn Ser
                165                 170                 175

Gly Ser Leu Ser Ser Ser Val His Thr Phe Pro Ala Leu Leu Gln Ser
            180                 185                 190

Gly Leu Tyr Thr Met Ser Ser Ser Val Thr Val Pro Ser Ser Thr Trp
            195                 200                 205

Pro Ser Gln Thr Val Thr Cys Ser Val Ala His Pro Ala Ser Ser Thr
            210                 215                 220

Thr Val Asp Lys Lys Leu Glu Pro Ser Gly Pro Ile Ser Thr Ile Asn
225                 230                 235                 240

Pro Cys Pro Pro Cys Lys Glu Cys His Lys Cys Pro Ala Pro Asn Leu
                245                 250                 255

Glu Gly Gly Pro Ser Val Phe Ile Phe Pro Pro Asn Ile Lys Asp Val
            260                 265                 270

Leu Met Ile Ser Leu Thr Pro Lys Val Thr Cys Val Val Val Asp Val
            275                 280                 285

Ser Glu Asp Asp Pro Asp Val Gln Ile Ser Trp Phe Val Asn Asn Val
290                 295                 300

Glu Val His Thr Ala Gln Thr Gln Thr His Arg Glu Asp Tyr Asn Ser
305                 310                 315                 320

Thr Ile Arg Val Val Ser Thr Leu Pro Ile Gln His Gln Asp Trp Met
                325                 330                 335

Ser Gly Lys Glu Phe Lys Cys Lys Val Asn Asn Lys Asp Leu Pro Ser
            340                 345                 350

Pro Ile Glu Arg Thr Ile Ser Lys Ile Lys Gly Leu Val Arg Ala Pro
            355                 360                 365

Gln Val Tyr Ile Leu Pro Pro Pro Ala Glu Gln Leu Ser Arg Lys Asp
370                 375                 380

Val Ser Leu Thr Cys Leu Val Val Gly Phe Asn Pro Gly Asp Ile Ser
385                 390                 395                 400

Val Glu Trp Thr Ser Asn Gly His Thr Glu Glu Asn Tyr Lys Asp Thr
                405                 410                 415

Ala Pro Val Leu Asp Ser Asp Gly Ser Tyr Phe Ile Tyr Ser Lys Leu
            420                 425                 430

Asn Met Lys Thr Ser Lys Trp Glu Lys Thr Asp Ser Phe Ser Cys Asn
            435                 440                 445
```

Val Arg His Glu Gly Leu Lys Asn Tyr Tyr Leu Lys Lys Thr Ile Ser
            450                 455                 460

Arg Ser Pro Gly Lys
465

<210> SEQ ID NO 59
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 59

Met Ala Trp Val Trp Thr Leu Leu Phe Leu Met Ala Ala Ala Gln Ser
1               5                   10                  15

Ile Gln Ala

<210> SEQ ID NO 60
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 60

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30

<210> SEQ ID NO 61
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 61

Asp Tyr Ser Met His
1               5

<210> SEQ ID NO 62
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 62

Trp Val Lys Gln Ala Pro Gly Lys Gly Leu Lys Trp Met Gly
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 63

Trp Ile Asn Thr Glu Thr Gly Glu Pro Thr Tyr Ala Asp Asp Phe Lys
1               5                   10                  15

Gly

```
<210> SEQ ID NO 64
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 64

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Pro
            20                  25                  30

<210> SEQ ID NO 65
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 65

Gly Gly Phe Ala Tyr
1               5

<210> SEQ ID NO 66
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 66

Trp Gly Gln Gly Thr Leu Val Thr Val Ser Ala
1               5                   10

<210> SEQ ID NO 67
<211> LENGTH: 114
<212> TYPE: PRT
<213> ORGANISM: Artificial Sequence
<220> FEATURE:
<223> OTHER INFORMATION: Synthetic Polypeptide

<400> SEQUENCE: 67

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Pro Gly Gly Phe Ala Tyr Trp Gly Gln Gly Thr Leu Val Thr Val
            100                 105                 110

Ser Ala

<210> SEQ ID NO 68
<211> LENGTH: 336
<212> TYPE: PRT
<213> ORGANISM: Artificial Sequence
```

<220> FEATURE:
<223> OTHER INFORMATION: Synthetic Polypeptide

<400> SEQUENCE: 68

```
Ala Lys Thr Thr Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
            35                  40                  45

Ser Val His Thr Phe Pro Ala Leu Leu Gln Ser Gly Leu Tyr Thr Met
        50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Val Asp Lys Lys
                85                  90                  95

Leu Glu Pro Ser Gly Pro Ile Ser Thr Ile Asn Pro Cys Pro Pro Cys
                100                 105                 110

Lys Glu Cys His Lys Cys Pro Ala Pro Asn Leu Glu Gly Gly Pro Ser
                115                 120                 125

Val Phe Ile Phe Pro Pro Asn Ile Lys Asp Val Leu Met Ile Ser Leu
            130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
            195                 200                 205

Lys Cys Lys Val Asn Asn Lys Asp Leu Pro Ser Pro Ile Glu Arg Thr
            210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
            275                 280                 285

Ser Asp Gly Ser Tyr Phe Ile Tyr Ser Lys Leu Asn Met Lys Thr Ser
        290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335
```

<210> SEQ ID NO 69
<211> LENGTH: 720
<212> TYPE: DNA
<213> ORGANISM: Artificial Sequence
<220> FEATURE:
<223> OTHER INFORMATION: Synthetic Polynucleotide

<400> SEQUENCE: 69

```
atgaggtgcc tagctgagtt cctggggctg cttgtgctct ggatccctgg agccattggg    60
```

-continued

```
gatattgtga tgactcaggc tgcaccctct gtacctgtca ctcctggaga gtcagtatcc    120
atctcctgca ggtctagtaa gagtctcctg catagtaatg caacactta cttgtattgg    180 ttcctgcaga ggccaggcca gtctcctcag ctcctgatat atcggatgtc caaccttgcc   240
tcaggagtcc cagacaggtt cagtggcagt gggtcaggaa ctgctttcac actgagaatc   300
agtagagtgg aggctgagga tgtgggtgtt tattactgta tgcaacatct agaatatccg   360
ctcacgttcg gtgctgggac caagctggag ctgaaacggg ctgatgctgc accaactgta   420
tccatcttcc caccatccag tgagcagtta acatctggag gtgcctcagt cgtgtgcttc   480
ttgaacaact ctaccccaa agacatcaat gtcaagtgga gattgatgg cagtgaacga     540 caaaatggcg tcctgaacag ttggactgat caggacagca agacagcac ctacagcatg    600 agcagcaccc tcacgttgac caaggacgag tatgaacgac ataacagcta cctgtgag     660 gccactcaca agacatcaac ttcacccatt gtcaagagct caacaggaa tgagtgttag    720
```

<210> SEQ ID NO 70
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 70

```
atgaggtgcc tagctgagtt cctggggctg cttgtgctct ggatccctgg agccattggg    60
```

<210> SEQ ID NO 71
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 71

```
gatattgtga tgactcaggc tgcaccctct gtacctgtca ctcctggaga gtcagtatcc    60
atctcctgc                                                            69
```

<210> SEQ ID NO 72
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 72

```
aggtctagta agagtctcct gcatagtaat ggcaacactt acttgtat                 48
```

<210> SEQ ID NO 73
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 73

```
tggttcctgc agaggccagg ccagtctcct cagctcctga tatat                    45
```

<210> SEQ ID NO 74
<211> LENGTH: 21
<212> TYPE: DNA
<213> ORGANISM: Artificial Sequence
<220> FEATURE:

<223> OTHER INFORMATION: Synthetic Polynucleotide

<400> SEQUENCE: 74
cggatgtcca accttgcctc a                                         21

<210> SEQ ID NO 75
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 75
ggagtcccag acaggttcag tggcagtggg tcaggaactg ctttcacact gagaatcagt   60
agagtggagg ctgaggatgt gggtgtttat tactgt                           96

<210> SEQ ID NO 76
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 76
atgcaacatc tagaatatcc gctcacg                                    27

<210> SEQ ID NO 77
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 77
ttcggtgctg ggaccaagct ggagctgaaa                                 30

<210> SEQ ID NO 78
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 78
gatattgtga tgactcaggc tgcaccctct gtacctgtca ctcctggaga gtcagtatcc   60
atctcctgca ggtctagtaa gagtctcctg catagtaatg caacactta cttgtattgg  120 ttcctgcaga ggccaggcca gtctcctcag ctcctgatat atcggatgtc caaccttgcc  180
tcaggagtcc cagacaggtt cagtggcagt gggtcaggaa ctgctttcac actgagaatc  240
agtagagtgg aggctgagga tgtgggtgtt tattactgta tgcaacatct agaatatccg  300
ctcacgttcg gtgctgggac caagctggag ctgaaa                           336

<210> SEQ ID NO 79
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 79
cgggctgatg ctgcaccaac tgtatccatc ttcccaccat ccagtgagca gttaacatct   60
ggaggtgcct cagtcgtgtg cttcttgaac aacttctacc ccaaagacat caatgtcaag  120

```
tggaagattg atggcagtga acgacaaaat ggcgtcctga acagttggac tgatcaggac    180
agcaaagaca gcacctacag catgagcagc accctcacgt tgaccaagga cgagtatgaa    240
cgacataaca gctatacctg tgaggccact cacaagacat caacttcacc cattgtcaag    300
agcttcaaca ggaatgagtg t                                              321
```

```
<210> SEQ ID NO 80
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 80
```

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Thr Ala Phe
            85                  90                  95

Thr Leu Arg Ile Ser Arg Val Glu Ala Glu Asp Val Gly Val Tyr Tyr
            100                 105                 110

Cys Met Gln His Leu Glu Tyr Pro Leu Thr Phe Gly Ala Gly Thr Lys
            115                 120                 125

Leu Glu Leu Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

```
<210> SEQ ID NO 81
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 81
```

Met Arg Cys Leu Ala Glu Phe Leu Gly Leu Leu Val Leu Trp Ile Pro
1               5                   10                  15

Gly Ala Ile Gly
            20

```
<210> SEQ ID NO 82
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 82

Asp Ile Val Met Thr Gln Ala Ala Pro Ser Val Pro Val Thr Pro Gly
1               5                   10                  15

Glu Ser Val Ser Ile Ser Cys
            20

<210> SEQ ID NO 83
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 83

Arg Ser Ser Lys Ser Leu Leu His Ser Asn Gly Asn Thr Tyr Leu Tyr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 84

Trp Phe Leu Gln Arg Pro Gly Gln Ser Pro Gln Leu Leu Ile Tyr
1               5                   10                  15

<210> SEQ ID NO 85
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 85

Arg Met Ser Asn Leu Ala Ser
1               5

<210> SEQ ID NO 86
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 86

Gly Val Pro Asp Arg Phe Ser Gly Ser Gly Ser Gly Thr Ala Phe Thr
1               5                   10                  15

Leu Arg Ile Ser Arg Val Glu Ala Glu Asp Val Gly Val Tyr Tyr Cys
            20                  25                  30

<210> SEQ ID NO 87
<211> LENGTH: 9
<212> TYPE: PRT
<213> ORGANISM: Artificial Sequence
<220> FEATURE:
<223> OTHER INFORMATION: Synthetic Polypeptide
```

<400> SEQUENCE: 87

Met Gln His Leu Glu Tyr Pro Leu Thr
1               5

<210> SEQ ID NO 88
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 88

Phe Gly Ala Gly Thr Lys Leu Glu Leu Lys Arg
1               5                   10

<210> SEQ ID NO 89
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 89

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

Arg

<210> SEQ ID NO 90
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 90

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

```
Ile Val Lys Ser Phe Asn Arg Asn Glu Cys
            100                 105

<210> SEQ ID NO 91
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 91

Gly Gly Gly Ser
1
```